(12) United States Patent
Stoessel et al.

(10) Patent No.: US 10,050,218 B2
(45) Date of Patent: Aug. 14, 2018

(54) METAL COMPLEXES AND USE THEREOF IN ELECTRONIC DEVICES

(71) Applicant: Merck Patent GmbH, Darmstadt (DE)

(72) Inventors: Philipp Stoessel, Frankfurt Am Main (DE); Nils Koenen, Darmstadt (DE); Esther Breuning, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 364 days.

(21) Appl. No.: 14/783,642

(22) PCT Filed: Mar. 14, 2014

(86) PCT No.: PCT/EP2014/000707
§ 371 (c)(1),
(2) Date: Oct. 9, 2015

(87) PCT Pub. No.: WO2014/166577
PCT Pub. Date: Oct. 16, 2014

(65) Prior Publication Data
US 2016/0308149 A1 Oct. 20, 2016

(30) Foreign Application Priority Data
Apr. 11, 2013 (EP) .................. 13001885

(51) Int. Cl.
| | | |
|---|---|---|
| *H01L 51/00* | (2006.01) | |
| *C07F 15/00* | (2006.01) | |
| *H01L 51/50* | (2006.01) | |
| *C09K 11/06* | (2006.01) | |
| *C09K 11/02* | (2006.01) | |

(52) U.S. Cl.
CPC ...... *H01L 51/0085* (2013.01); *C07F 15/0033* (2013.01); *C09K 11/025* (2013.01); *C09K 11/06* (2013.01); *H01L 51/0003* (2013.01); *H01L 51/0067* (2013.01); *H01L 51/0072* (2013.01); *H01L 51/5016* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1092* (2013.01); *C09K 2211/185* (2013.01); *H01L 51/006* (2013.01); *H01L 51/0052* (2013.01); *H01L 51/0056* (2013.01); *H01L 51/0059* (2013.01); *H01L 51/0077* (2013.01); *H01L 51/0094* (2013.01); *H01L 51/5012* (2013.01); *H01L 2251/5384* (2013.01); *Y02E 10/549* (2013.01)

(58) Field of Classification Search
CPC .................................................. H01L 51/0085
See application file for complete search history.

(56) References Cited

U.S. PATENT DOCUMENTS

2012/0199794 A1* 8/2012 Stoessel .............. C07F 15/0033
252/301.16

FOREIGN PATENT DOCUMENTS

DE 102009049587 A1 4/2011
WO WO-2011044988 A1 * 4/2011 .......... C07F 15/0033

* cited by examiner

*Primary Examiner* — Jennifer A Chriss
*Assistant Examiner* — Sean M DeGuire
(74) *Attorney, Agent, or Firm* — Kim Winston LLP

(57) ABSTRACT

The present invention relates metal complexes and to electronic devices, particularly organic electroluminescent devices containing said metal complexes.

27 Claims, No Drawings

METAL COMPLEXES AND USE THEREOF IN ELECTRONIC DEVICES

RELATED APPLICATIONS

This application is a national stage entry, filed pursuant to 35 U.S.C. § 371, of PCT/EP2014/000707, filed Mar. 14, 2014, which claims the benefit of European Patent Application No. 13001885.6, filed Apr. 11, 2013, which is incorporated herein by reference in its entirety.

The present invention relates to metal complexes for use in electronic devices, in particular as emitters in organic electroluminescent devices, and to organic electroluminescent devices comprising these metal complexes.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in the energy and power efficiency is possible using organometallic compounds as phosphorescence emitters. In general, however, there is still a need for improvement in OLEDs which exhibit triplet emission, in particular with respect to efficiency, operating voltage and lifetime.

In accordance with the prior art, iridium and platinum complexes, in particular, are employed as triplet emitters in phosphorescent OLEDs. It has been possible to achieve an improvement in these OLEDs by employing metal complexes having polypodal ligands or cryptates, providing the complexes with higher thermal stability, which results in a longer lifetime of the OLEDs (WO 04/081017, WO 05/113563, WO 06/008069). Here too, however, further improvements are still desirable.

The prior art furthermore discloses iridium complexes which contain quinalozine derivatives as ligands (WO 2011/044988).

Here too, further improvements with respect to efficiency, operating voltage and lifetime are still desirable.

The object of the present invention is therefore the provision of novel metal complexes which are suitable as emitters for use in OLEDs.

Surprisingly, it has been found that certain metal chelate complexes described in greater detail below achieve this object and exhibit good properties in organic electroluminescent device, in particular with respect to the operating voltage, the efficiency and the emission colour. The present invention therefore relates to these metal complexes and to organic electroluminescent devices which comprise these complexes.

The invention thus relates to a compound of the formula (1), $$M(L)_n(L')_m \quad \text{formula (1)}$$

where the compound of the general formula (1) contains a moiety $M(L)_n$ of the formula (2):

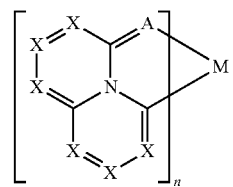

formula (2)

where the following applies to the symbols and indices used:

M is a transition metal;
A is on each occurrence, identically or differently, O, S or NR;
X is on each occurrence, identically or differently, CR or N; or two adjacent groups stand for a group of the following formula (3) or (4),

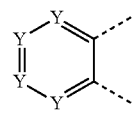

formula (3)

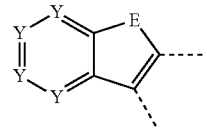

formula (4)

where the dashed bonds indicate the linking of this group in the molecule;
Y is on each occurrence, identically or differently, CR or N;
E is on each occurrence, identically or differently, $CR_2$, NR, O or S;
R is on each occurrence, identically or differently, H, D, F, Cl, Br, I, $N(R^1)_2$, $P(R^1)_2$, CN, $NO_2$, $Si(R^1)_3$, $B(OR^1)_2$, $C(=O)R^1$, $P(=O)(R^1)_2$, $S(=O)R^1$, $S(=O)_2R^1$, $OSO_2R^1$, OH, SH, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^1$, where one or more non-adjacent $CH_2$ groups may be replaced by $R^1C=CR^1$, $C≡C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aralkyl or heteroaralkyl group having 5 to 60 aromatic ring atoms, which may be substituted by one or more radicals $R^1$, or an aryloxy or heteroaryloxy group having 5 to 60 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$; two or more adjacent radicals R here may also form a mono- or polycyclic, aliphatic, aromatic and/or benzo-fused ring system with one another;
$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$; two or more adjacent radicals $R^1$ here may form a mono- or polycyclic, aliphatic or aromatic ring system with one another;

$R^2$ is on each occurrence, identically or differently, H, D, F or an aliphatic, aromatic and/or heteroaromatic organic radical having 1 to 20 C atoms, in particular a hydrocarbon radical, in which, in addition, one or more H atoms may be replaced by D or F; two or more substituents $R^2$ here may also form a mono- or polycyclic, aliphatic or aromatic ring system with one another;

L' is, identically or differently on each occurrence, any desired co-ligand;

n is 1, 2 or 3;

m is 0, 1, 2, 3 or 4;

a plurality of ligands L here may also be linked to one another or L may be linked to L' via any desired bridge V and thus form a tridentate, tetradentate, pentadentate or hexadentate ligand system.

In formula (3) and (4), localised double bonds are drawn in. It goes without saying that these double bonds do not necessarily have to be localised at the positions at which they are drawn in. Thus, mesomeric limiting structures may also be involved, or the double bonds may be localised at other positions, depending on the position at which the group of the formula (3) or (4) is bonded to the ligand.

The indices n and m here are selected so that the coordination number on the metal M corresponds overall, depending on the metal, to the usual coordination number for this metal. This is usually the coordination number 4, 5 or 6 for transition metals, depending on the metal. It is generally known that metal coordination compounds have different coordination numbers, i.e. bind a different number of ligands, depending on the metal and on the oxidation state of the metal. Since the preferred coordination numbers of metals and metal ions in various oxidation states belong to the general expert knowledge of the person skilled in the art in the area of organometallic chemistry or coordination chemistry, it is readily possible for the person skilled in the art to use a suitable number of ligands, depending on the metal and its oxidation state and depending on the precise structure of the ligand L, and thus to select the indices n and m suitably.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

The ligands may also be bonded to the metal via a carbene carbon atom. A cyclic carbene in the sense of this invention is a cyclic group which is bonded to the metal via a neutral C atom. The cyclic group here may be saturated or unsaturated. Preference is given here to Arduengo carbenes, i.e. carbenes in which two nitrogen atoms are bonded to the carbene C atom. A five-membered Arduengo carbene ring or another unsaturated five-membered carbene ring is likewise regarded as an aryl group in the sense of this invention.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkylene group or by a silylene group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, cyclohexyl, 2-methylpentyl, neohexyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the above-mentioned radicals R and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1), characterised in that they are uncharged, i.e. are electrically neutral. This is achieved in a simple manner by selecting the charges of the ligands L and L' in such a way that they compensate for the charge of the complexed metal atom M.

Preference is furthermore given to compounds of the formula (1), characterised in that the sum of the valence electrons around the metal atom is 16 in tri- and tetracoordinated complexes and 16 or 18 in pentacoordinated complexes and 18 in hexacoordinated complexes. This preference is due to the particular stability of these metal complexes.

Preference is given to compounds of the formula (1) in which M stands for a tetracoordinated, a pentacoordinated or a hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium and platinum. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(0), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V); particular preference is given to Mo(0), W(0), Re(I), Ru(II), Os(II), Rh(III) and Ir(III), where the above-mentioned metals have the coordination number 6, Pt(II), which has the coordination number 4, and Cu(I), which has the coordination number 3 or 4, in particular Ir(III) and Pt(II).

In a preferred embodiment of the invention, M is a tetracoordinated metal, and the index n stands for 1 or 2. If the index n=1, one bidentate or two monodentate ligands L', preferably one bidentate ligand L', are also coordinated to the metal M. If the index n=2, the index m=0.

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0.

The ligands L are bidentate ligands which are bonded to the metal M via a carbon atom and an exocyclic oxygen atom, sulfur atom or nitrogen atom.

The groups of the formula (3) or (4) can be bonded to the ligand L at any possible position. Preferred embodiments of the moiety of the formula (2) are therefore the structures of the following formulae (5) to (17),

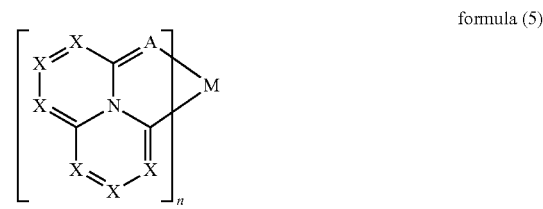

formula (5)

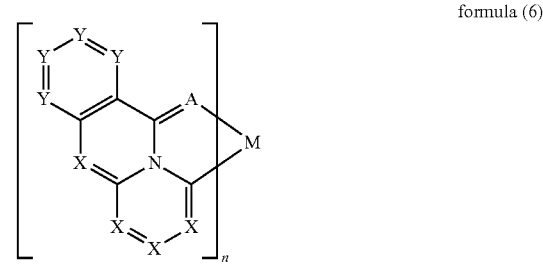

formula (6)

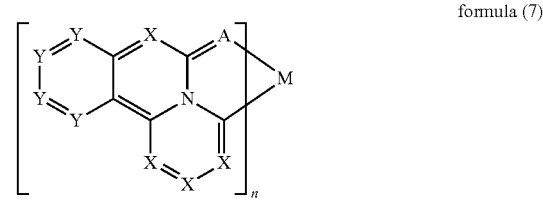

formula (7)

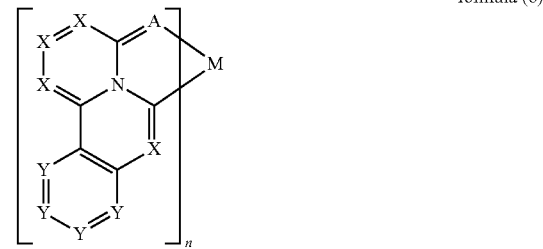

formula (8)

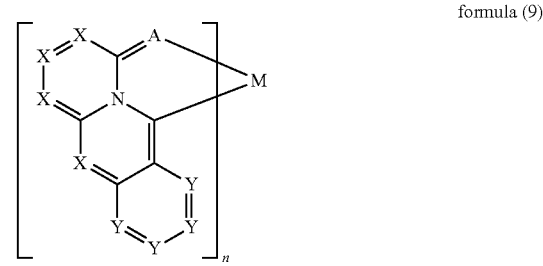

formula (9)

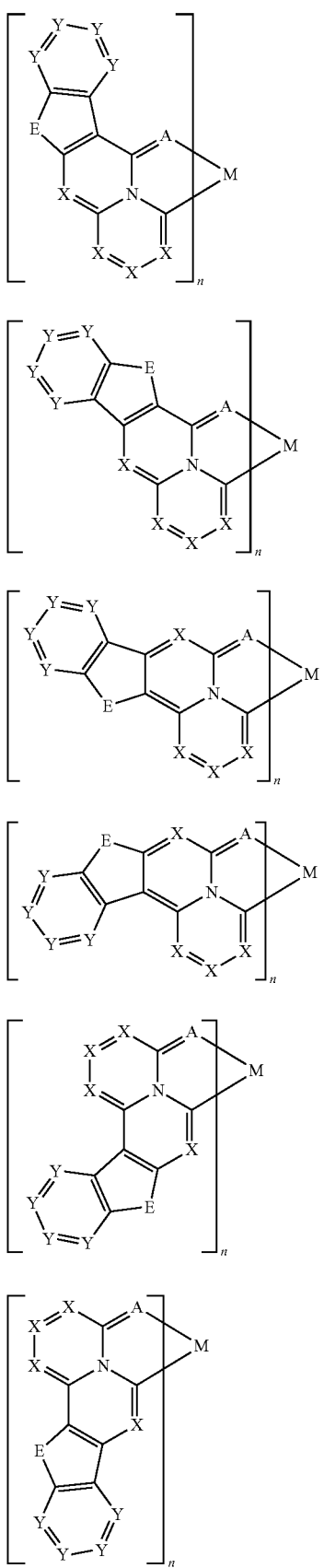

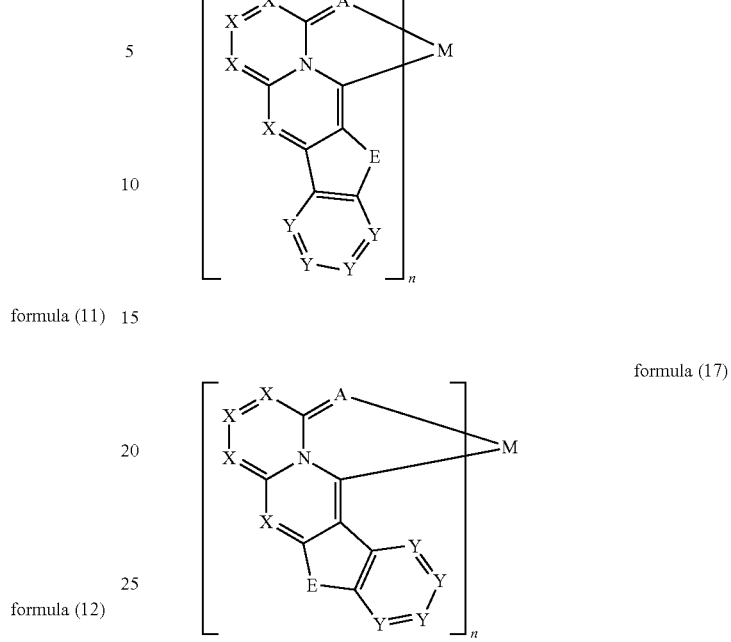

where X stands, identically or differently on each occurrence, for CR or N and the other symbols and indices have the meanings given above.

Particular preference is given to the structures of the formulae (5), (7) and (8) shown above.

In a preferred embodiment of the invention, a maximum of two groups X, particularly preferably a maximum of one group X per ring stand for nitrogen, and the other groups X in the ring stand for CR.

In a further preferred embodiment of the invention, a maximum of two groups Y, particularly preferably a maximum of one group Y, very particularly preferably no group Y per ring stand for nitrogen, and the other symbols Y in the ring stand for CR.

Very particularly preferably, a maximum of one group X and one group Y stand for N and the other groups X and Y stand for CR. Especially preferably, a maximum of one group X stands for CR and the other groups X and the groups Y stand for CR.

Preferred embodiments of the formulae (5), (7) and (8) are the structures of the following formulae (5a) to (5d), (7a) to (7c) and (8a) to (8c),

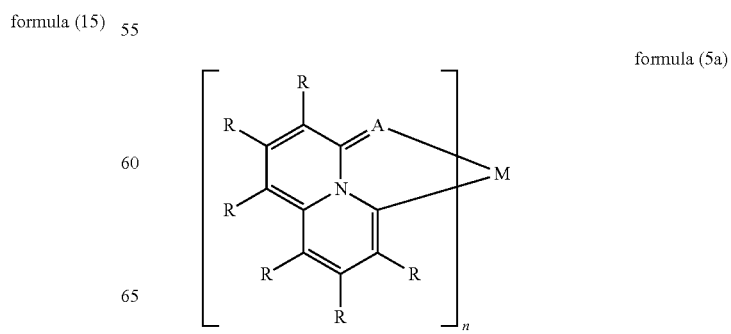

formula (5b)
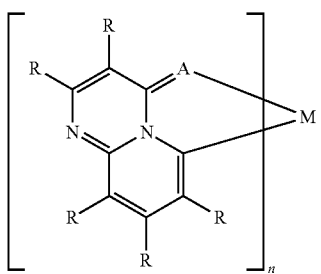

formula (5c)
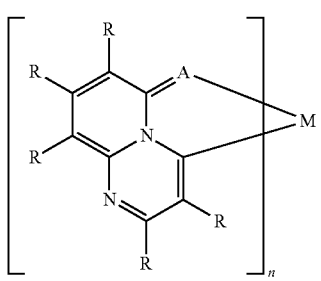

formula (5d)
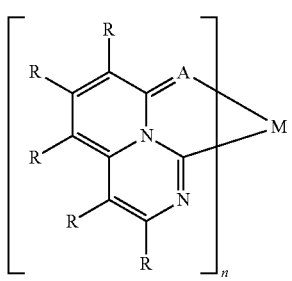

formula (7a)
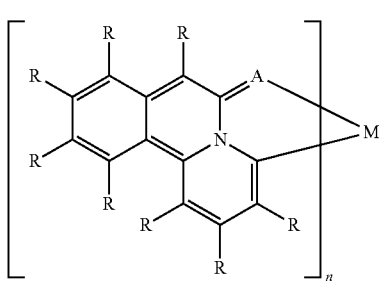

formula (7b)
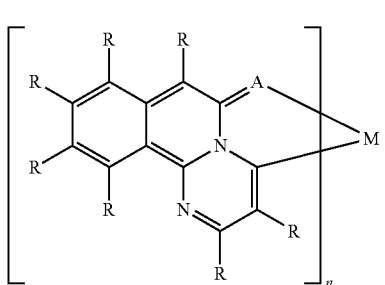

formula (7c)
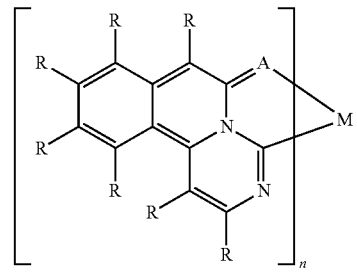

formula (8a)
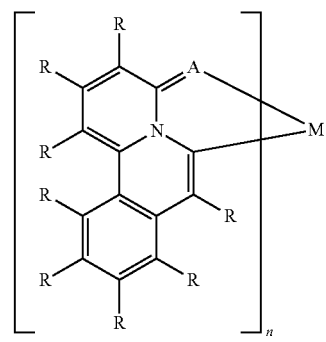

formula (8b)
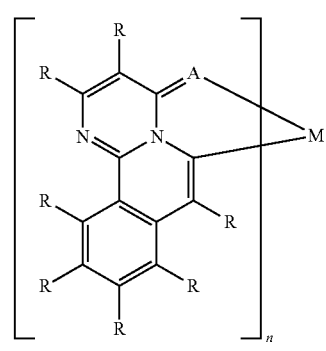

formula (8c)
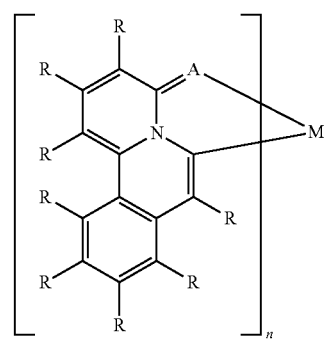

where the symbols and indices used have the meanings given above.

In a preferred embodiment of the invention, the coordinating group A in the moieties of the formulae (2) and (5) to (17) and the preferred embodiments stands for O or S, particularly preferably for O.

If one or more groups X and/or Y in the ligand L stand for N, it is preferred if at least one substituent R which is not equal to H or D, in particular a bulky substituent, is bonded adjacent to this N atom. This preference is due to the fact that the corresponding nitrogen atom is thereby sterically screened and is thus no longer available for coordination to the metal M. This results in more selective formation of the metal complexes according to the invention and thus in higher yields and greater purities.

Bulky substituents are, for example, alkyl groups, in particular branched and cyclic alkyl groups, alkoxy groups, substituted amino groups, aralkyl groups and aromatic and heteroaromatic ring systems, as are in each case defined above in the definition of R.

If this radical R stands for an alkyl group, this alkyl group then preferably has 3 to 10 C atoms, in particular 4 to 8 C atoms. It is furthermore preferably a secondary or tertiary alkyl group in which the secondary or tertiary C atom is either bonded directly to the ligand or is bonded to the ligand via a CH$_2$ group. This alkyl group is particularly preferably selected from the structures of the following formulae (R-1) to (R-33), where in each case the linking of these groups to the ligand is also drawn in:

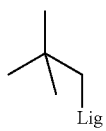 (R-1)

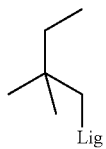 (R-2)

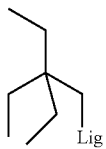 (R-3)

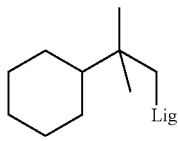 (R-4)

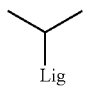 (R-5)

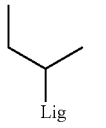 (R-6)

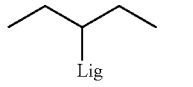 (R-7)

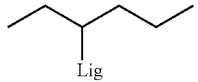 (R-8)

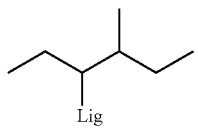 (R-9)

-continued

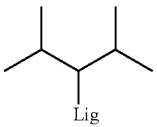 (R-10)

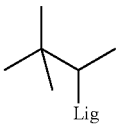 (R-11)

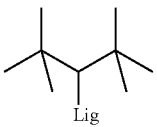 (R-12)

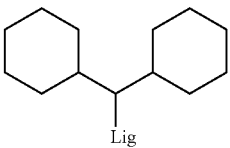 (R-13)

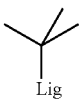 (R-14)

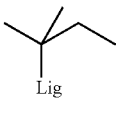 (R-15)

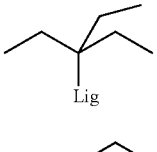 (R-16)

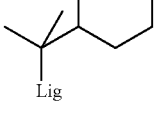 (R-17)

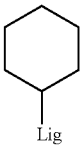 (R-18)

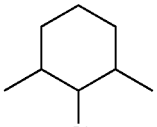 (R-19)

(R-20)

(R-21) 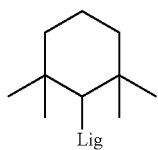
(R-22) 
(R-23) 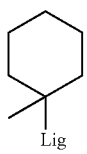
(R-24) 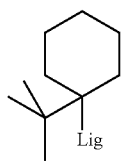
(R-25) 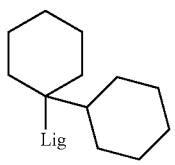
(R-26) 
(R-27) 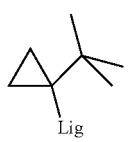
(R-28) 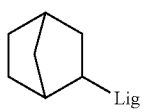
(R-29) 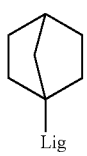
(R-30) 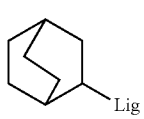
(R-31) 
(R-32) 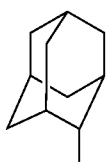
(R-33) 
where Lig denotes the linking of the alkyl group to the ligand.
If R stands for an alkoxy group, this alkoxy group then preferably has 3 to 10 C atoms. This alkoxy group is preferably selected from the structures of the following formulae (R-34) to (R-47), where in each case the linking of these groups to the ligand is also drawn in:
(R-34) 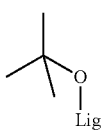
(R-35) 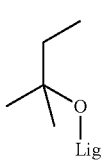
(R-36) 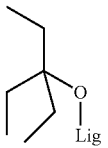
(R-37) 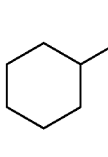
(R-38) 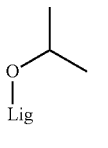
(R-39) 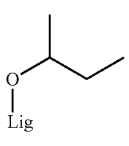

-continued

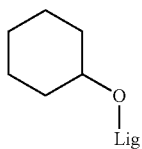 (R-40)

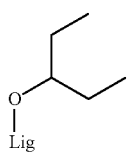 (R-41)

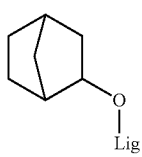 (R-42)

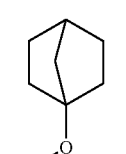 (R-43)

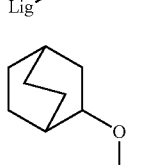 (R-44)

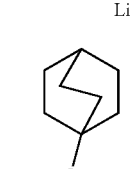 (R-45)

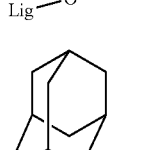 (R-46)

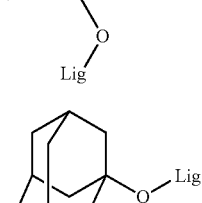 (R-47)

 (R-48)

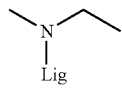 (R-49)

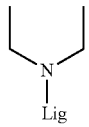 (R-50)

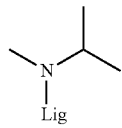 (R-51)

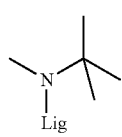 (R-52)

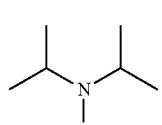 (R-53)

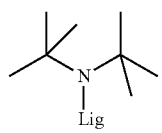 (R-54)

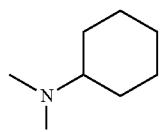 (R-55)

where Lig denotes the linking of the alkyl group to the ligand.

If R stands for an aralkyl group, this aralkyl group is then preferably selected from the structures of the following formulae (R-56) to (R-69), where in each case the linking of these groups to the ligand is also drawn in:

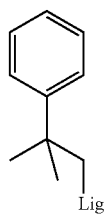 (R-56)

where Lig denotes the linking of the alkyl group to the ligand.

If R stands for a dialkylamino group, each of these alkyl groups then preferably has 1 to 8 C atoms, particularly preferably 1 to 6 C atoms. Examples of suitable alkyl groups are methyl, ethyl or the structures mentioned above as (R-1) to (R-33) groups. The dialkylamino group is particularly preferably selected from the structures of the following formulae (R-48) to (R-55), where in each case the linking of these groups to the ligand is also drawn in:

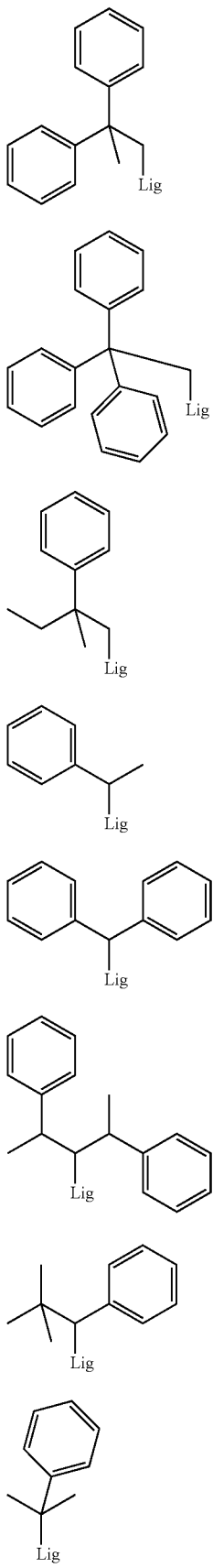
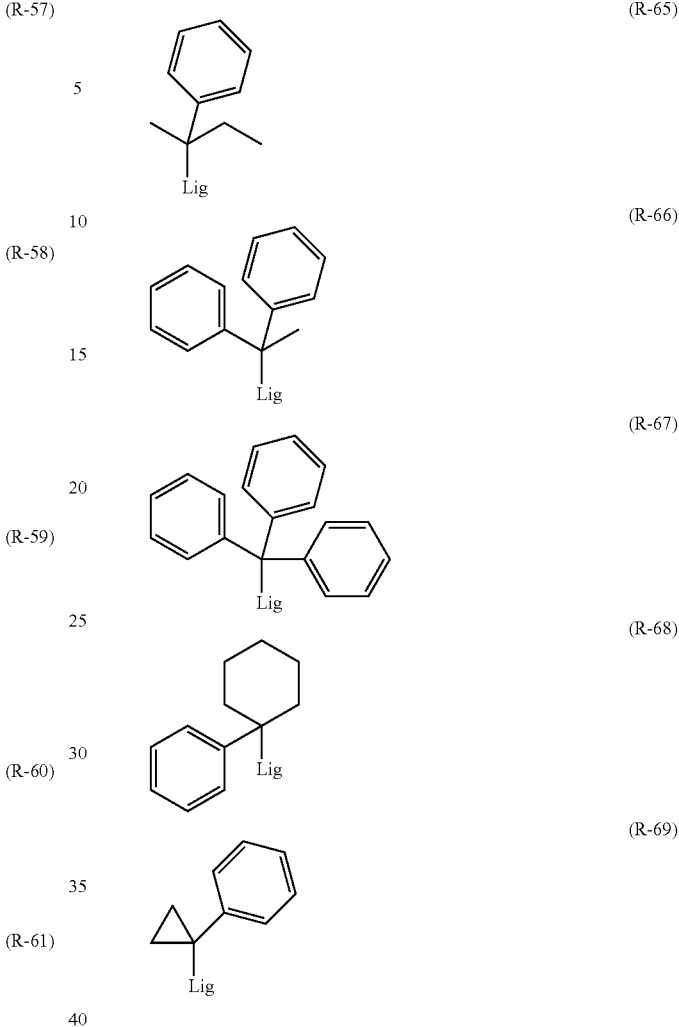

where Lig denotes the linking of the aralkyl group to the ligand and the phenyl groups may each be substituted by one or more radicals $R^1$.

The alkyl, alkoxy, dialkylamino and aralkyl groups may, depending on the precise structure, also have one or more stereocentres. Since the basic structure of the complex may also be a chiral structure, the formation of diastereomers is possible, in particular also if a plurality of such alkyl, alkoxy, dialkylamino and aralkyl groups having stereocentres are present. The complexes according to the invention then encompass both the mixtures of the various diastereomers or the corresponding racemates and also the individual isolated diastereomers or enantiomers.

If R stands for an aromatic or heteroaromatic ring system, this aromatic or heteroaromatic ring system then preferably has 5 to 30 aromatic ring atoms, particularly preferably 5 to 24 aromatic ring atoms. Furthermore, this aromatic or heteroaromatic ring system preferably contains no aryl or heteroaryl groups in which more than two aromatic six-membered rings are condensed directly onto one another. The aromatic or heteroaromatic ring system particularly preferably contains no condensed aryl or heteroaryl groups at all, and it very particularly preferably contains only phenyl groups. The aromatic ring system here is preferably selected from the structures of the following formulae (R-70) to (R-84), where in each case the linking of these groups to the ligand is also drawn in:

(R-70) 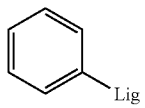
(R-71) 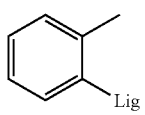
(R-72) 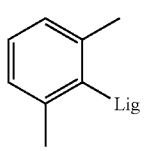
(R-73) 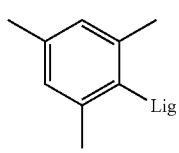
(R-74) 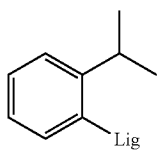
(R-75) 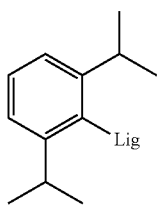
(R-76) 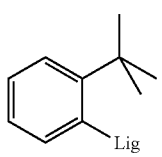
(R-77) 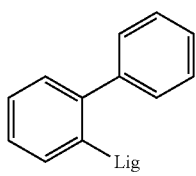
(R-78) 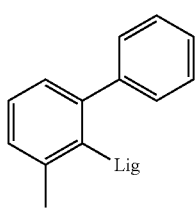
(R-79) 
(R-80) 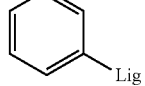
(R-81) 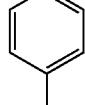
(R-82) 
(R-83) 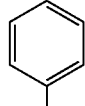

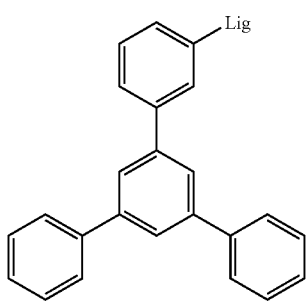
(R-84)

where Lig denotes the linking of the aromatic or heteroaromatic ring system to the ligand and the phenyl groups may each be substituted by one or more radicals $R^1$.

Furthermore, the heteroaromatic ring system is preferably selected from the structures of the following formulae (R-85) to (R-112), where in each case the linking of these groups to the ligand is also drawn in:

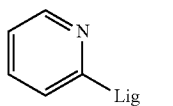
(R-85)

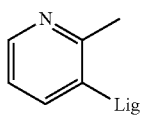
(R-86)

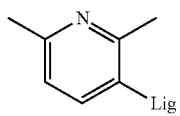
(R-87)

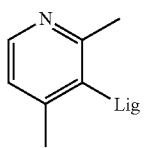
(R-88)

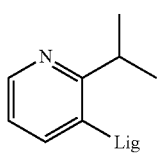
(R-89)

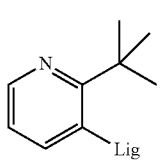
(R-90)

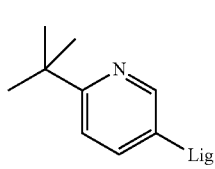
(R-91)

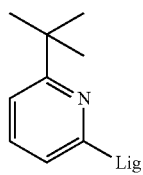
(R-92)

(R-93)

(R-94)

(R-95)

(R-96)

(R-97)

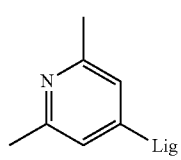
(R-98)

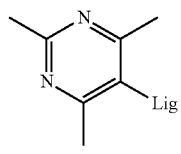
(R-99)

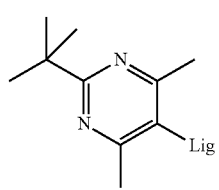

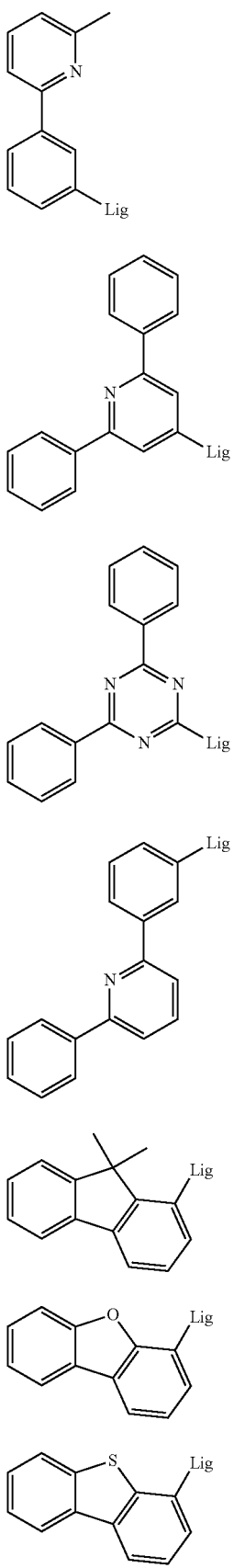
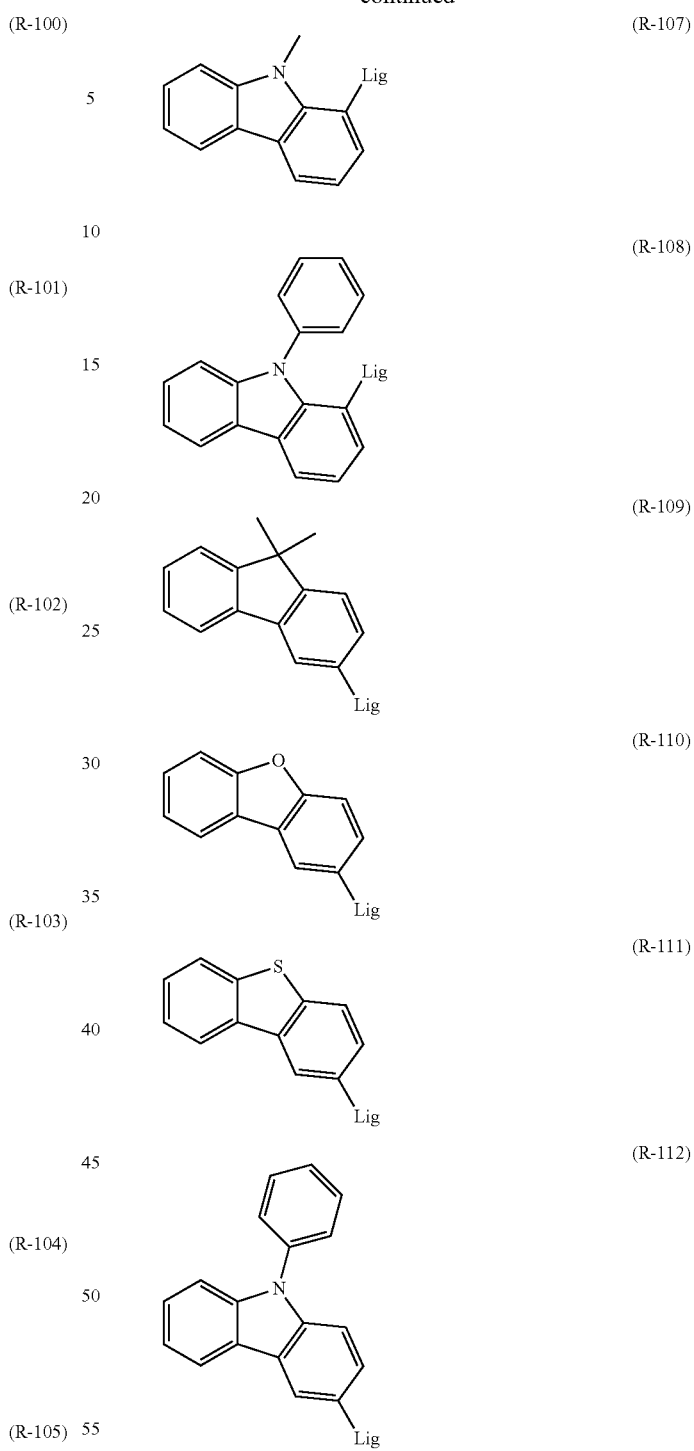

where Lig denotes the linking of the aromatic or heteroaromatic ring system to the ligand and the aromatic and heteroaromatic groups may each be substituted by one or more radicals $R^1$.

Furthermore, it may be preferred for the ligand L to have two adjacent carbon atoms, each of which are substituted by radicals R, where the respective radicals R, together with the C atoms, form a ring of the following formula (18), (19), (20) or (20a) to (20d), formula (18)
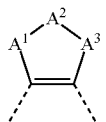

formula (19)
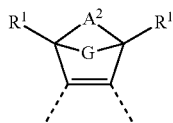

formula (20)
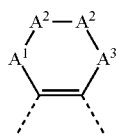

formula (20a)
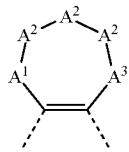

formula (20b)
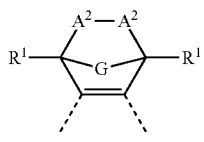

formula (20c)
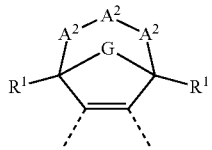

formula (20d)
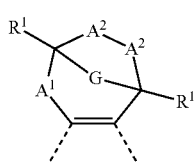

where $R^1$ and $R^2$ have the meanings given above, the dashed bonds indicate the linking of the two carbon atoms in the ligand and furthermore:

$A^1$, $A^3$ is, identically or differently on each occurrence, $C(R^3)_2$, O, S, $NR^3$ or C(=O);

$A^2$ is, identically or differently on each occurrence, $C(R^1)_2$, O, S, $NR^3$ or C(=O);

or two adjacent groups $A^2$ together in formula (20) stand for a group of the following formula (21) or (22), formula (21)
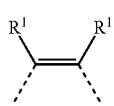

formula (22)
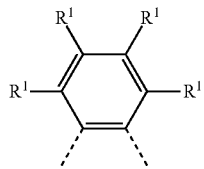

G is an alkylene group having 1, 2 or 3 C atoms, which may be substituted by one or more radicals $R^2$, —$CR^2$=$CR^2$— or an ortho-linked arylene or heteroarylene group having 5 to 14 aromatic ring atoms, which may be substituted by one or more radicals $R^2$;

$R^3$ is, identically or differently on each occurrence, F, a straight-chain alkyl or alkoxy group having 1 to 20 C atoms, a branched or cyclic alkyl or alkoxy group having 3 to 20 C atoms, each of which may be substituted by one or more radicals $R^2$, where one or more non-adjacent $CH_2$ groups may be replaced by $R^2C$=$CR^2$, C≡C, $Si(R^2)_2$, C=O, $NR^2$, O, S or $CONR^2$ and where one or more H atoms may be replaced by D or F, or an aromatic or heteroaromatic ring system having 5 to 24 aromatic ring atoms, which may in each case be substituted by one or more radicals $R^2$, or an aryloxy or heteroaryloxy group having 5 to 24 aromatic ring atoms, which may be substituted by one or more radicals $R^2$, or an aralkyl or heteroaralkyl group having 5 to 24 aromatic ring atoms, which may be substituted by one or more radicals $R^2$; two radicals $R^3$ here may form an aliphatic or aromatic ring system with one another; furthermore, $R^3$ may form an aliphatic ring system with an adjacent radical R or $R^1$;

with the proviso that no two heteroatoms in $A^1$-$A^2$-$A^3$ $A^1$-$(A^2)_2$-$A^3$ $A^1$-$(A^2)_3$-$A^3$ are bonded directly to one another.

If two radicals $R^3$ which are bonded to the same carbon atom form a ring system with one another, a spiro system forms.

The groups of the formula (18), (19), (20) or (20a) to (20d) are also preferred groups if they are bonded adjacent to an N atom in the ligand.

It is essential in the groups of the formulae (18), (19), (20) and (20a) to (20d) that they contain no acidic benzylic protons. Benzylic protons are taken to mean protons which are bonded to a carbon atom which are bonded directly to the heteroaromatic ligand. The absence of acidic benzylic protons is achieved in formula (18), (20) and (20a) through $A^1$ and $A^3$, if they stand for $C(R^3)_2$, being defined in such a way that $R^3$ is not equal to hydrogen. The absence of acidic benzylic protons is automatically achieved in formula (19), (20b) and (20c) through it being a bicyclic structure. Owing to the rigid spatial arrangement, $R^1$, if it stands for H, is significantly less acidic than benzylic protons, since the corresponding anion of the bicyclic structure is not mesomerism-stabilised. Even if $R^1$ in formula (19), (20b), (20c) and (20d) stands for H, it is a non-acidic proton in the sense of the present application.

In a preferred embodiment of the structure of the formula (18), a maximum of one of the groups $A^1$, $A^2$ and $A^3$ stands for a heteroatom, in particular for O or $NR^3$, and the other two groups stand for $C(R^3)_2$ or $C(R^1)_2$ or $A^1$ and $A^3$ stand, identically or differently on each occurrence, for O or $NR^3$ and $A^2$ stands for $C(R^1)_2$. In a particularly preferred embodiment of the invention, $A^1$ and $A^3$ stand, identically or differently on each occurrence, for $C(R^3)_2$ and $A^2$ stands for $C(R^1)_2$ and particularly preferably for $C(R^3)_2$. Preferred embodiments of the formula (18) are thus the structures of the formula (18-A), (18-B), (18-C) and (18-D), and a particularly preferred embodiment of the formula (18-A) is the structure of the formula (18-E),

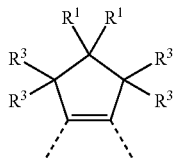

formula (18-A)

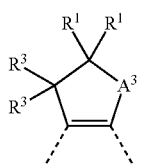

formula (18-B)

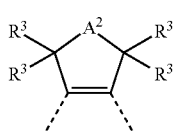

formula (18-C)

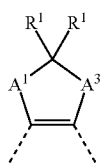

formula (18-D)

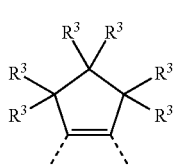

formula (18-E)

where $R^1$ and $R^3$ have the meanings given above and $A^1$, $A^2$ and $A^3$ stands, identically or differently on each occurrence, for O or $NR^3$.

In a preferred embodiment of the structure of the formula (19), the radicals $R^1$ which are bonded to the bridgehead stand for H, D, F or $CH_3$. Furthermore, $A^2$ preferably stands for $C(R^1)_2$ or O, and particularly preferably for $C(R^3)_2$. Preferred embodiments of the formula (19) are thus a structures of the formula (19-A) and (19-B), and a particularly preferred embodiment of the formula (19-A) is a structure of the formula (19-C),

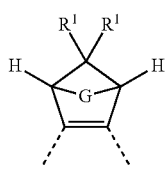

formula (19-A)

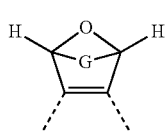

formula (19-B)

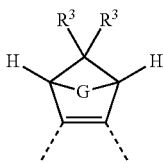

formula (19-C)

where the symbols used have the meanings given above.

Furthermore preferably, the group G in the formulae (19), (19-A), (19-B) and (19-C) stands for an ethylene group, which may be substituted by one or more radicals $R^2$, where $R^2$ preferably stands, identically or differently on each occurrence, for H or an alkyl group having 1 to 4 C atoms, i.e. a group —$C(R^2)_2$—$C(R^2)_2$—, or an ortho-arylene group having 6 to 10 C atoms, which may be substituted by one or more radicals $R^2$, but is preferably unsubstituted, in particular an ortho-phenylene group, which may be substituted by one or more radicals $R^2$, but is preferably unsubstituted.

In a preferred embodiment of the structure of the formula (20), a maximum of one of the groups $A^1$, $A^2$ and $A^3$ stands for a heteroatom, in particular for O or $NR^3$, and the other groups stand for $C(R^3)_2$ or $C(R^1)_2$ or $A^1$ and $A^3$ stand, identically or differently on each occurrence, for O or $NR^3$ and $A^2$ stands, identically or differently on each occurrence, for $C(R^1)_2$. In a particularly preferred embodiment of the invention, $A^1$ and $A^3$ stand, identically or differently on each occurrence, for $C(R^3)_2$ and $A^2$ stands, identically or differently on each occurrence, for $C(R^1)_2$ and particularly preferably for $C(R^3)_2$. Preferred embodiments of the formula (20) are thus the structures of the formula (20-A) to (20-J),

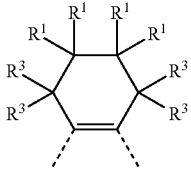

formula (20-A)

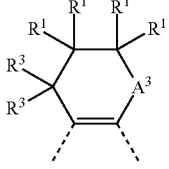

formula (20-B)

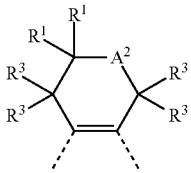

formula (20-C)

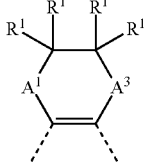

formula (20-D)

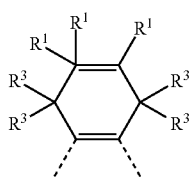 formula (20-E)

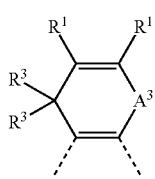 formula (20-F)

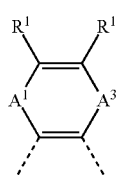 formula (20-G)

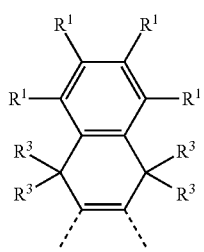 formula (20-H)

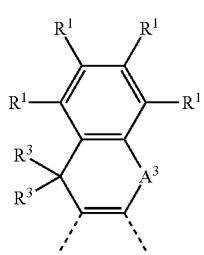 formula (20-I)

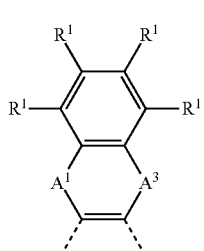 formula (20-J)

where $R^1$ and $R^3$ have the meanings given above and $A^1$, $A^2$ and $A^3$ stands, identically or differently on each occurrence, for O or $NR^3$.

Preferred embodiments of the formula (20a) are the structures of the following formulae (20a-A) to (20a-E),

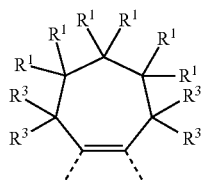 formula (20a-A)

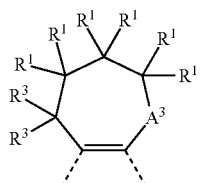 formula (20a-B)

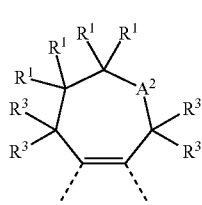 formula (20a-C)

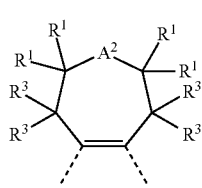 formula (20a-D)

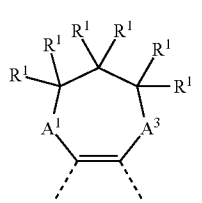 formula (20a-E)

where $R^1$ and $R^3$ have the meanings given above and $A^1$, $A^2$ and $A^3$ stands, identically or differently on each occurrence, for O or $NR^3$.

In a preferred embodiment of the structure of the formula (20b), (20c) and (20d), the radicals $R^1$ which are bonded to the bridgehead stand for H, D, F or $CH_3$ particularly preferably for H. Furthermore preferably, $A^2$ stands for $C(R^1)_2$. Preferred embodiments of the formula (20b), (20c) and (20d) are thus the structures of the formulae (20b-A), (20c-A) and (20d-A),

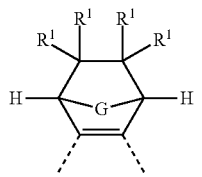 formula (20b-A)

formula (20c-A)

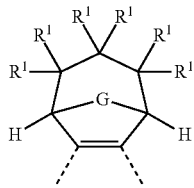

formula (20d-A)

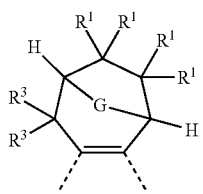

where the symbols used have the meanings given above.

In a further preferred embodiment of the invention, $R^3$ in the groups of the formula (18), (19), (20) and (20a) to (20d) and in the preferred embodiments stands, identically or differently on each occurrence, for F, a straight-chain alkyl group having 1 to 10 C atoms or a branched or cyclic alkyl group having 3 to 20 C atoms, where in each case one or more non-adjacent $CH_2$ groups may be replaced by $R^2C{=}CR^2$ and one or more H atoms may be replaced by D or F, or an aromatic or heteroaromatic ring system having 5 to 14 aromatic ring atoms, which may in each case be substituted by one or more radicals $R^2$; two radicals $R^3$ here which are bonded to the same carbon atom may form an aliphatic or aromatic ring system with one another and thus form a spiro system; furthermore, $R^3$ may form an aliphatic ring system with an adjacent radical R or $R^1$.

In a particularly preferred embodiment of the invention, $R^3$ in the groups of the formulae (18), (19), (20) and (20a) to (20d) and in the preferred embodiments stands, identically or differently on each occurrence, for F, a straight-chain alkyl group having 1 to 3 C atoms, in particular methyl, or an aromatic or heteroaromatic ring system having 5 to 12 aromatic ring atoms, which may in each case be substituted by one or more radicals $R^2$, but is preferably unsubstituted; two radicals $R^3$ here which are bonded to the same carbon atom may form an aliphatic or aromatic ring system with one another and thus form a spiro system; furthermore, $R^3$ may form an aliphatic ring system with an adjacent radical R or $R^1$.

Examples of particularly suitable groups of the formula (18) are the groups (18-1) to (18-69) shown below:

(18-1)

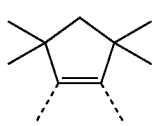

(18-2)

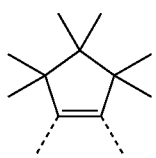

(18-3)

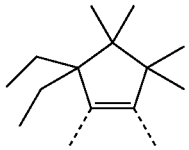

(18-4)

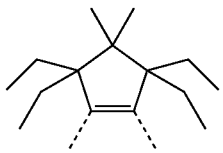

(18-5)

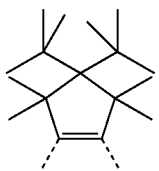

(18-6)

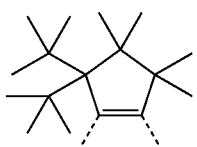

(18-7)

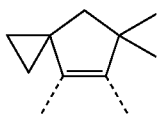

(18-8)

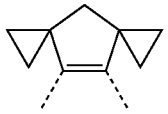

(18-9)

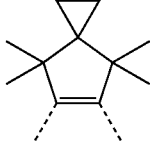

(18-10)

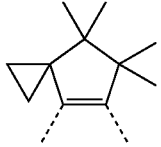

(18-11)

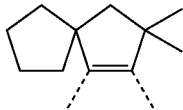

(18-12)

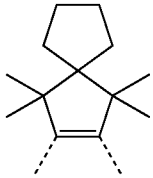

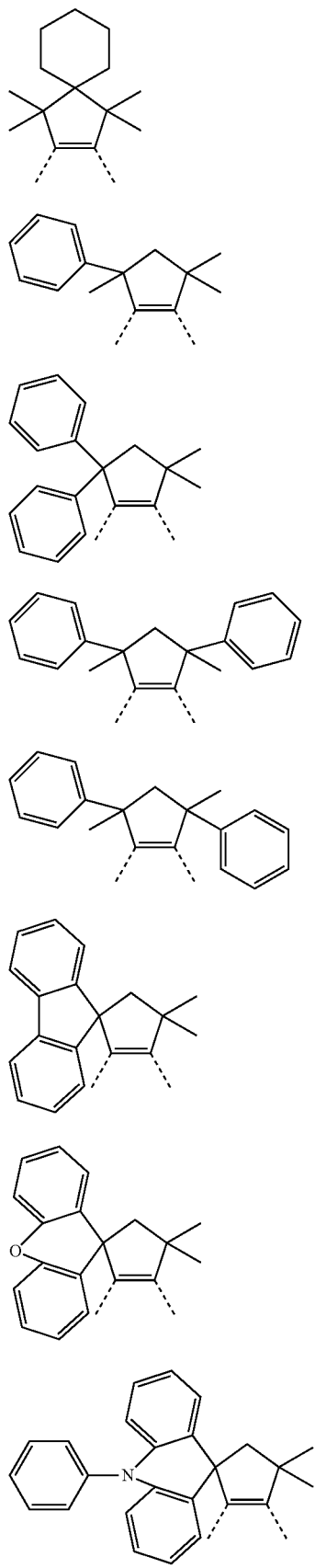
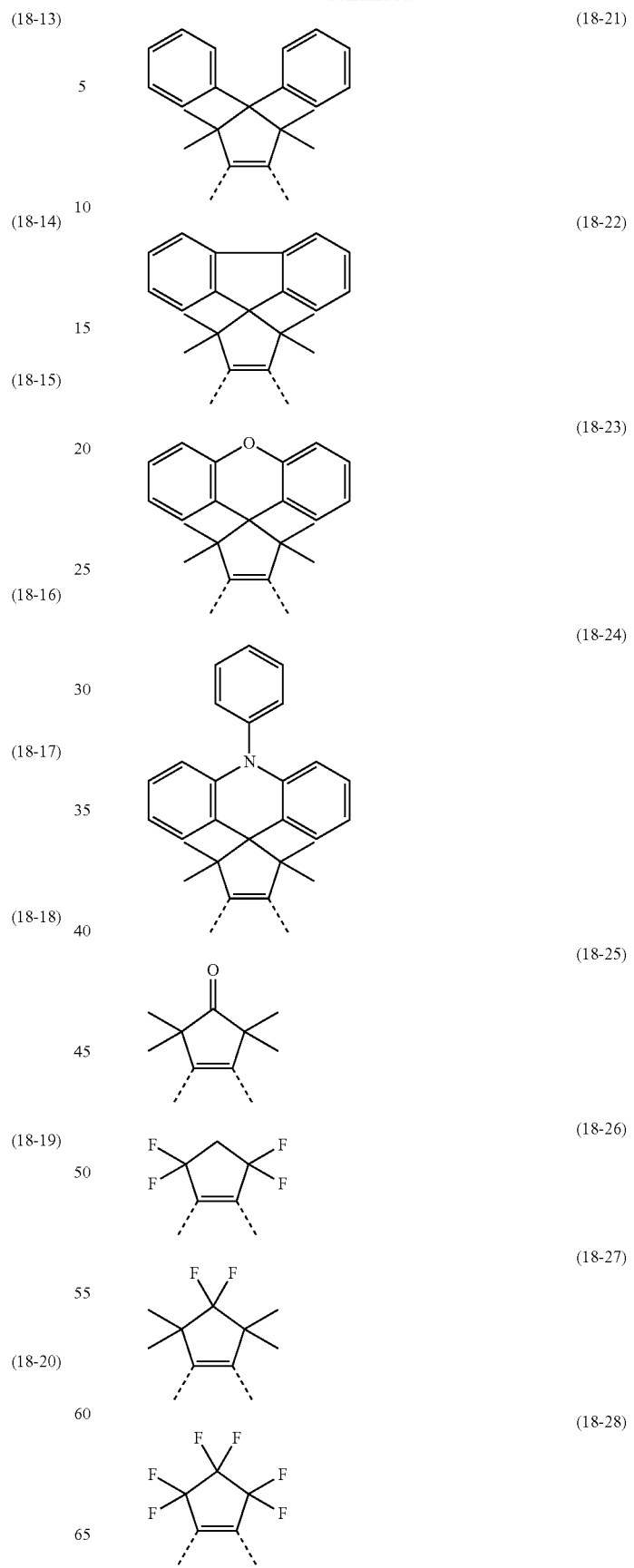

-continued
(18-29) 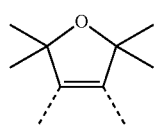
(18-30) 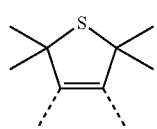
(18-31) 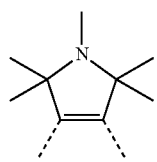
(18-32) 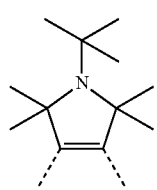
(18-33) 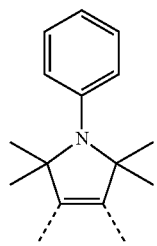
(18-34) 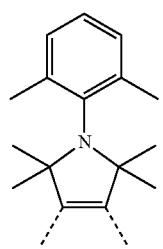
(18-35) 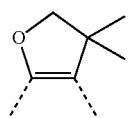
(18-36) 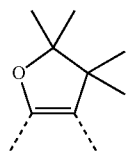
(18-37) 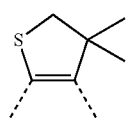
-continued
(18-38) 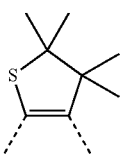
(18-39) 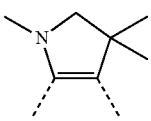
(18-40) 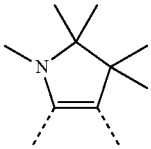
(18-41) 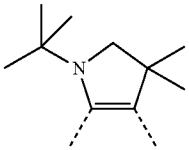
(18-42) 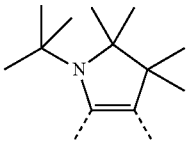
(18-43) 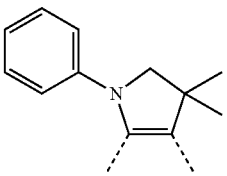
(18-44) 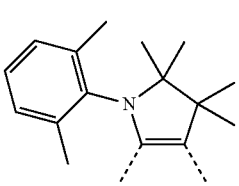
(18-45) 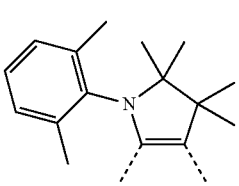
(18-46) 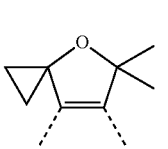
(18-47) 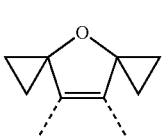

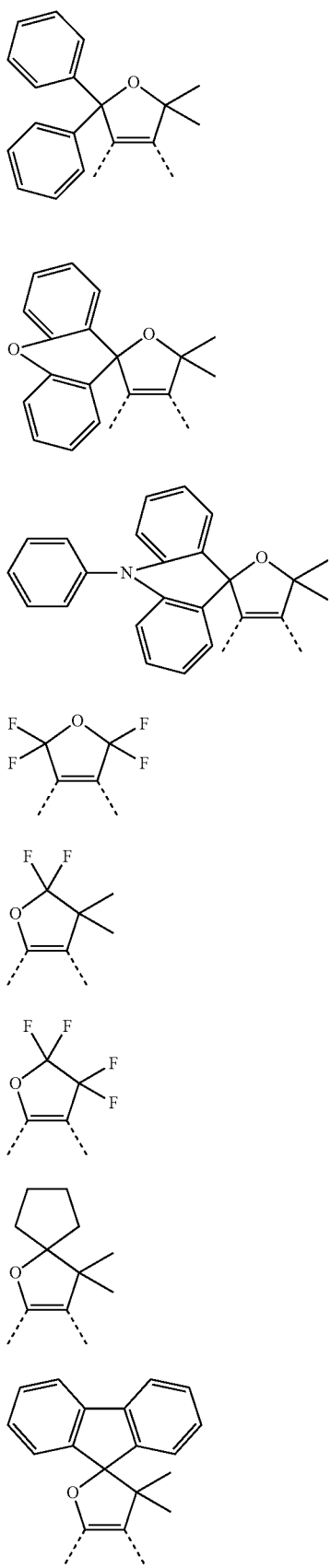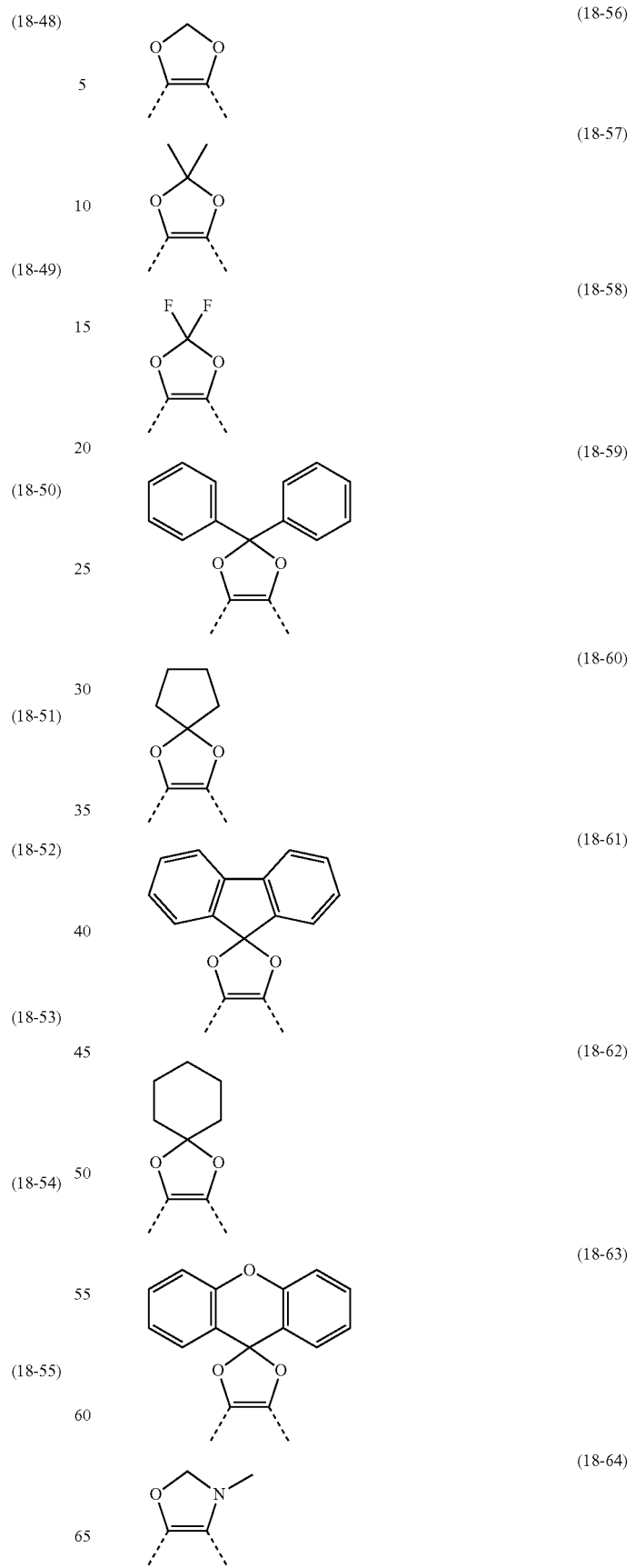

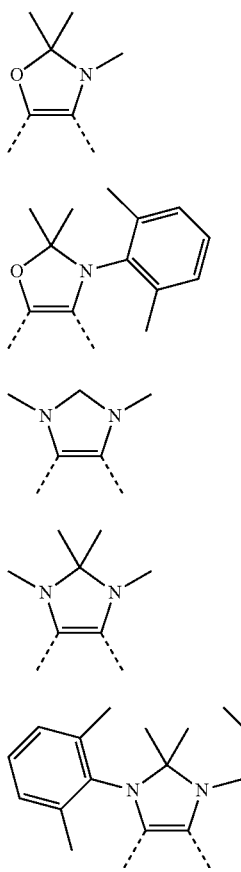
Examples of particularly suitable groups of the formula (19) are the groups (19-1) to (19-21) shown below:
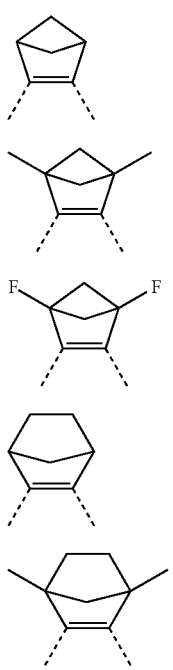
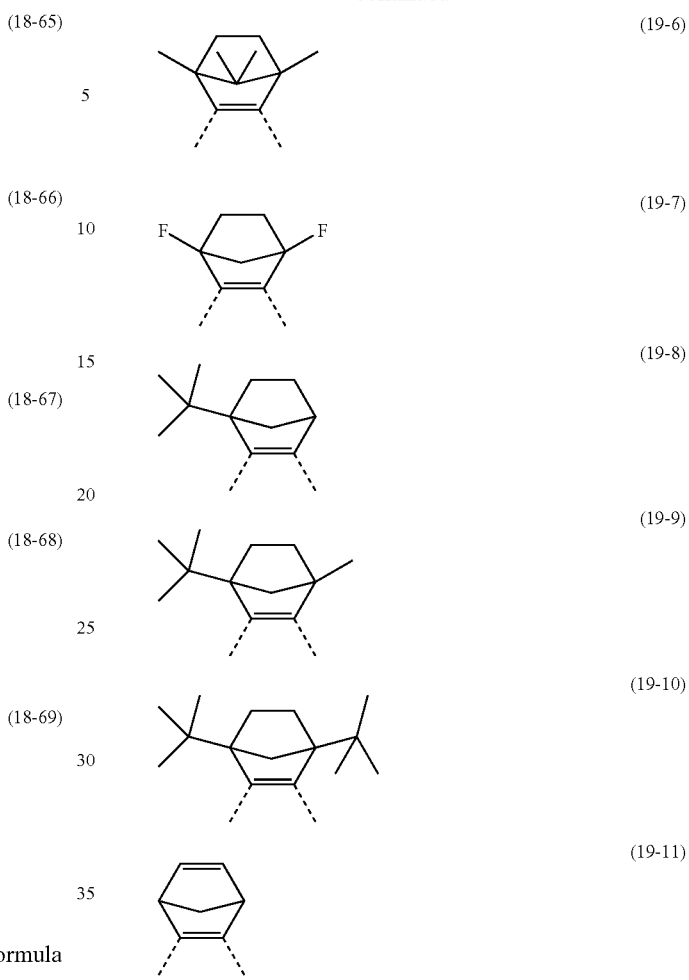
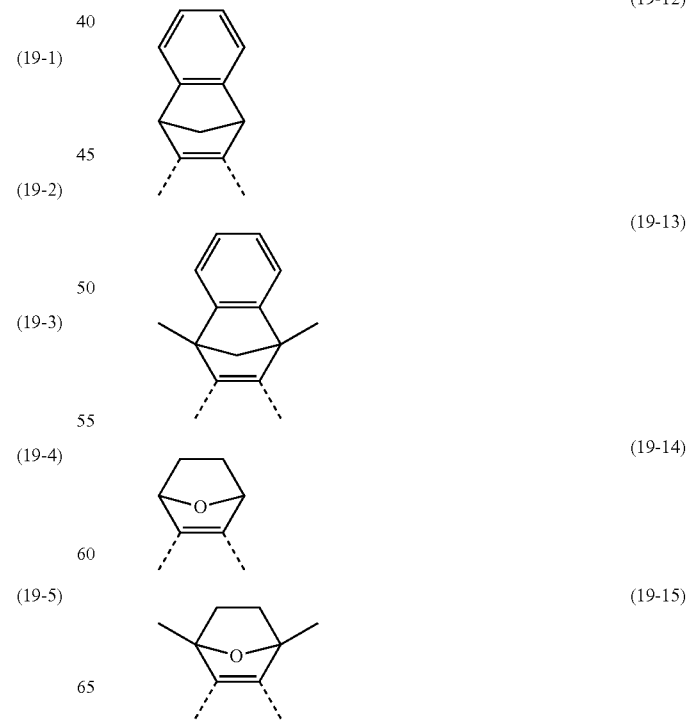

(19-16)
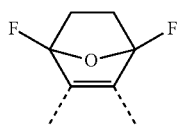
(19-17)
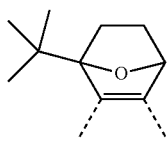
(19-18)
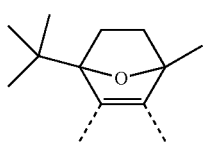
(19-19)
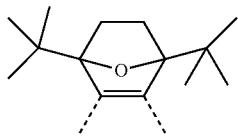
(19-20)
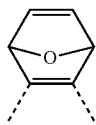
(19-21)
Examples of particularly suitable groups of the formula (20) are the groups (20-1) to (20-30) shown below:
(20-1)
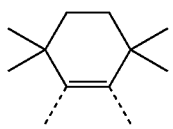
(20-2)
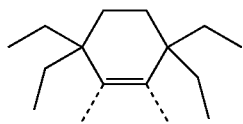
(20-3)
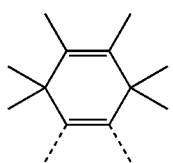
(20-4)
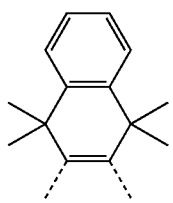
(20-5)
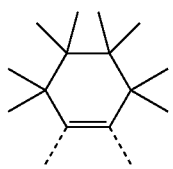
(20-6)
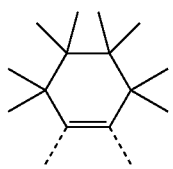
(20-7)
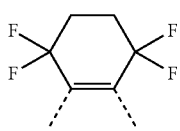
(20-8)
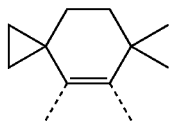
(20-9)
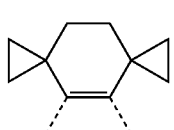
(20-10)
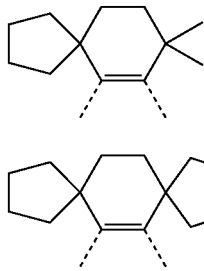
(20-11)
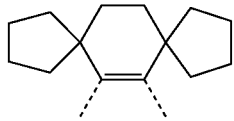
(20-12)
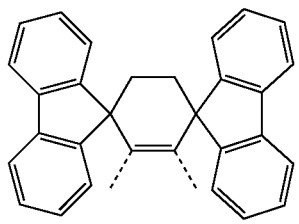
(20-13)
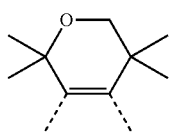

(20-14) 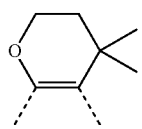
(20-15) 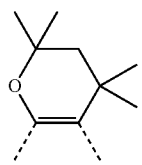
(20-16) 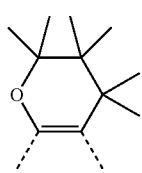
(20-17) 
(20-18) 
(20-19) 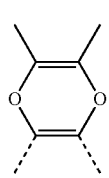
(20-20) 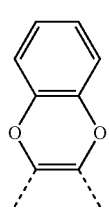
(20-21) 
(20-22) 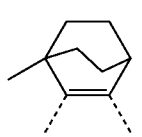
(20-23) 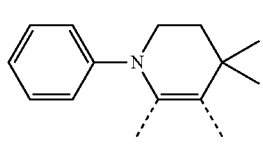
(20-24) 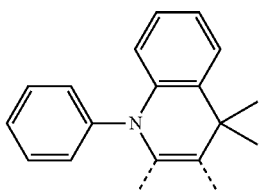
(20-25) 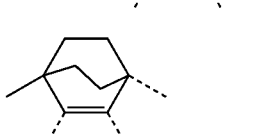
(20-26) 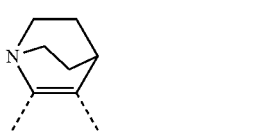
(20-27) 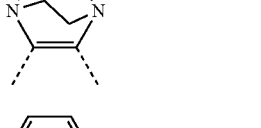
(20-28) 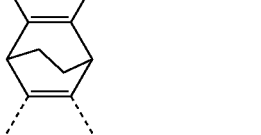
(20-29) 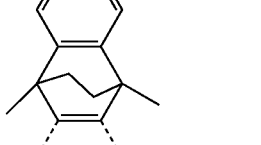
(20-30) 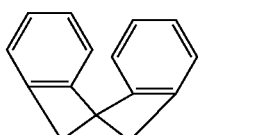
Examples of particularly suitable groups of the formula (20a), (20c) and (20d) are the groups shown below:
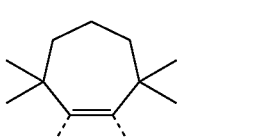
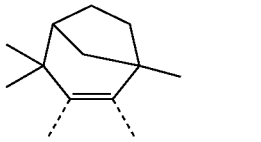

-continued

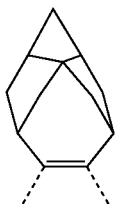

If further or other radicals R which do not correspond to the above-mentioned radicals are bonded in the moiety of the formula (2), these radicals R are preferably selected on each occurrence, identically or differently, from the group consisting of H, D, F, Br, I, $N(R^1)_2$, CN, $Si(R^1)_3$, $B(OR^1)_2$, $C(=O)R^1$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^1$, where one or more H atoms may be replaced by D or F, or an aromatic or heteroaromatic ring system having 5 to 30 aromatic ring atoms, which may in each case be substituted by one or more radicals $R^1$; two adjacent radical R here or R with $R^1$ may also form a mono- or polycyclic, aliphatic or aromatic ring system with one another. These radicals R are particularly preferably selected on each occurrence, identically or differently, from the group consisting of H, D, F, $N(R^1)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^1$; two adjacent radicals R here or R with $R^1$ may also form a mono- or polycyclic, aliphatic or aromatic ring system with one another.

It is furthermore possible for one or the substituents R in the moieties of the formula (2) or (5) to (17) to represent a coordinating group which is likewise coordinated to the metal M. Preferred coordinating groups R are aryl or heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides. The moieties $M(L)_n$ of the following formula (23), for example, are accessible here:

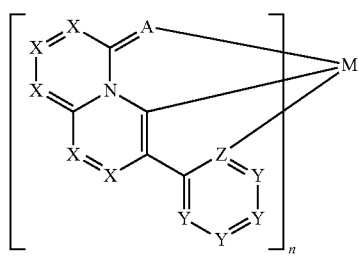

formula (23)

where the symbols and indices used have the meanings given above and Z stands or C or N. Further structures having tridentate or tetradentate ligands are also possible entirely analogously to these structures.

As described above, a bridging unit V which links this ligand L to one or more further ligands L or L' may also be present instead of one of the radicals R in formula (2). In a preferred embodiment of the invention, a single bond or a bridging unit V is present instead of one of the radicals R, so that the ligands have a tridentate or polydentate or polypodal character. It is also possible for two such bridging units V to be present. This results in the formation of macrocyclic ligands or in the formation of cryptates.

Preferred structures containing polydentate ligands are the metal complexes of the following formulae (24) to (28),

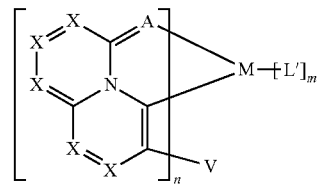

formula (24)

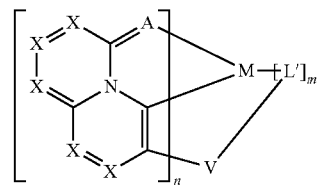

formula (25)

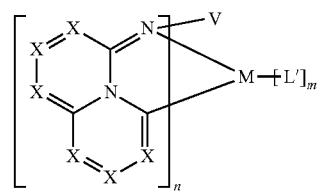

formula (26)

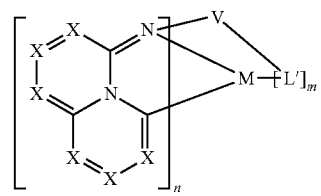

formula (27)

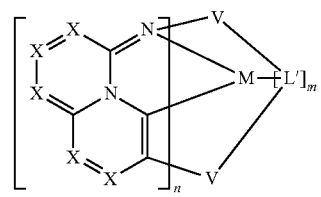

formula (28)

where the symbols used have the meanings given above, where n in the formulae (24), m (26) and (28) is 2 or 3 and V preferably represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or L to L' to one another. The bridging unit V here may also be substituted by one or more radicals $R^1$. Furthermore, the bridging unit V may have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged. The charge of V is preferably selected so that overall a neutral complex forms.

If V bridges three ligands L to one another or two ligands L to L' or one ligand L to two ligands L', V is preferably selected, identically or differently on each occurrence, from the group consisting of B, $B(R^1)^-$, $B(C(R^1)_2)_3$, $(R^1)B(C(R^1)_2)_3^-$, $B(O)_3$, $(R^1)B(O)_3$, $B(C(R^1)_2C(R^1)_2)_3$, $(R^1)B(C(R^1)_2C(R^1)_2)_3$, $B(C(R^1)_2O)_3$, $(R^1)B(C(R^1)_2O)^-$, $B(OC(R^1)_2)_3$, $(R^1)B(OC(R^1)_2)_3$, $C(R^1)$, $CO^-$, $CN(R^1)_2$, $(R^1)C(C(R^1)_2)_3$, $(R^1)C(O)_3$, $(R^1)C(C(R^1)_2C(R^1)_2)_3$, $(R^1)C(C(R^1)_2O)_3$, $(R^1)C(OC(R^1)_2)_3$, $(R^1)C(Si(R^1)_2)_3$, $(R^1)C(Si(R^1)_2C(R^1)_2)_3$, $(R^1)C(C(R^1)_2Si(R^1)_2)_3$, $(R^1)C(Si(R^1)_2Si(R^1)_2)_3$, $Si(R^1)$, $(R^1)Si(C(R^1)_2)_3$, $(R^1)Si(O)_3$, $(R^1)Si(C(R^1)_2C(R^1)_2)_3$, $(R^1)Si(OC(R^1)_2)_3$, $(R^1)Si(C(R^1)_2O)_3$, $(R^1)Si(Si(R^1)_2)_3$, $(R^1)Si(Si(R^1)_2C(R^1)_2)_3$, $(R^1)Si(C(R^1)_2Si(R^1)_2)_3$, $(R^1)Si(Si(R^1)_2Si(R^1)_2)_3$, N, NO, $N(R^1)^+$, $N(C(R^1)_2)_3$, $(R^1)N(C(R^1)_2)_3^+$, $N(C=O)_3$, $N(C(R^1)_2C(R^1)_2)_3$, $(R^1)N(C(R^1)_2C(R^1)_2)^+$, P, $P(R^1)^+$, PO, PS, PSe, PTe, $P(O)_3$, $PO(O)_3$, $P(OC(R^1)_2)_3$, $PO(OC(R^1)_2)_3$, $P(C(R^1)_2)_3$, $P(R^1)(C(R^1)_2)_3$, $PO(C(R^1)_2)_3$, $P(C(R^1)_2C(R^1)_2)_3$, $P(R^1)(C(R^1)_2C(R^1)_2)_3^+$, $PO(C(R^1)_2C(R^1)_2)_3$, $S^+$, $S(C(R^1)_2)_3$, $S(C(R^1)_2C(R^1)_2)_3^+$, or a unit of the formula (29), (30), (31) or (32),

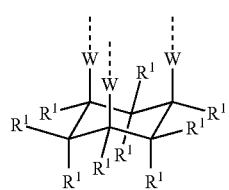

formula (29)

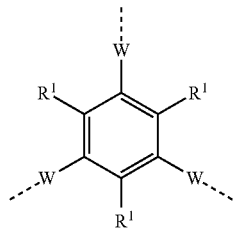

formula (30)

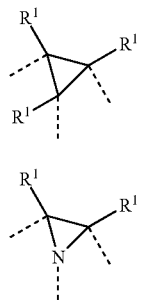

formula (31)

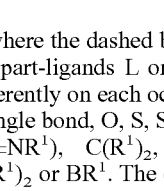

formula (32)

where the dashed bonds in each case indicate the bond to the part-ligands L or L', and W is selected, identically or differently on each occurrence, from the group consisting of a single bond, O, S, S(=O), $S(=O)_2$, $NR^1$, $PR^1$, $P(=O)R^1$, $P(=NR^1)$, $C(R^1)_2$, C(=O), $C(=NR^1)$, $C(=C(R^1)_2)$, $Si(R^1)_2$ or $BR^1$. The other symbols used have the meanings given above.

If V bridges two ligands L to one another or one ligand L to L', V is preferably selected, identically or differently on each occurrence, from the group consisting of $BR^1$, $B(R^1)_2^-$, $C(R^1)_2$, C(=O), $Si(R^1)_2$, $NR^1$, $PR^1$, $P(R^1)_2^+$, $P(=O)(R^1)$, $P(=S)(R^1)$, O, S or a unit of the formula (33) to (42),

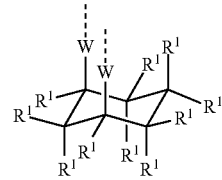

formula (33)

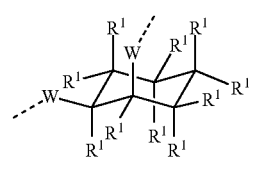

formula (34)

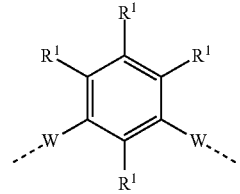

formula (35)

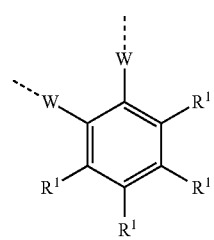

formula (36)

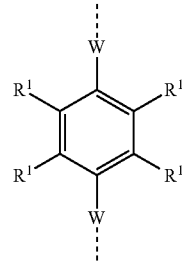

formula (37)

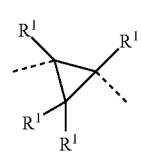

formula (38)

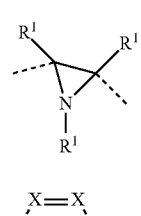

formula (39)

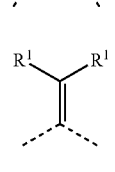

formula (40)

formula (41)

-continued

formula (42)

where the dashed bonds in each case indicate the bond to the part-ligands L or L', T stands on each occurrence, identically or differently, for $C(R^1)_2$, $N(R^1)$, O or S, and the other symbols used each have the meanings indicated above.

Preferred ligands L' as occur in formula (1) are described below. The ligand groups L' can also be selected correspondingly if they are bonded to L via a bridging unit V.

The ligands L' are preferably, identically or differently on each occurrence, neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected, identically or differently on each occurrence, from carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl) phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected, identically or differently on each occurrence, from hydride, deuteride, the halides F⁻, Cl⁻, Br⁻ and I⁻, alkylacetylides, such as, for example, methyl-$C{\equiv}C^-$, tert-butyl-$C{\equiv}C^-$, arylacetylides, such as, for example, phenyl-$C{\equiv}C^-$, cyanide, cyanate, isocyanate, thiocyanate, isothiocyanate, aliphatic or aromatic alcoholates, such as, for example, methanolate, ethanolate, propanolate, iso-propanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, di-iso-propylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups.

These groups are as defined above.

Preferred di- or trianionic ligands are, identically or differently on each occurrence, $O^{2-}$, $S^{2-}$, carbides, which result in coordination in the form R—C≡M, and nitrenes, which result in coordination in the form R—N=M, where R generally stands for a substituent, or $N^{3-}$.

Preferred neutral or mono- or dianionic, bidentate or polydentate ligands L' are selected, identically or differently on each occurrence, from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N, N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-di-iso-propylphenylimino)ethyl]pyridine, 2-[1-(methylimino)ethyl]pyridine, 2-[1-(ethylimino)ethyl]pyridine, 2-[1-(iso-propylimino) ethyl]pyridine, 2-[1-(tert-butylimino)ethyl]pyridine, dimines, such as, for example, 1,2-bis(methylimino)ethane, 1,2-bis(ethylimino)ethane, 1,2-bis(iso-propylimino)ethane, 1,2-bis(tert-butylimino)ethane, 2,3-bis(methylimino)butane, 2,3-bis(ethylimino)butane, 2,3-bis(iso-propylimino)butane, 2,3-bis(tert-butylimino)butane, 1,2-bis(phenylimino)ethane, 1,2-bis(2-methylphenylimino)ethane, 1,2-bis(2,6-di-iso-propylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-iso-propylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis (diphenylphosphino)methane, bis(diphenylphosphino)ethane, bis(diphenylphosphino)propane, bis(diphenylphosphino)butane, bis(dimethylphosphino)methane, bis (dimethylphosphino)ethane, bis(dimethylphosphino) propane, bis(diethylphosphino)methane, bis (diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 2,2,6, 6-tetramethyl-3,5-heptanedione, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl) borate and tetrakis(1-pyrazolyl) borate.

Preference is furthermore given, identically or differently on each occurrence, to bidentate monoanionic ligands L', which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type is known to the person skilled in the art in the area of phosphorescent electroluminescent devices, and he will be able, without inventive step, to select further ligands of this type as ligand L' for compounds of the formula (1). The combination of two groups as depicted by the following formulae (43) to (65) is generally particularly suitable for this purpose, where one group is bonded via a neutral nitrogen atom or a carbene carbon atom and the other group is bonded via a negatively charged carbon atom or a negatively charged nitrogen atom. The ligand L' can then be formed from the groups of the formulae (43) to (65) through these groups bonding to one another in each case at the position denoted by #. The position at which the groups coordinate to the metal is denoted by *. These groups may also be bonded to the ligand L via one or two bridging units V.

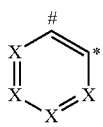

formua (43)

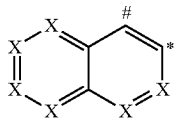

formula (44)

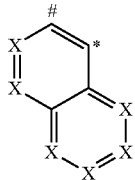

formula (45)

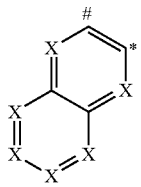

formula (46)

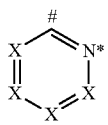

formula (47)

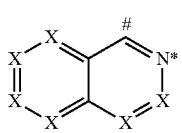

formula (48)

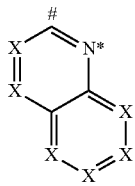

formula (49)

-continued

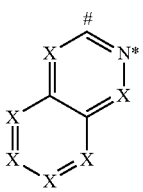

formula (50)

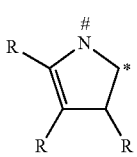

formula (51)

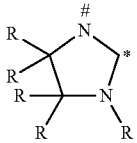

formula (52)

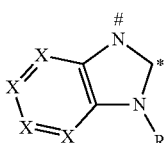

formula (53)

formula (54)

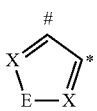

formula (55)

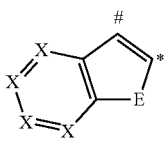

formula (56)

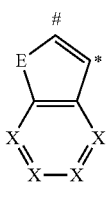

formula (57)

formula (58)

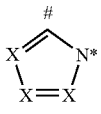

formula (59)

-continued

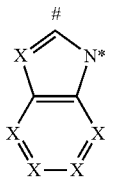
formula (60)

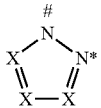
formula (61)

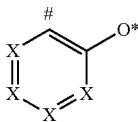
formula (62)

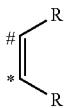
formula (63)

formula (64)

formula (65)

The symbols used here have the same meanings as described above and preferably a maximum of three symbols X in each group stand for N, particularly preferably a maximum of two symbols X in each group stand for N, very particularly preferably a maximum of one symbol X in each group stands for N. Especially preferably, all symbols X stand for CR.

Likewise preferred ligands L' are η⁵-cyclopentadienyl, η⁵-pentamethyl-cyclopentadienyl, η⁶-benzene or η⁷-cycloheptatrienyl, each of which may be substituted by one or more radicals $R^1$.

Likewise preferred ligands L' are 1,3,5-cis-cyclohexane derivatives, in particular of the formula (66), 1,1,1-tri(methylene)methane derivatives, in particular of the formula (67), and 1,1,1-trisubstituted methanes, in particular of the formulae (68) and (69):

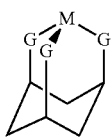
formula (66)

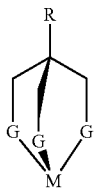
formula (67)

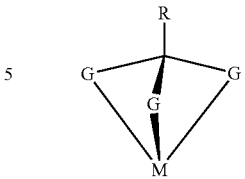
formula (68)

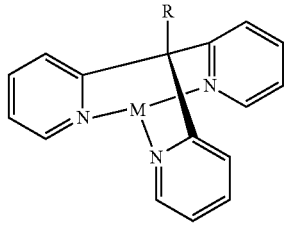
formula (69)

where the coordination to the metal M is shown in each of the formulae, R has the meaning given above, and G stands, identically or differently on each occurrence, for O⁻, S⁻, COO⁻, $P(R^1)_2$ or $N(R^1)_2$.

Preferred radicals R which are present as substituents on X in the structures of the formulae (43) to (69) shown above are selected on each occurrence, identically or differently, from the group consisting of H, D, F, Br, $N(R^1)_2$, CN, $B(OR^1)_2$, $C(=O)R^1$, $P(=O)(R^1)_2$, a straight-chain alkyl group having 1 to 10 C atoms or a straight-chain alkenyl group having 2 to 10 C atoms or a branched or cyclic alkyl, alkenyl or alkynyl group having 3 to 10 C atoms, each of which may be substituted by one or more radicals $R^1$, where one or more H atoms may be replaced by D, F or CN, or an aromatic or heteroaromatic ring system having 5 to 14 aromatic ring atoms, which may in each case be substituted by one or more radicals $R^1$; a plurality of adjacent radicals R here may also form a mono- or polycyclic, aliphatic, aromatic and/or benzo-fused ring system with one another. Particularly preferred radicals R are selected on each occurrence, identically or differently, from the group consisting of H, F, Br, CN, $B(OR^1)_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by F, or an aromatic or heteroaromatic ring system having 5 to 12 aromatic ring atoms, which may in each case be substituted by one or more radicals $R^1$; a plurality of adjacent radicals R here may also form a mono- or polycyclic, aliphatic, aromatic and/or benzo-fused ring system with one another.

The complexes according to the invention can be facial or pseudofacial or they can be meridional or pseudomeridional.

The preferred embodiments indicated above can be combined with one another as desired. In a particularly preferred embodiment of the invention, the preferred embodiments indicated above apply simultaneously.

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (70), with metal ketoketonates of the formula (71), with metal halides of the formula (72) or with dimeric metal complexes of the formula (73):

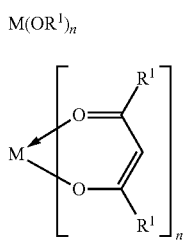  formula (70)

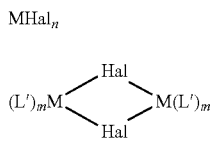  formula (71)

MHal$_n$  formula (72)

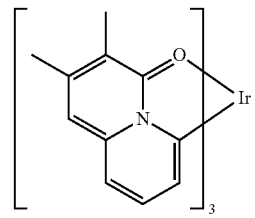

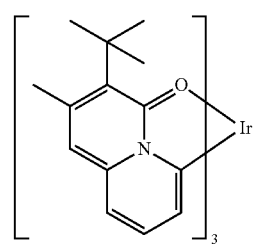

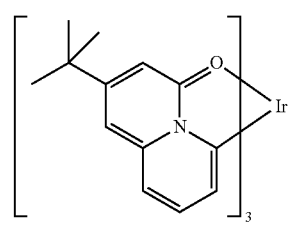

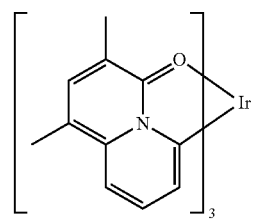

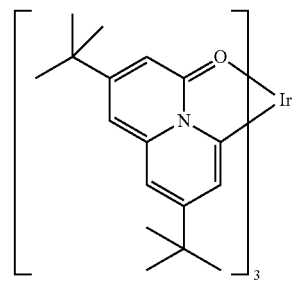

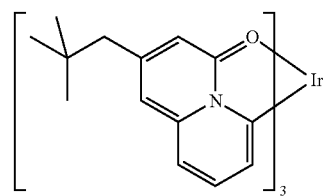

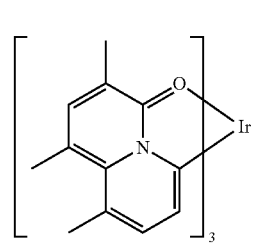

1

2

3

4

5

6

7 formula (73)

where the symbols and indices M, L', m, n and R$^1$ have the meanings indicated above, and Hal=F, Cl, Br or I.

It is likewise possible to use metal compounds, in particular iridium compounds, which carry both alkoxide and/or halide and/or hydroxyl radicals as well as ketoketonate radicals. These compounds may also be charged.

Corresponding iridium compounds which are particularly suitable as starting materials are disclosed in WO 04/085449. Particularly suitable is [IrCl$_2$(acac)$_2$]$^-$, for example Na[IrCl$_2$(acac)$_2$,]. Further articularly suitable iridium starting materials are iridium(II) tris(acetylacetonate) and iridium(III) tris(2,2,6,6-tetramethyl-3,5-heptanedionate).

The synthesis of the complexes is preferably carried out as described in WO 02/060910 and in WO 04/085449. Heteroleptic complexes can also be synthesised, for example, in accordance with WO 05/042548. The synthesis here can also be activated, for example, thermally, photochemically, by microwave radiation and/or in an autoclave.

For the preparation of homoleptic iridium complexes, the ligand is preferably reacted with Na[IrCl$_2$(acac)$_2$] or Ir(acac)$_3$ in the melt or in an inert solvent, such as, for example, polyalcohols (ethylene glycol, glycerol, etc.), polyether alcohols (di-, tri-tetraethylene glycol) or polyethers (di-, tri-, tetra-, polyethylene glycol dimethyl ether), at temperatures of 80 to 350° C. A ratio of the ligand to the Iridium compound of 1:3 to 1:100, preferably 1:4-1:10, is used here.

For the preparation of heteroleptic iridium complexes having two ligands L, it is preferred to react the ligand L with a suitable Ir precursor, preferably iridium(III) chloride hydrate, in the presence of a protic solvent or solvent mixture to give chloro-bridged dimeric iridium complexes [L2IrCl]$_2$, which are then reacted further with one or more ligands L', optionally with addition of additives, such as bases or salts (WO 2007/065523). The preparation of heteroleptic iridium complexes having one ligand L and two ligands L' can be carried out analogously, where the chloro-bridged dimer [L'$_2$IrCl]$_2$ is then synthesised first and reacted with L.

These processes enable the compounds of the formula (1) according to the invention to be obtained in high purity, preferably greater than 99% (determined by means of $^1$H-NMR and/or HPLC).

The synthetic methods explained here enable the preparation of, inter alia, structures 1 to 102 according to the invention which are depicted below.

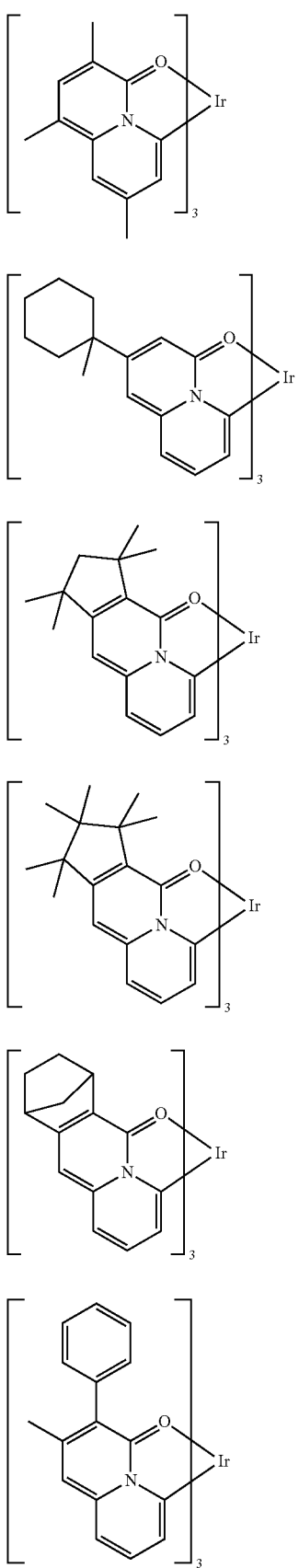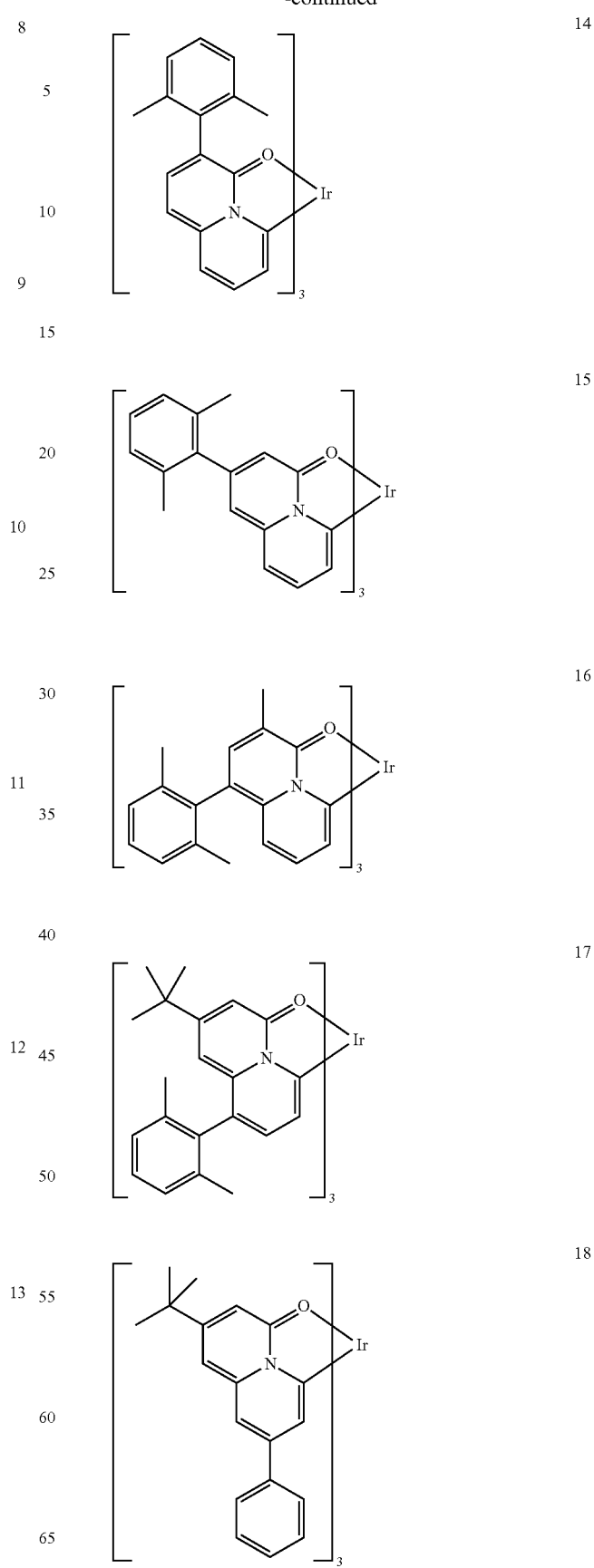

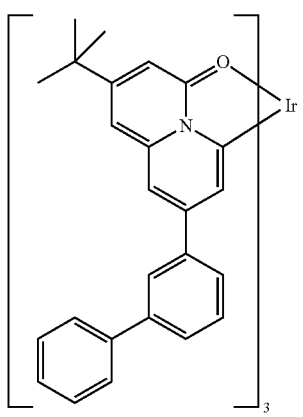
19
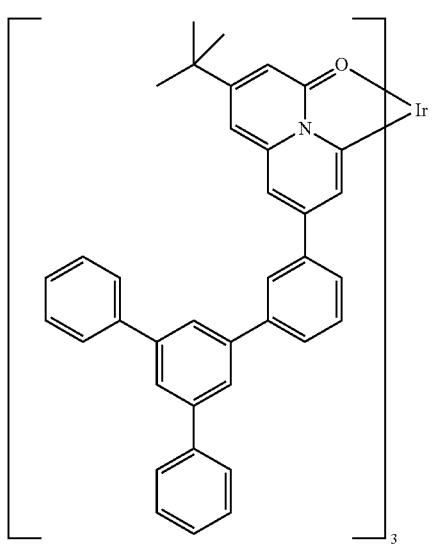
20
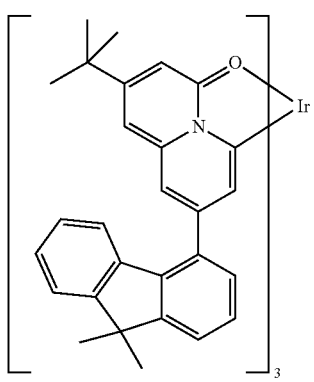
21
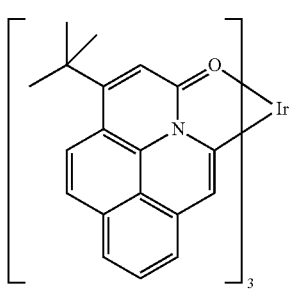
22
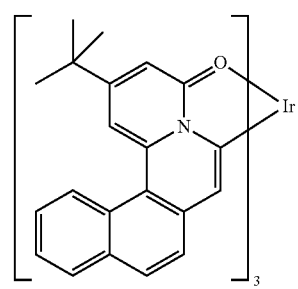
23
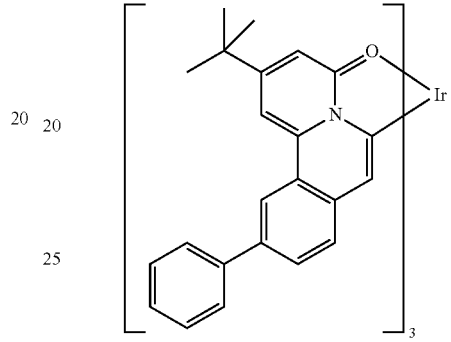
24
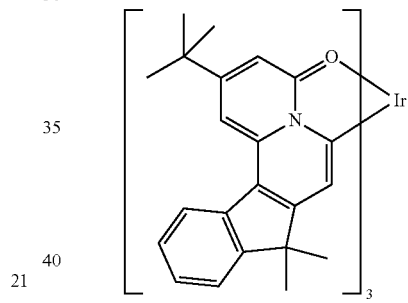
25
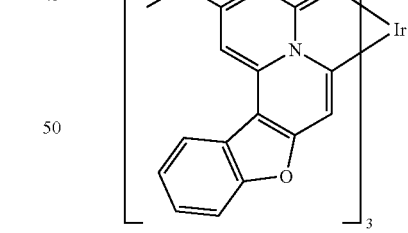
26
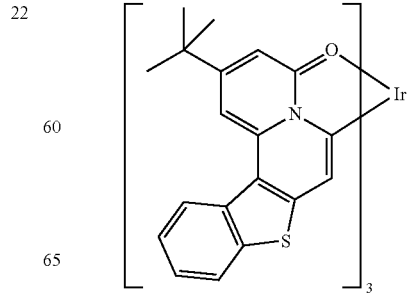
27

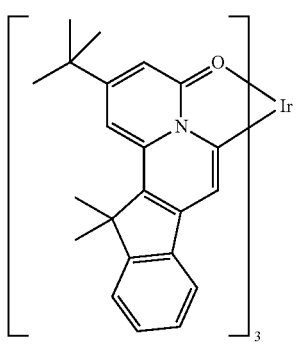
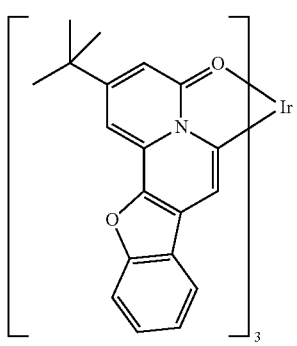
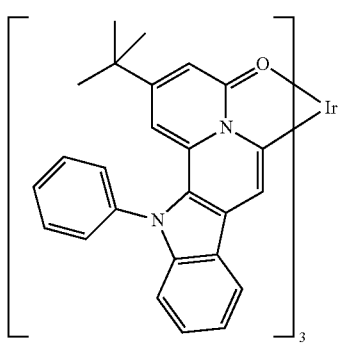
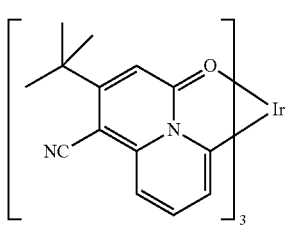
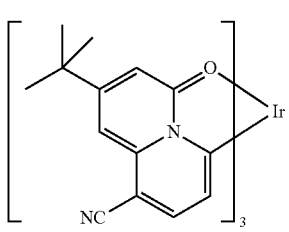
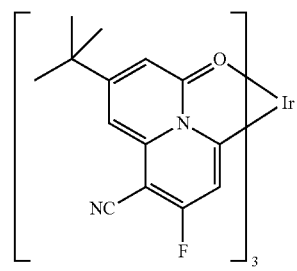
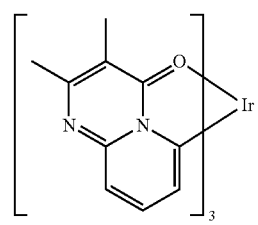
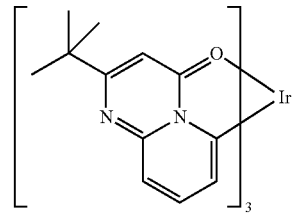
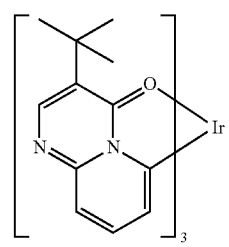
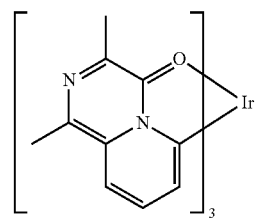
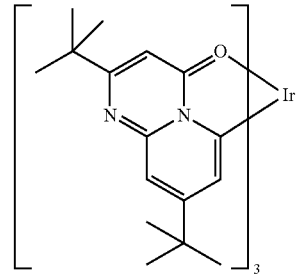

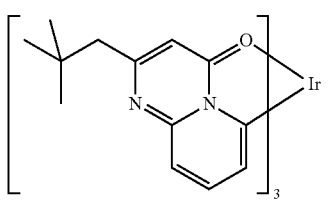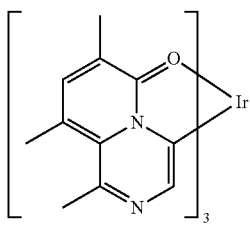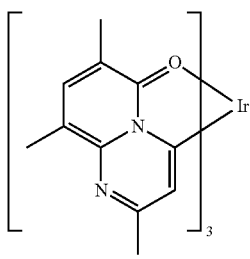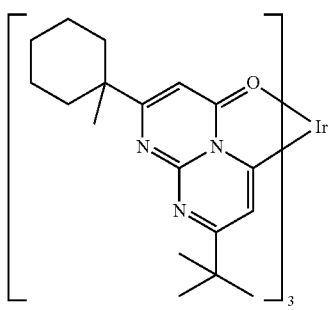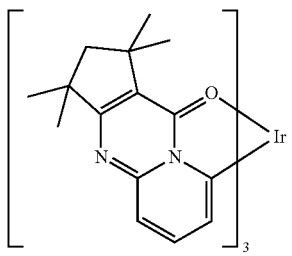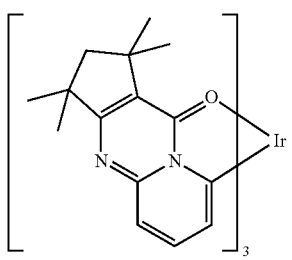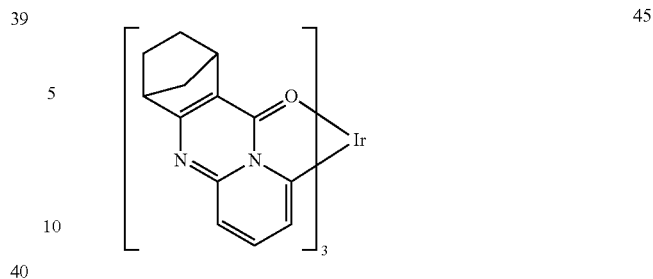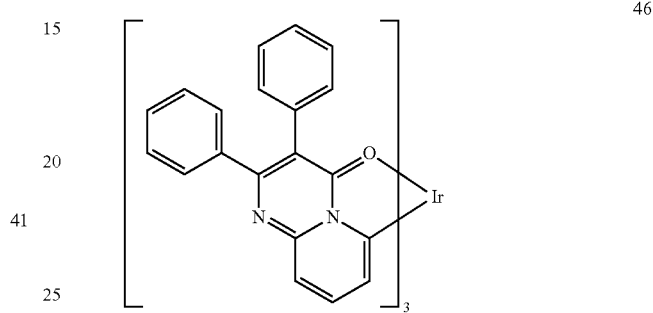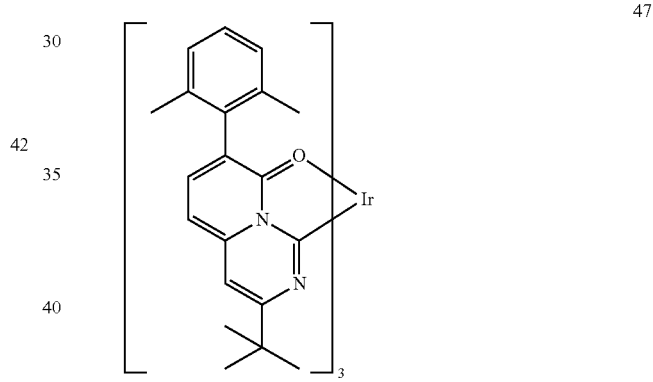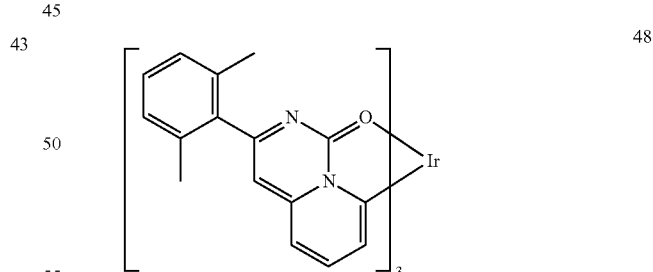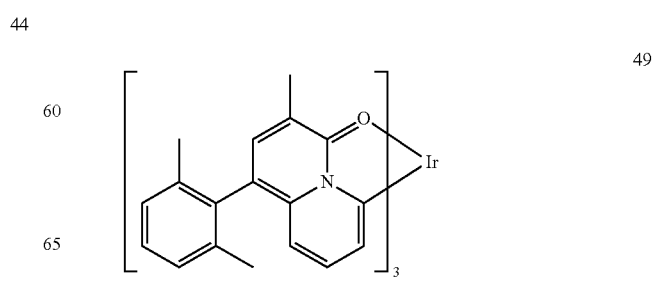

50
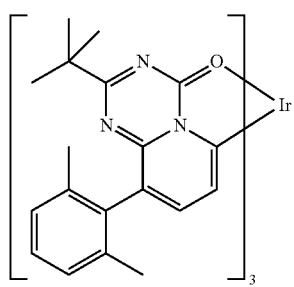
51
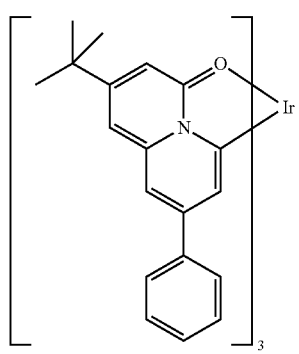
52
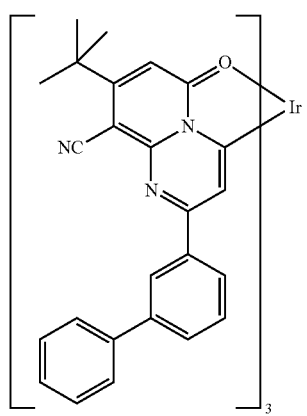
53
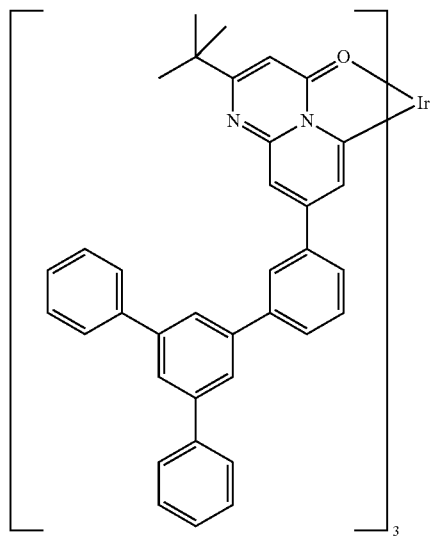
54
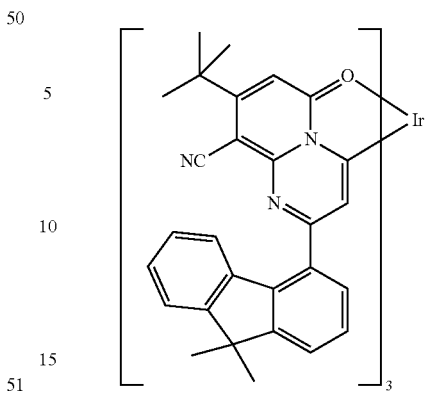
55
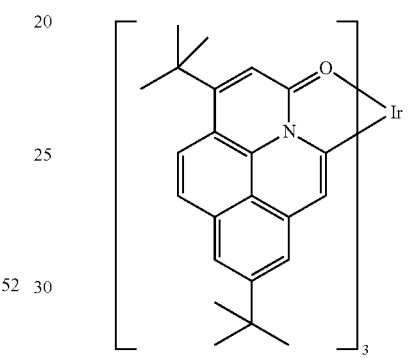
56
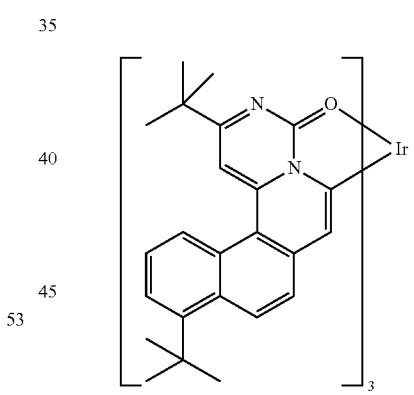
57
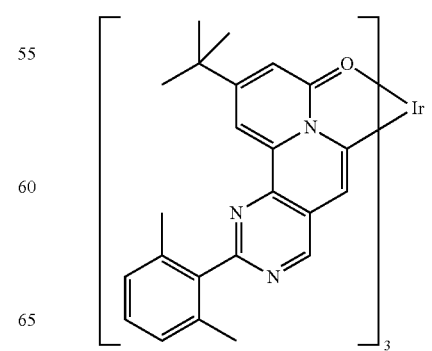

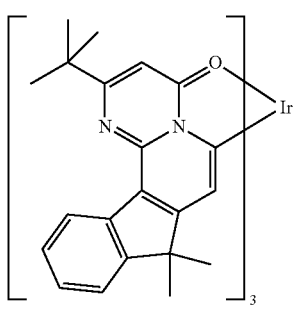
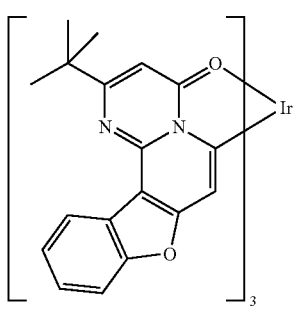
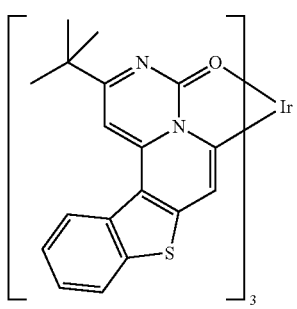
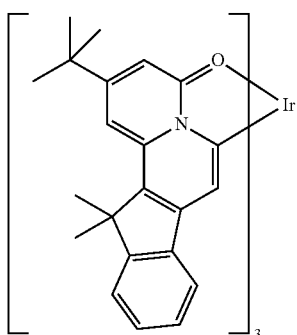
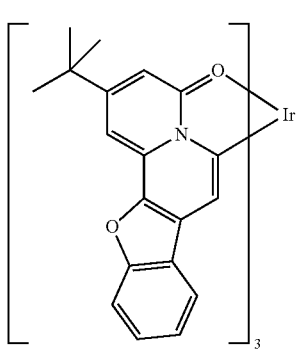
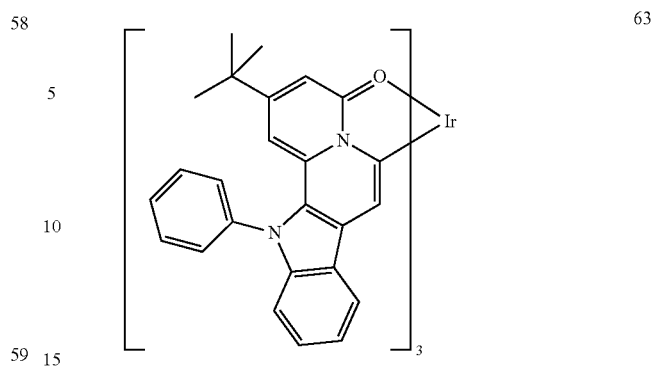
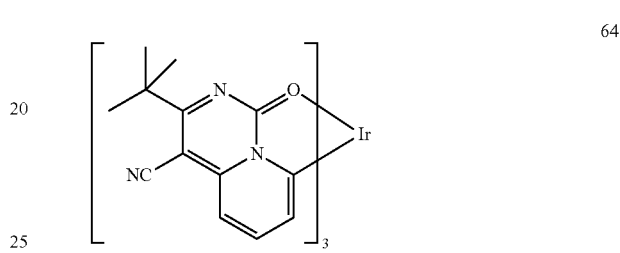
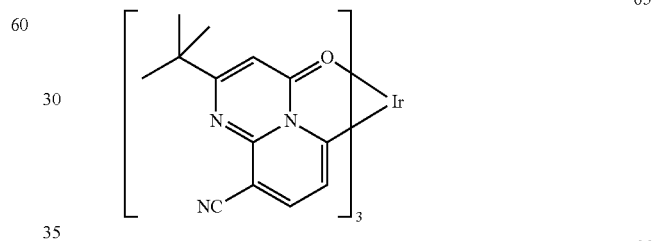
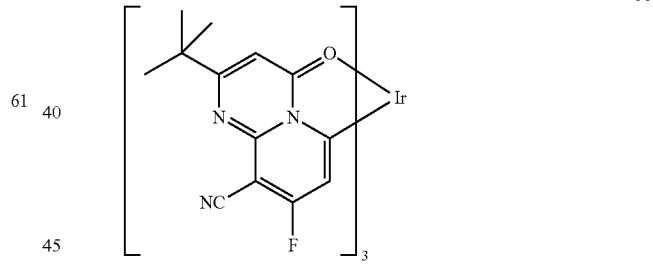
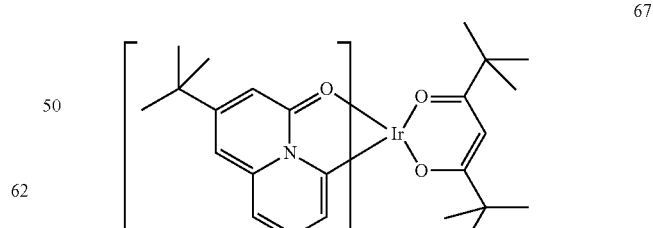
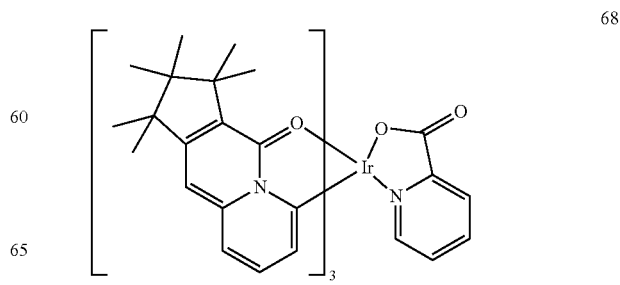

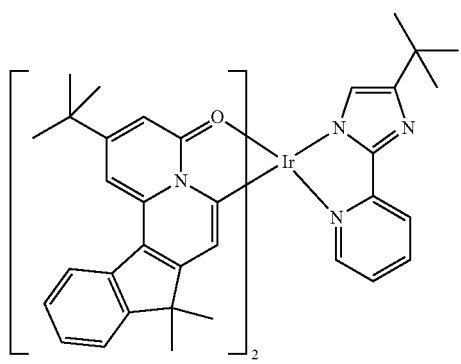
69
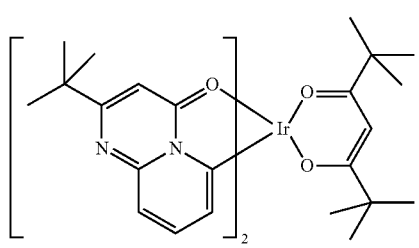
70
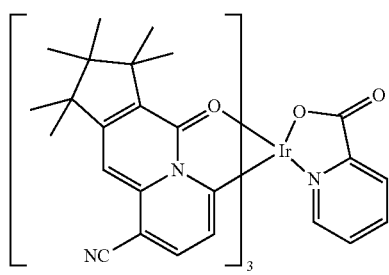
71
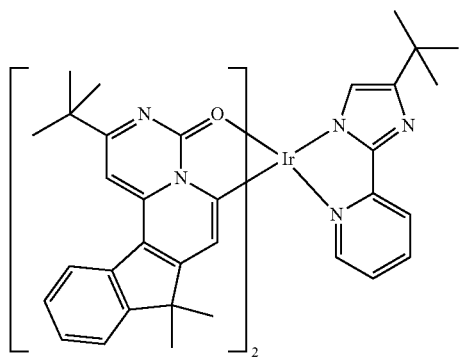
72
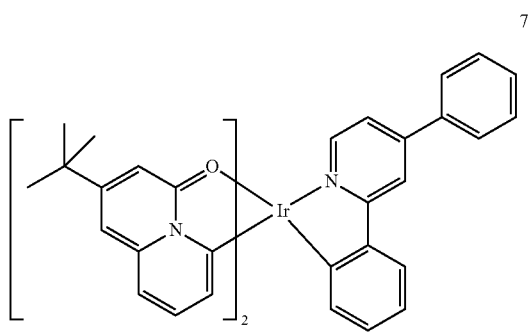
73
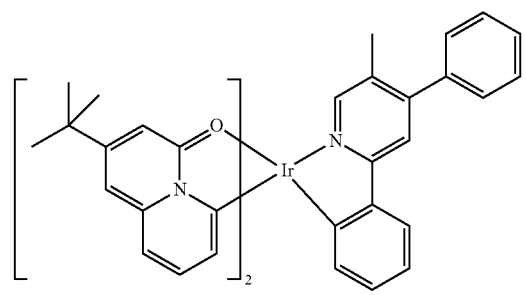
74
75
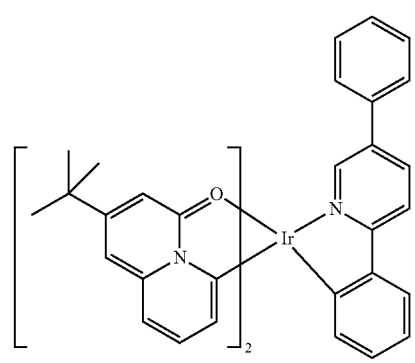
76
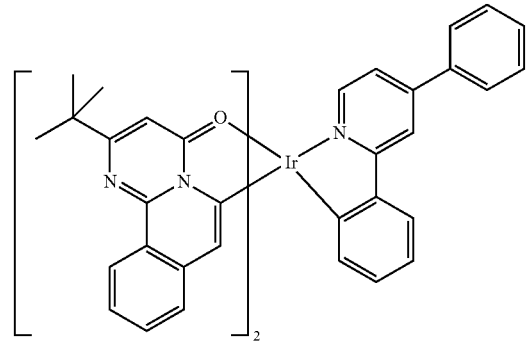
77
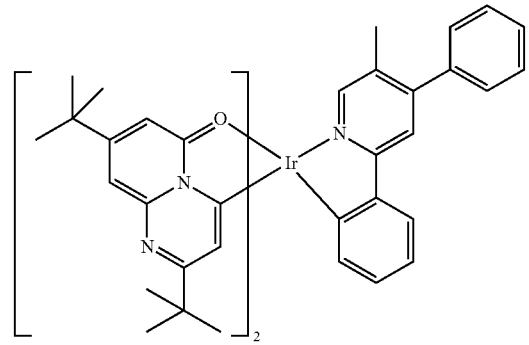

78
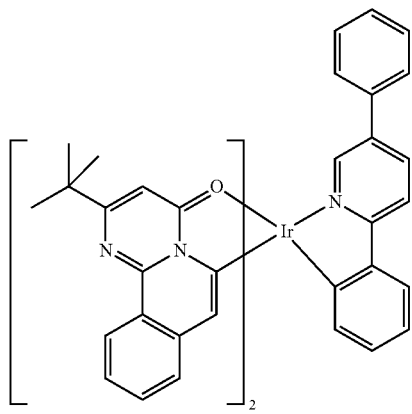
79
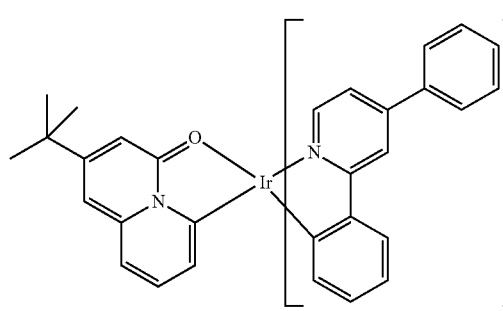
80
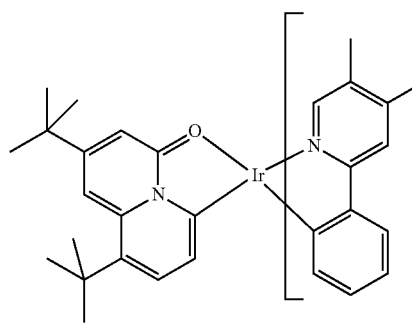
81
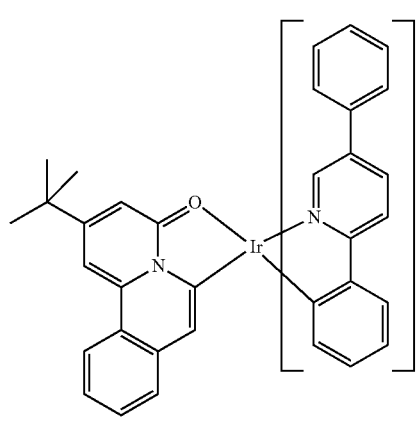
82
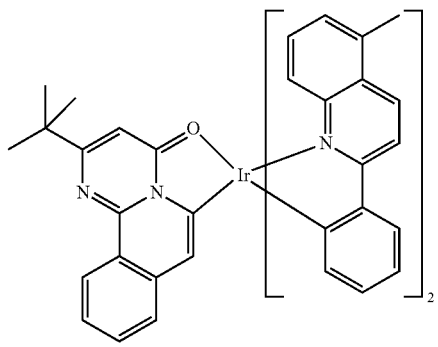
83
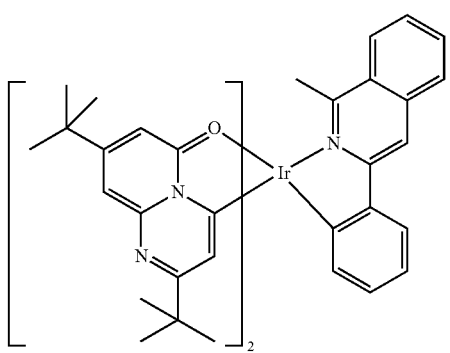
84
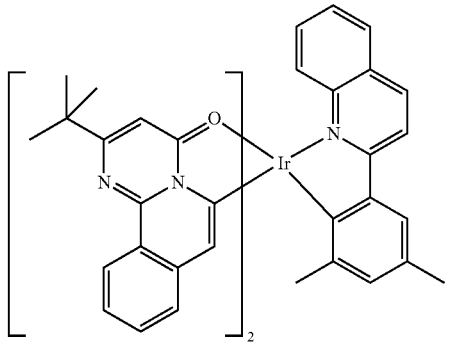
85
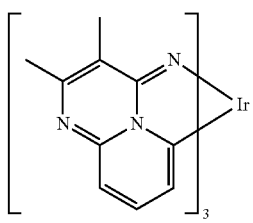
86
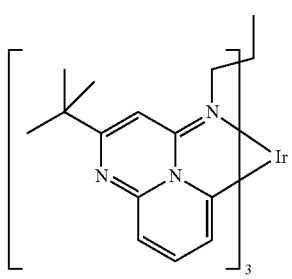

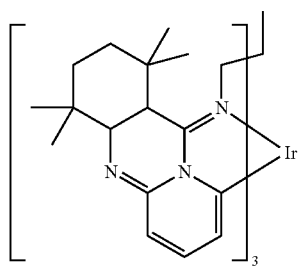
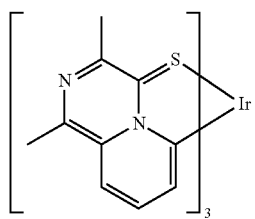
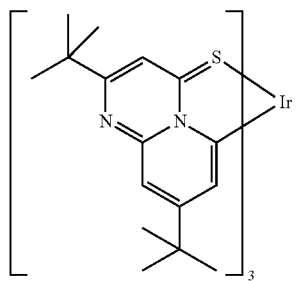
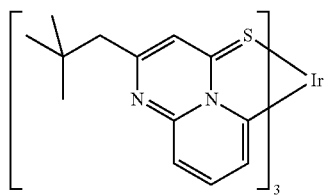
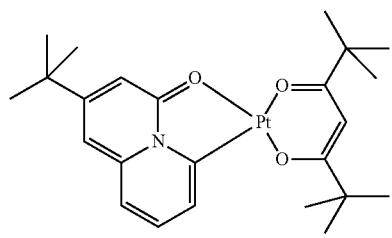
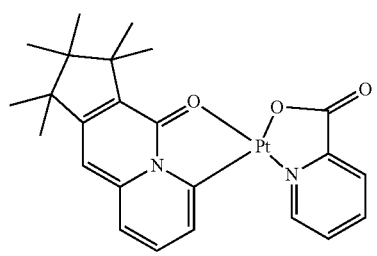
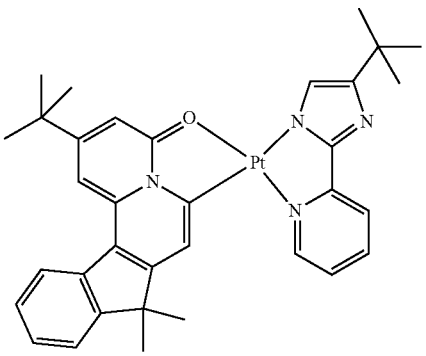
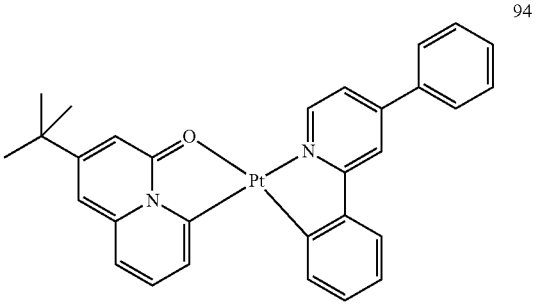
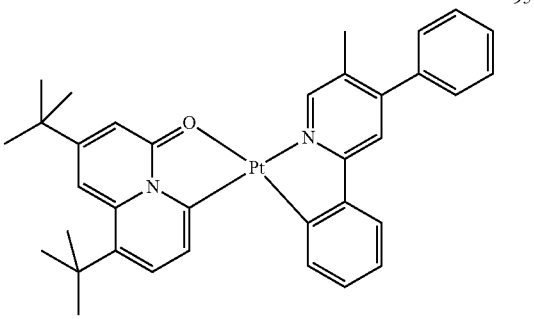
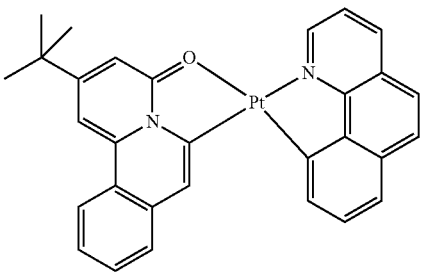
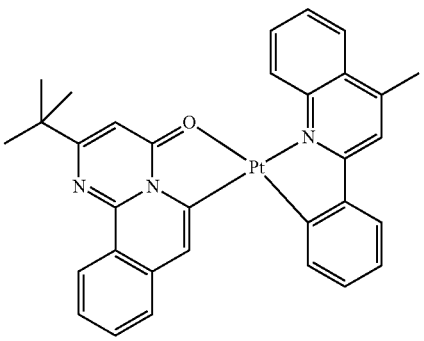

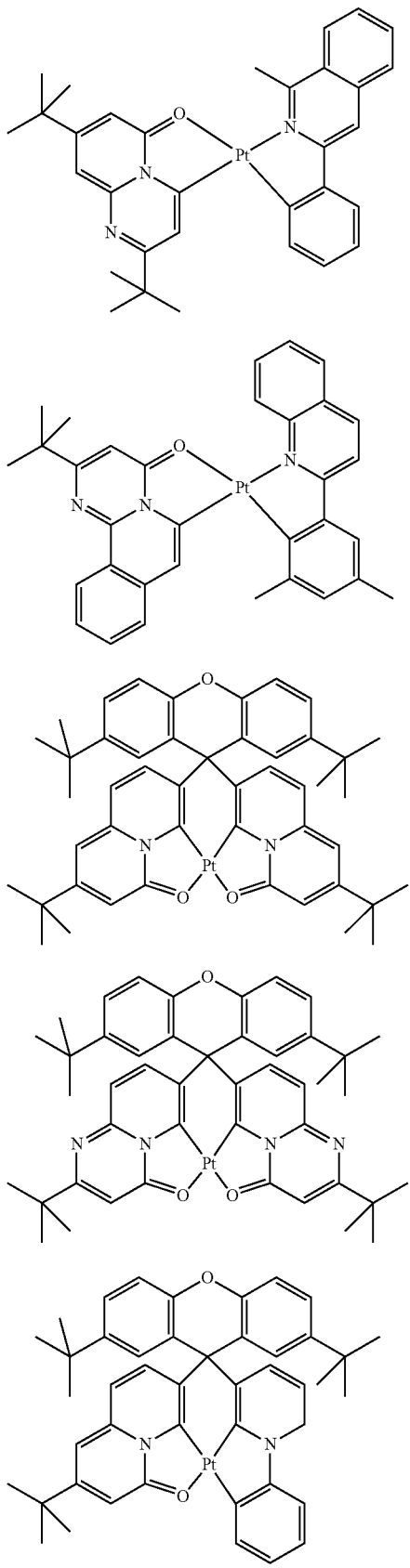

The compounds according to the invention described above can also be used as recurring units in conjugated, partly conjugated or non-conjugated oligomers, polymers or dendrimers. An oligomer in the sense of this invention is taken to mean a compound having about 3 to 10 recurring units, which may be identical or different. The polymerisation here is preferably carried out via a bromine or boronic acid functionality. Thus, compounds of this type can be polymerised, inter alia, into polyfluorenes (for example in accordance with EP 842208 or WO 00/22026), polyspirobifluorenes (for example in accordance with EP 707020 or EP 894107), polydihydrophenanthrenes (for example in accordance with WO 05/014689), polyindenofluorenes (for example in accordance with WO 04/041901 and WO 04/113468), polyphenanthrenes (for example in accordance with WO 05/104264), poly-para-phenylenes (for example in accordance with WO 92/18552), polycarbazoles (for example in accordance with WO 04/070772 or WO 04/113468), polyketones (for example in accordance with WO 05/040302), polysilanes (for example in accordance with WO 05/111113) or polythiophenes (for example in accordance with EP 1028136) or also into copolymers which contain various of these units. They can either be incorporated here into the side chain or into the main chain of the polymer or may also represent branching points of the polymer chains (for example in accordance with WO 06/003000).

The invention thus furthermore relates to conjugated, partly conjugated or non-conjugated oligomers, polymers or dendrimers containing one or more of the compounds of the formula (1), where at least one of the radicals R defined above represents a bond to the polymer or dendrimer. For units of the formula (1), the same preferences as already described above apply in polymers and dendrimers. Apart from the units mentioned above, the oligomers, polymers or dendrimers may contain further units, which are selected, for example, from recurring units which have hole-transport properties or electron-transport properties. The materials known from the prior art are suitable for this purpose.

The above-mentioned oligomers, polymers, copolymers and dendrimers are distinguished by their good solubility in organic solvents and high efficiency and stability in organic electroluminescent devices.

Furthermore, the compounds of the formula (1) according to the invention, in particular those which are functionalised by halogens, may also be functionalised further by standard types of reaction and thus converted into extended compounds of the formula (1). An example which may be mentioned here is the functionalisation by means of arylboronic acids by the Suzuki method or by means of amines by the Hartwig-Buchwald method.

For processing from solution, solutions or formulations of the compounds of the formula (1) are necessary. It may be preferred here to use mixtures of two or more solvents.

The present invention furthermore relates to a formulation comprising a compound according to the invention and at least one further compound. The further compound can be, for example, a solvent. Suitable solvents are, for example, toluene, o-, m- or p-xylene, anisoles, methyl benzoate, dimethylanisoles, mesitylenes, tetralin, veratrol, chlorobenzene, phenoxytoluene, in particular 3-phenoxytoluene, dioxane, THF, methyl-THf, THP or mixtures of these solvents. The way in which such solutions can be prepared is known to the person skilled in the art and is described, for example, in WO 2002/072714, WO 2003/019694 and the literature cited therein. However, the further compound may also be a further organic or inorganic compound which is likewise employed in the electronic device, for example a matrix material. This further compound may also be polymeric.

The compounds of the formula (1) described above or the preferred embodiments mentioned above can be used as active component in an electronic device. The present invention therefore furthermore relates to the use of a compound of the formula (1) or in accordance with one of the preferred embodiments in an electronic device. Furthermore, the compounds according to the invention can be employed for the generation of singlet oxygen, in photocatalysis or in oxygen sensors.

The present invention again furthermore relates to an electronic device comprising at least one compound of the formula (1) or in accordance with one of the preferred embodiments.

An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. A preferred embodiment are three-layer systems, where the three layers exhibit blue, green and orange or red emission (see, for example, WO 2005/011013), or systems which have more than three emitting layers. A further preferred embodiment are two-layer systems, where the two layers exhibit either blue and yellow or cyan and orange emission. Two-layer systems are or interest, in particular, for lighting applications. Such embodiments are particularly suitable with the compounds according to the invention, since these frequently exhibit yellow or orange emission. The white-emitting electroluminescent devices can be employed for lighting applications or as backlight for displays or with coloured filters as display.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99 and 1% by vol., preferably between 98 and 10% by vol., particularly preferably between 97 and 60% by vol., especially between 95 and 85% by vol., of the matrix material or matrix materials, based on the entire mixture comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or WO 2011/088877.

It may also be preferred to employ a plurality of different matrix materials as mixture. Suitable for this purpose are, in particular, mixtures of at least one electron-transporting matrix material and at least one hole-transporting matrix material or mixtures of at least two electron-transporting matrix materials or mixtures of at least one hole- or electron-transporting matrix material and at least one further material having a large band gap which is thus substantially electrically inert and does not participate in charge transport to a significant extent, if at all, as described, for example, in WO 2010/108579. A preferred combination is, for example, the use of an aromatic ketone or a triazine derivative with a triarylamine derivative or a carbazole derivative as mixed matrix for the metal complex according to the invention.

It is furthermore preferred to employ a mixture of two or more triplet emitters together with a matrix. The triplet emitter having the shorter-wave emission spectrum serves as co-matrix for the triplet emitter having the longer-wave emission spectrum here. Thus, for example, blue- or green-emitting triplet emitters can be employed as co-matrix for the complexes of the formula (1) according to the invention.

The cathode preferably comprises metals having a low work function, metal alloys or multilayered structures comprising various metals, such as, for example, alkaline-earth metals, alkali metals, main-group metals or lathanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrons (for example Al/Ni/NiOx, Al/PtOx) may also be preferred. For some applications, at least one of the electrodes must be transparent in order either to facilitate irradiation of the organic material (O-SCs) or the coupling-out of light (OLEDs/PLEDs, O-LASERs). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished by the following surprising advantages over the prior art:

1. Organic electroluminescent devices comprising compounds of the formula (1) as emitting materials have a good lifetime.
2. Organic electroluminescent devices comprising compounds of the formula (1) as emitting materials have good efficiency.
3. The metal complexes according to the invention and the ligands required therefor are accessible synthetically in a simple manner and in high yields.
4. The metal complexes according to the invention, in particular those which do not contain a group of the formula (3) or (4), have a lower molecular weight compared with the triplet emitters usually used in OLEDs, which is reflected in a lower sublimation temperature.

These advantages mentioned above are not accompanied by an impairment of the other electronic properties.

The invention is explained in greater detail by the following examples, without wishing to restrict it thereby. On the basis of the descriptions, the person skilled in the art will be able to synthesise further compounds according to the invention without inventive step and use them in electronic devices and will thus be able to carry out the invention throughout the range claimed.

EXAMPLES

The following syntheses are carried out, unless indicated otherwise, under a protective-gas atmosphere in dried solvents. The metal complexes are in addition handled with exclusion of light or under yellow light. The solvents and reagents can be purchased, for example, from Sigma-AL-DRICH or ABCR. The numbers in the case of the compounds known from the literature, some of which are also indicated in square brackets, are the CAS numbers of the compounds.

A: Synthesis of the Ligands L:

The synthesis of the following ligands is described in the literature:

| Ligand | Structure | Literature |
|---|---|---|
| L1 | 880384-66-7 | I. Hachiya et al., Heterocycles 67, 2, 523, 2006 |
| L2 | 41969-31-7 | W. Eberbach et al., Tetrahedron Letters, 30(41), 5591, 1989 |
| L3 | 159219-11-1 | V. Farina et al., Organic Reactions (Hoboken, NJ, United States), 50, 1997 |
| L4 | 675820-40-3 | Yu. M. Volovenko et al., Chemistry of Heterocyclic Compounds (New York, NY, United States) (Translation of Khimiya Geterotsiklicheskikh Soedinenii), 39(4), 545-546, 2003 |
| L5 | 58245-89-9 | H. Yamananka et al., Chemical & Pharmaceutical Bulletin, 29(4), 1049, 1981 |
| L6 | 7547-92-4 | J. DeHouwer et al., Angewandte Chemie, International Edition, 51(11), 2745, 2012 |
| L7 | 1693-94-3 | D. Kim. Et al., Archives of Pharmacal Research, 28(9), 1019, 2005 |
| L8 | 30247-64-4 | P. L. Ferrarini et al., Journal of Heterocyclic Chemistry, 20(4), 1053, 1983 |
| L9 | 16867-29-1 | T. H. Brown et al., Journal of the Chemical Society [Section] C: Organic, (11), 2163, 1971 |
| L10 | 16054-93-6 | L. -J. Pemg et al., Journal of Medicinal Chemistry, 54(21), 7729, 2011 |
| L11 | 87591-85-3 | L. -J. Pemg et al., Journal of Medicinal Chemistry, 54(21), 7729, 2011 |

| Ligand | Structure | Literature |
|---|---|---|
| L12 |  56671-32-0 | K. Ding et al., WO2010006496 |
| L13 | 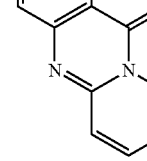 878-96-1 | Maity et al., Tetrahedron Letters, 52(23), 3033, 2011 |
| L14 | 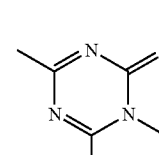 57859-90-2 | T. Kato et al., Chemical & Pharmaceutical Bulletin, 23(10), 2251, 1975 |
| L15 | 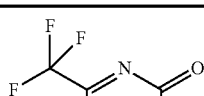 154160-14-2 | Kiselyov et al., Tetrahedron Letters, 35(2), 207, 1994 |

Example L16

2-tert-Butylquinolizin-4-one, L16

A mixture of 9.4 g (100 mmol) of 2-aminopyridine [504-29-0], 19.0 g (120 mmol) of methyl 3-oxo-4,4-dimethylpentanoate [55107-14-7], 960 mg (5 mmol) of p-toluenesulfonic acid monohydrate and 200 ml of o-xylene is heated under reflux on a water separator for 18 h. The o-xylene is then distilled off on the water separator, the temperature is increased to 160° C., and the mixture is stirred at this temperature for a further 2 h in order to remove final residues of distillate, then allowed to cool to 50° C., 30 ml of cyclohexane are added, the mixture is allowed to cool to room temperature, the solid which has crystallised out is filtered off with suction, washed twice with a little cyclohexane and dried in vacuo. The purification is carried out by recrystallisation from cyclohexane twice and subsequent fractional sublimation (p about $10^{-5}$ mbar, T=160° C.). Yield: 9.7 g (48 mmol), 48%. Purity: >99.5% according to $^1$H-NMR.

The synthesis of the following ligands is described in the literature:

| Ex. | Amine | β-Ketocarboxylic acid ester | Ligand | Yield |
|---|---|---|---|---|
| L17 |  | 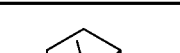 | | 44% |

-continued

| Ex. | Amine | β-Keto-carboxylic acid ester | Ligand | Yield |
|---|---|---|---|---|
| L18 | 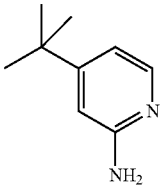 | 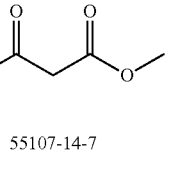<br>55107-14-7 | 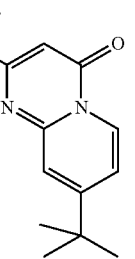 | 50% |
| L19 | 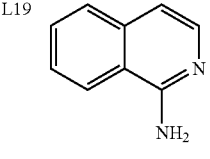<br>1532-84-9 | 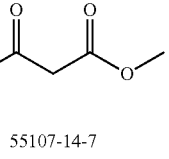<br>55107-14-7 | 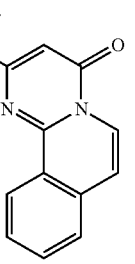 | 51% |
| L20 | 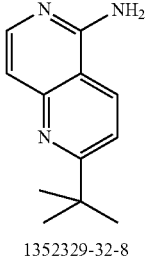<br>1352329-32-8 | 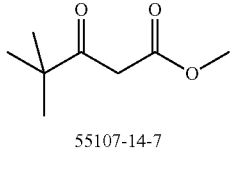<br>55107-14-7 | 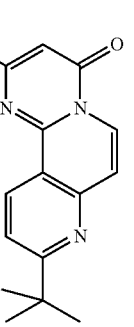 | 46% |
| L21 | 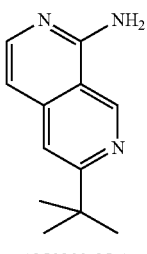<br>1352329-35-1 | 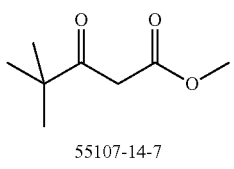<br>55107-14-7 | 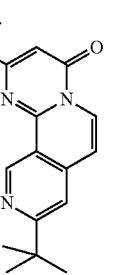 | 41% |

Example L22-tert-Butylquinolizin-4-one, L22

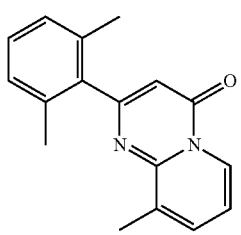 [SMILES: Cc1cccc(C)c1-c1cc(=O)n2cccc(C)c2n1]

A mixture of 19.5 g (100 mmol) of 2-chloro-9-methyl-4H-pyrido[1,2-a]-pyrimidin-4-one [17326-22-6], 19.5 g (130 mmol) of 2,6-dimethylphenylboronic acid [100379-00-8], 48.9 g (150 mmol) of caesium carbonate, 821 mg (2 mmol) of S-Phos, 449 mg (2 mmol) of palladium(II) acetate, 200 g of glass beads (diameter 3 mm) and 300 ml of dioxane is heated under reflux for 18 h. After cooling, the salts and glass beads are filtered off through a Celite bed, the salts are rinsed twice with 200 ml of dioxane each time, the filtrate is evaporated to dryness, the residue is taken up in 500 ml of ethyl acetate, the organic phase is washed three times with 300 ml of water each time, once with 300 ml of saturated sodium chloride solution, dried over magnesium sulfate and evaporated to dryness in vacuo. The purification is carried out by recrystallisation from ethyl acetate/methanol twice and subsequent fractional sublimation (p about $10^{-5}$ mbar, T=200° C.). Yield: 15.1 g (57 mmol), 57%. Purity: >99.5% according to $^1$H-NMR.

B: Synthesis of the Metal Complexes

1) Homoleptic Tris-Facial Iridium Complexes:

Variant A

Trisacetylacetonatoiridlum(III) as iridium starting material

A mixture of 10 mmol of trisacetylacetonatoiridium(III) [15635-87-7] and 60 mmol of the ligand L, optionally 1-10 g, typically 3 g, of an inert high-boiling additive as melting aid or solvent, for example hexadecane, m-terphenyl, triphenylene, diphenyl ether, 3-phenoxytoluene, 1,2-, 1,3-, 1,4-diphenoxybenzene, triphenylphosphine oxide, sulfolane, 18-crown-6, triethylene glycol, glycerol, polyethylene glycols, phenol, 1-naphthol, hydroquinone, etc., and a glass-clad magnetic stirrer bar are melted under vacuum ($10^{-5}$ mbar) into a thick-walled 50 ml glass ampoule. The ampoule is heated at the temperature indicated for the time indicated, with the molten mixture being stirred with the aid of a magnetic stirrer. In order to prevent sublimation of the ligands at relatively cold points of the ampoule, the entire ampoule must have the temperature indicated. Alternatively, the synthesis can be carried out in a stirred autoclave with glass insert. After cooling (NOTE: the ampoules are usually under pressure!), the ampoule is opened, the sinter cake is stirred for 3 h with 100 g of glass beads (diameter 3 mm) in 100 ml of a suspension medium (the suspension medium is selected so that the ligand is readily soluble therein, but the metal complex has low solubility therein; typical suspension media are methanol, ethanol, dichloromethane, acetone, THF, ethyl acetate, toluene, etc.) and mechanically digested at the same time. The fine suspension is decanted off from the glass beads, the solid is filtered off with suction, rinsed with 50 ml of the suspension medium and dried in vacuo. The dry solid is placed on an aluminium oxide bed (aluminium oxide, basic, activity grade 1) with a depth of 3-5 cm in a continuous hot extractor and then extracted with an extractant (initially introduced amount about 500 ml, the extractant is selected so that the complex is readily soluble therein at elevated temperature and has low solubility therein at low temperature; particularly suitable extractants are hydrocarbons, such as toluene, xylenes, mesitylene, naphthalene, o-dichlorobenzene; halogenated aliphatic hydrocarbons are generally unsuitable since they may halogenate or decompose the complexes). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, with the aluminium oxide bed being omitted from the 2nd extraction. When a purity of 99.5-99.9% has been achieved, the metal complex is heated or sublimed. The heating is carried out in a high vacuum (p about $10^{-6}$ mbar) in the temperature range from about 200-300° C. The sublimation is carried out in a high vacuum (p about $10^{-6}$ mbar) in the temperature range from about 300-400° C., where the sublimation is preferably carried out in the form of a fractional sublimation.

If chiral ligands are employed, the derived fac-metal complexes are obtained as a diastereomer mixture. The enantiomers Λ,Δ of point group C3 generally have significantly lower solubility in the extractant than the enantiomers of point group C1, which consequently become enriched in the mother liquor. Separation of the C3 diastereomers from the C1 diastereomers in this way is frequently possible. In addition, the diastereomers can also be separated chromatographically. If ligands of point group C1 are employed in enantiomerically pure form, a diastereomer pair Λ,Δ of point group C3 forms. The diastereomers can be separated by crystallisation or chromatography and thus obtained as enantiomerically pure compounds.

Variant B

Tris(2,2,6,6-tetramethyl-3,5-heptanedionato)iridium (III) as iridium starting material Procedure analogous to variant A, using 10 mmol of tris(2,2,6,6-tetramethyl-3,5-heptanedionato)iridium [99581-86-9] instead of 10 mmol of trisacetylacetonatoiridium(III). The use of this starting material is advantageous since the purity of the crude products obtained is frequently better than in the case of Variant A. In addition, the build-up of pressure in the ampoule is frequently not as pronounced.

| Ex. | Ligand L | fac-Ir complex Diastereomer | Variant Reaction temp./reaction time Suspension medium Extractant | Yield |
|---|---|---|---|---|
| Ir(L1)$_3$ | L1 | Ir(L1)$_3$ | A 260° C./40 h Ethyl acetate o-Xylene | 38% |
| Ir(L2)$_3$ | L2 | Ir(L2)$_3$ | B 280° C./40 h Acetone o-Xylene | 46% |
| Ir(L3)$_3$ | L3 | Ir(L3)$_3$ | as Ir(L2)$_3$ | 43% |
| Ir(L4)$_3$ | L4 | Ir(L4)$_3$ | as Ir(L2)$_3$ | 28% |
| Ir(L5)$_3$ | L5 | Ir(L5)$_3$ | as Ir(L2)$_3$ | 48% |
| Ir(L6)$_3$ | L6 | Ir(L6)$_3$ | as Ir(L2)$_3$ | 45% |
| Ir(L7)$_3$ | L7 | Ir(L7)$_3$ | B 280° C./48 h Ethyl acetate o-Xylene | 50% |
| Ir(L8)$_3$ | L8 | Ir(L8)$_3$ | as Ir(L7)$_3$ | 49% |
| Ir(L9)$_3$ | L9 | Ir(L9)$_3$ | as Ir(L7)$_3$ | 43% |
| Ir(L10)$_3$ | L10 | Ir(L10)$_3$ | as Ir(L7)$_3$ | 38% |
| Ir(L11)$_3$ | L11 | Ir(L11)$_3$ | as Ir(L7)$_3$ | 51% |
| Ir(L12)$_3$ | L12 | Ir(L12)$_3$ | as Ir(L7)$_3$ | 47% |
| Ir(L13)$_3$ | L13 | Ir(L13)$_3$ | B 280° C./60 h | 56% |

| Ex. | Ligand L | fac-Ir complex Diastereomer | Variant Reaction temp./reaction time Suspension medium Extractant | Yield |
|---|---|---|---|---|
| Ir(L14)₃ | L14 | Ir(L14)₃ | Ethyl acetate o-Xylene B 290° C./48 h Ethyl acetate Mesitylene | 23% |
| Ir(L15)₃ | L15 | Ir(L15)₃ | as Ir(L14)₃ | 20% |
| Ir(L16)₃ | L16 | Ir(L16)₃ | as Ir(L2)₃ | 45% |
| Ir(L17)₃ | L17 | Λ,Δ-Ir(L17)₃ | as Ir(L2)₃ | 51% |
| Ir(L18)₃ | L18 | Ir(L18)₃ | as Ir(L2)₃ | 45% |
| Ir(L19)₃ | L19 | Ir(L19)₃ | as Ir(L2)₃ | 45% |
| Ir(L20)₃ | L20 | Ir(L20)₃ | as Ir(L14)₃ | 47% |
| Ir(L21)₃ | L21 | Ir(L21)₃ | as Ir(L14)₃ | 39% |
| Ir(L22)₃ | L22 | Ir(L22)₃ | as Ir(L2)₃ | 49% |

2) Complexes of the Formula [Ir(L)₂Cl]₂:

A mixture of 10 mmol of sodium bisacetylacetonatodichloroiridate(III) [770720-50-8], 22 mmol of the ligand L and a glass-clad magnetic stirrer bar are introduced into a cylindrical reaction vessel (volume 40 ml) with screw lid and Teflon septum under inert gas (nitrogen or argon). The reaction mixture is slowly heated with stirring until a melt forms. The temperature is then slowly increased in 20° C. steps every 20 min. until the final temperature (see below) has been reached, during which the acetylacetone forming is released via a cannula in the septum. When the final temperature has been reached, the reaction mixture is kept at the final temperature for a further 20 h. After cooling under protective gas, the sinter cake is mechanically comminuted, stirred with 100 g of glass beads (diameter 3 mm) in 100 ml of the suspension medium indicated (the suspension medium is selected so that the ligand is readily soluble therein, but the chloro dimer of the formula [Ir(L)₂Cl]₂ has low solubility therein; typical suspension media are diethyl ether, tert-butyl methyl ether, ethyl acetate, dichloromethane, acetone, ethyl acetate, toluene, etc.) for 3 h and mechanically digested in the process. The fine suspension is decanted off from the glass beads, the solid ([Ir(L)₂Cl]₂, which still contains about 2 eq of NaCl (called the crude chloro dimer below) is filtered off with suction and dried in vacuo. The crude chloro dimer obtained in this way is employed subsequently without further purification.

The following iridium complexes can be prepared analogously:

| Ex. | Ligand L | Ir complex | Final temp. Suspension medium | Yield |
|---|---|---|---|---|
| [Ir(L1)₂Cl]₂ | L1 | [Ir(L1)₂Cl]₂ | 260° C. Ethyl acetate | 92% |
| [Ir(L9)₂Cl]₂ | L9 | [Ir(L9)₂Cl]₂ | 280° C. Acetone | 95% |
| [Ir(L12)₂Cl]₂ | L12 | [Ir(L12)₂Cl]₂ | 270° C. Ethyl acetate | 93% |
| [Ir(L16)₂Cl]₂ | L16 | [Ir(L16)₂Cl]₂ | 270° C. Ethyl acetate | 93% |
| [Ir(L17)₂Cl]₂ | L17 | [Ir(L17)₂Cl]₂ | 290° C. Ethyl acetate | 90% |
| [Ir(L19)₂Cl]₂ | L19 | [Ir(L19)₂Cl]₂ | 270° C. Ethyl acetate | 92% |
| [Ir(L22)₂Cl]₂ | L22 | [Ir(L22)₂Cl]₂ | 270° C. Ethyl acetate | 94% |

3) Complexes of the Formula Ir(L)$_2$(L') with Ligands L' Containing O—O, O—N, N—N Donor Atoms The crude chloro dimer of the formula [Ir(L)$_2$Cl]2 obtained in 2) is suspended in a mixture of 75 ml of 2-ethoxyethanol and 25 ml of water, and 13 mmol of the ligand L' and 15 mmol of sodium carbonate are added. After stirring under reflux and with exclusion of light for 20 h, a further 75 ml of water are added dropwise, the mixture is cooled, the solid is filtered off with suction, washed three times with 50 ml of water each time and three times with 50 ml of methanol each time and dried in vacuo. The dry solid is placed on a Celite bed with a depth of 3-5 cm in a continuous hot extractor and then extracted with the extractant indicated (amount introduced about 300 ml; the extractant is selected so that the complex is readily soluble therein at elevated temperature and has low solubility therein when cold; particularly suitable extractants are hydrocarbons, such as toluene, xylenes, mesitylene, naphthalene, o-dichlorobenzene, acetone, ethyl acetate (EA), dichloromethane (DCM), etc.). When the extraction is complete, the extractant is evaporated to about 100 ml in vacuo. Metal complexes which have excessively good solubility in the extractant are brought to crystallisation by evaporation of the eluate to 50 ml and dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated. When a purity of 99.5-99.9% has been reached, the metal complex is heat-treated or sublimed. Besides the hot-extraction method for purification, the purification can also be carried out by chromatography on silica gel or aluminium oxide using suitable eluents (see below). The heat treatment is carried out in a high vacuum (p about 10$^{-6}$ mbar) in the temperature range from about 200-300° C. The sublimation is carried out in a high vacuum (p about 10$^{-6}$ mbar) in the temperature range from about 250-400° C., where the sublimation is preferably carried out in the form of a fractional sublimation.

| Ex. | [Ir(L)$_2$Cl]$_2$ | Co-ligand L' | Ir(L)$_2$(L') Purification method Extractant Eluent | Yield |
|---|---|---|---|---|
| Ir(L1)$_2$(L'1) | [Ir(L1)$_2$Cl]$_2$ | 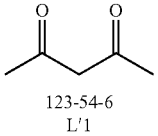<br>123-54-6<br>L'1 | 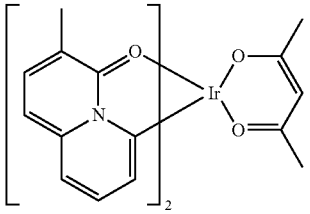<br>Chromatography<br>Silica gel/DCM | 55% |
| Ir(L16)$_2$(L'1) | [Ir(L16)$_2$Cl]$_2$ | L'1 | 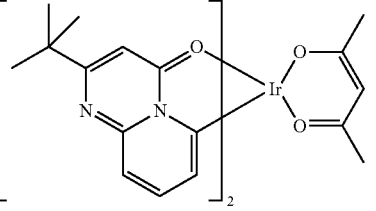<br>Chromatography<br>Silica gel/DCM | 50% |

-continued

| Ex. | [Ir(L)₂Cl]₂ | Co-ligand L' | Ir(L)₂(L') Purification method Extractant Eluent | Yield |
|---|---|---|---|---|
| Ir(L17)₂(L'2) | [Ir(L17)₂Cl]₂ | 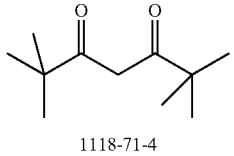 1118-71-4 L'2 | 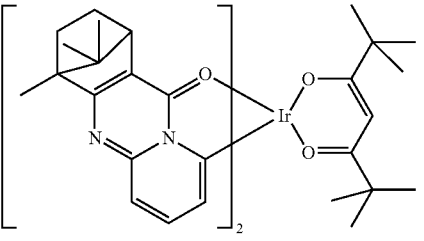 Chromatography Silica gel/EA | 49% |
| Ir(L22)₂(L'3) | [Ir(L22)₂Cl]₂ | 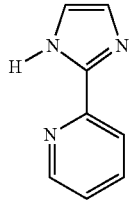 18653-75-3 L'3 | 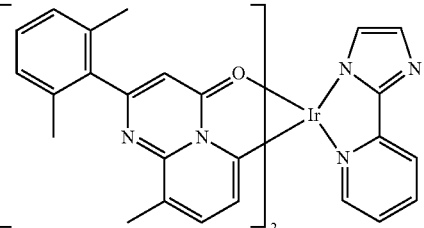 Extraction Toluene | 39% |

4) Heteroleptic Tris-Ortho-Metallated Complexes of the Formula Ir(L)₂(L') and of the Formula Ir(L)(L')₂ from [Ir(L)₂Cl]₂

The above-mentioned compounds are obtained by reaction of the crude chloro dimers of the formula [Ir(L)₂Cl]₂ with the ligands L' in dipolar protic solvents (ethylene glycol, propylene glycol, glycerol, diethylene glycol, triethylene glycol, etc.). This usually gives mixtures comprising both complex types of the formula Ir(L)₂(L') and of the formula Ir(L)(L')₂, which can be separated by chromatography. The relative amounts of the complex types of the formula Ir(L)₂(L') and of the formula Ir(L)(L')₂ can be controlled by the stoichiometric ratio of [Ir(L)₂Cl]₂ to co-ligand L'. Thus, in the case of a stoichiometric ratio of [Ir(L)₂Cl]₂ to L' of 1:2 to about 1:4, the product of the formula Ir(L)₂(L') forms in the majority, whereas, in the case of a stoichiometric ratio of [Ir(L)₂Cl]₂ to L' of about 1:6 to about 1:12, the product of the formula Ir(L)(L')₂ forms in the majority.

The crude chloro dimer of the formula [Ir(L)₂Cl]₂ obtained in 2) is initially introduced in 100 ml of the solvent indicated. The reaction mixture is degassed by passing through a stream of inert gas (nitrogen or argon) with stirring. The indicated amount of ligand L' is then added, and the mixture is stirred at 160° C. with exclusion of light for 48 h. After cooling to 70° C., 100 ml of ethanol are added dropwise, the mixture is allowed to cool with stirring, the solid which has precipitated out is filtered off with suction, washed three times with 30 ml of ethanol each time and dried in vacuo. The complexes of the formula Ir(L)₂(L) and of the formula Ir(L)(L')₂ are isolated by chromatography, with the course being followed on TLC cards. Clean fractions are combined and evaporated virtually to dryness, during which the product frequently crystallises out. Ethanol is then added, the mixture is transferred to a protective-gas frit with ethanol, washed a number of times with a little ethanol and dried in vacuo. If necessary, the product is chromatographed again until a purity >99.5% or more has been reached. The heat treatment is carried out in a high vacuum (p about $10^{-6}$ mbar) in the temperature range from about 200-300° C. The sublimation is carried out in a high vacuum (p about $10^{-6}$ mbar) in the temperature range from about 250-400° C., where the sublimation is preferably carried out in the form of a fractional sublimation.

| Ex. | [Ir(L)₂Cl]₂ | Co-ligand L' | Ir(L)₂(L') Ir(L)(L')₂ Stoichiometry Solvent [Ir(L)₂Cl]₂: L' Adsorbent/eluent | Yield |
|---|---|---|---|---|
| Ir(L1)₂(L'4) | [Ir(L1)₂Cl]₂ | 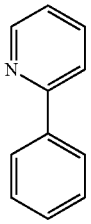 L'4 1008-89-5 | 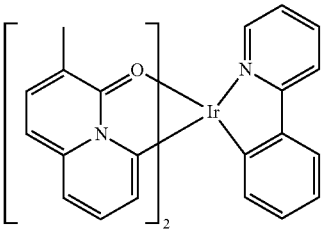 | 36% |
| Ir(L1)(L'4)₂ | | |  1:4 Ethylene glycol Silica gel/DCM | 13% |
| Ir(L1)₂(L'4) Ir(L1)(L'4)₂ | [Ir(L1)₂Cl]₂ | L'4 | 1:12 Propylene glycol Silica gel/DCM | 16% 39% |
| Ir(L12)₂(L'5) Ir(L12)(L'5)₂ | [Ir(L12)₂Cl]₂ | 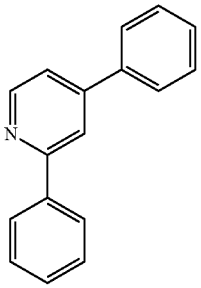 L'5 26274-35-1 | 1:4 Ethylene glycol Silica gel/DCM | 36% 14% |
| Ir(L16)₂(L'6) Ir(L16)(L'6)₂ | [Ir(L16)₂Cl]₂ | 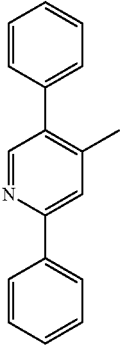 L'6 156021-08-8 | 1:6 Ethylene glycol Silica gel/EA | 18% 33% |

-continued

| Ex. | [Ir(L)₂Cl]₂ | Co-ligand L' | Ir(L)₂(L') Ir(L)(L')₂ Stoichiometry Solvent [Ir(L)₂Cl]₂: L' Adsorbent/eluent | Yield |
|---|---|---|---|---|
| Ir(L17)₂(L'7) Ir(L17)(L'7)₂ | [Ir(L17)₂Cl]₂ | L'7 458541-39-4 | 1:6 Ethylene glycol Silica gel/DCM | 16% 35% |
| Ir(L19)₂(L'8) Ir(L19)(L'8)₂ | [Ir(L19)₂Cl]₂ | L'8 4789-76-8 | 1:6 Ethylene glycol Silica gel/DCM | 16% 32% |
| Ir(L22)₂(L'9) Ir(L22)(L'9)₂ | [Ir(L15)₂Cl]₂ | L'9 1056451-61-6 | 1:8 Ethylene glycol/175° C. Silica gel/DCM | 15% 31% |

Production of OLEDs

1) Vacuum-Processed Devices:

OLEDs according to the invention and OLEDs in accordance with the prior art are produced by a general process in accordance with WO 2004/058911, which is adapted to the circumstances described here (layer-thickness variation, materials used).

The results for various OLEDs are presented in the following examples. Glass plates with structured ITO (indium tin oxide) form the substrates to which the OLEDs are applied. The OLEDs have basically the following layer structure: substrate/hole-transport layer (HTL1) consisting of HTM doped with 3% of NDP-9 (commercially available from Novaled), 20 nm/hole-transport layer 2 (HTL2)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm.

Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as M1:M2:Ir complex (55%:35%:10%) here means that material M1 is present in the layer in a proportion by volume of 55%, M2 is present in the layer in a proportion of 35% and Ir complex is present in the layer in a proportion of 10%. Analogously, the electron-transport layer may also consist of a mixture of two materials. The precise structure of the OLEDs is shown in Table 1. The materials used for the production of the OLEDs are shown in Table 4.

The OLEDs are characterised by standard methods. For this purpose, the electroluminescence spectra, the current efficiency (measured in cd/A) and the voltage (measured at 1000 cd/m² in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LD50 means that the lifetime given is the time at which the luminous density has dropped to 50% of the initial luminous density, i.e. from, for example, 1000 cd/m² to 500 cd/m². Depending on the emission colour, different initial luminances were selected. The values for the lifetime can be converted to a figure for other initial luminous densities with the aid of conversion formulae known to the person skilled in the art. The lifetime for an initial luminous density of 1000 cd/m² is a usual figure here.

Use of Compounds According to the Invention as Emitter Materials in Phosphorescent OLEDs The compounds according to the invention can be employed, inter alia, as phosphorescent emitter materials in the emission layer in OLEDs. The results of the OLEDs are summarised in Table 2.

TABLE 1

| | Structure of the OLED | | | |
|---|---|---|---|---|
| Ex. | HTL2 Thickness | EBL Thickness | EML Thickness | ETL Thickness |
| D-Ir(L1)$_3$ | HTM 100 nm | EBM 20 nm | M1:M2:Ir(L1)$_3$ (35%:60%:5%) 30 nm | ETM1:ETM2 (50%:50%) 20 nm |
| D-Ir(L2)$_3$ | HTM 120 nm | EBM 20 nm | M1:M2:Ir(L2)$_3$ (35%:60%:5%) 30 nm | ETM1:ETM2 (50%:50%) 20 nm |
| D-Ir(L3)$_3$ | HTM 100 nm | EBM 20 nm | M1:M2:Ir(L3)$_3$ (30%:60%:10%) 30 nm | ETM1:ETM2 (50%:50%) 20 nm |
| D-Ir(L4)$_3$ | HTM 70 nm | EBM 20 nm | M1:M2:Ir(L4)$_3$ (55%:40%:5%) 30 nm | ETM1:ETM2 (50%:50%) 20 nm |
| D-Ir(L5)$_3$ | HTM 110 nm | EBM 20 nm | M1:M2:Ir(L5)$_3$ (30%:70%:5%) 30 nm | ETM1:ETM2 (50%:50%) 20 nm |
| D-Ir(L6)$_3$ | HTM 110 nm | EBM 20 nm | M1:M2:Ir(L6)$_3$ (35%:60%:5%) 30 nm | ETM1:ETM2 (50%:50%) 20 nm |
| D-Ir(L7)$_3$ | HTM 100 nm | EBM 20 nm | M1:M2:Ir(L7)$_3$ (65%:30%:5%) 30 nm | ETM1:ETM2 (50%:50%) 20 nm |
| D-Ir(L8)$_3$ | HTM 100 nm | EBM 20 nm | M1:M2:Ir(L8)$_3$ (65%:30%:5%) 30 nm | ETM1:ETM2 (50%:50%) 20 nm |
| D-Ir(L9)$_3$ | HTM 100 nm | EBM 20 nm | M1:M2:Ir(L9)$_3$ (65%:30%:5%) 30 nm | ETM1:ETM2 (50%:50%) 20 nm |
| D-Ir(L10)$_3$ | HTM 110 nm | EBM 20 nm | M1:M2:Ir(L10)$_3$ (60%:30%:10%) 30 nm | ETM1:ETM2 (50%:50%) 20 nm |
| D-Ir(L11)$_3$ | HTM 110 nm | EBM 20 nm | M1:M2:Ir(L11)$_3$ (65%:30%:5%) 30 nm | ETM1:ETM2 (50%:50%) 20 nm |
| D-Ir(L12)$_3$ | HTM 110 nm | EBM 20 nm | M1:M2:Ir(L12)$_3$ (65%:30%:5%) 30 nm | ETM1:ETM2 (50%:50%) 20 nm |
| D-Ir(L14)$_3$ | HTM 100 nm | EBM 20 nm | M2:M2:Ir(L12)$_3$ (65%:30%:5%) 30 nm | ETM1:ETM2 (50%:50%) 20 nm |
| D-Ir(L14)$_3$ | HTM 70 nm | EBM 20 nm | M1:M2:Ir(L14)$_3$ (70%:25%:5%) 30 nm | ETM1:ETM2 (50%:50%) 20 nm |
| D-Ir(L15)$_3$ | HTM 70 nm | EBM 20 nm | M1:M2:Ir(L15)$_3$ (65%:30%:5%) 30 nm | ETM1:ETM2 (50%:50%) 20 nm |
| D-Ir(L16)$_3$ | HTM 100 nm | EBM 20 nm | M1:M2:Ir(16)$_3$ (65%:30%:5%) 30 nm | ETM1:ETM2 (50%:50%) 20 nm |
| D-Ir(L17)$_3$ | HTM 100 nm | EBM 20 nm | M1:M2:Ir(L17)$_3$ (65%:30%:5%) 30 nm | ETM1:ETM2 (50%:50%) 20 nm |
| D-Ir(L18)$_3$ | HTM 100 nm | EBM 20 nm | M1:M2:Ir(L18)$_3$ (65%:30%:5%) 30 nm | ETM1:ETM2 (50%:50%) 20 nm |
| D-Ir(L19)$_3$ | HTM 110 nm | EBM 20 nm | M1:M2:Ir(L19)$_3$ (65%:30%:5%) 30 nm | ETM1:ETM2 (50%:50%) 20 nm |

TABLE 1-continued

Structure of the OLED

| Ex. | HTL2 Thickness | EBL Thickness | EML Thickness | ETL Thickness |
|---|---|---|---|---|
| D-Ir(L20)$_3$ | HTM 110 nm | EBM 20 nm | M1:M2:Ir(L20)$_3$ (65%:30%:5%) 30 nm | ETM1:ETM2 (50%:50%) 20 nm |
| D-Ir(L21)$_3$ | HTM 110 nm | EBM 20 nm | M1:M2:Ir(L21)$_3$ (65%:30%:5%) 30 nm | ETM1:ETM2 (50%:50%) 20 nm |
| D-Ir(L22)$_3$ | HTM 180 nm | EBM 20 nm | M1:M2:Ir(L22)$_3$ (65%:30%:5%) 30 nm | ETM1:ETM2 (50%:50%) 20 nm |
| D-Ir(L1)$_2$(L'1) | HTM 100 nm | EBM 20 nm | M1:M2:Ir(L1)$_2$(L'1) (65%:30%:5%) 30 nm | ETM1:ETM2 (50%:50%) 20 nm |
| D-Ir(L16)$_2$(L'1) | HTM 100 nm | EBM 20 nm | M1:M2:Ir(L16)$_2$(L'1) (65%:30%:5%) 30 nm | ETM1:ETM2 (50%:50%) 20 nm |
| D-Ir(L17)$_2$(L'2) | HTM 100 nm | EBM 20 nm | M1:M2:Ir(L17)$_2$(L'2) (65%:30%:5%) 30 nm | ETM1:ETM2 (50%:50%) 20 nm |
| D-Ir(L22)$_2$(L'3) | HTM 100 nm | EBM 20 nm | M1:M2:Ir(L22)$_2$(L'3) (65%:30%:5%) 30 nm | ETM1:ETM2 (50%:50%) 20 nm |
| D-Ir(L1)$_2$(L'4) | HTM 1β0 nm | EBM 20 nm | M1:M2:Ir(L1)$_2$(L'4) (65%:30%:5%) 30 nm | ETM1:ETM2 (50%:50%) 20 nm |
| D-Ir(L1)(L'4)$_2$ | HTM 100 nm | EBM 20 nm | M1:M2:Ir(L1)(L'4)$_2$ (65%:30%:5%) 30 nm | ETM1:ETM2 (50%:50%) 20 nm |
| D-Ir(L12)(L'5)$_2$ | HTM 120 nm | — | M1:M2:Ir(L12)(L'5)$_2$ (65%:30%:5%) 30 nm | ETM1:ETM2 (50%:50%) 20 nm |
| D-Ir(L16)$_2$(L'6) | HTM 100 nm | EBM 20 nm | M1:M2:Ir(L16)$_2$(L'6) (65%:30%:5%) 30 nm | ETM1:ETM2 (50%:50%) 20 nm |
| D-Ir(L17)(L'7)$_2$ | HTM 130 nm | — | M1:M2:Ir(L17)(L'7)$_2$ (65%:30%:5%) 30 nm | ETM1:ETM2 (50%:50%) 20 nm |
| D-Ir(L19)(L'8)$_2$ | HTM 150 nm | — | M1:M2:Ir(L19)(L'8)$_2$ (50%:45%:5%) 35 nm | ETM1:ETM2 (50%:50%) 20 nm |
| D-Ir(L22)(L'9)$_2$ | HTM 150 nm | — | M1:M2:(L22)(L'9)$_2$ (55%:40%:5%) 35 nm | ETM1:ETM2 (50%:50%) 20 nm |

TABLE 2

Results of the vacuum-processed OLEDs

| Ex. | EQE (%) 1000 cd/m$^2$ | Voltage (V) 1000 cd/m$^2$ | CIE x/y 1000 cd/m$^2$ | LT50 (h) 1000 cd/m$^2$ |
|---|---|---|---|---|
| D-Ir(L1)$_3$ | 12.5 | 3.3 | 0.32/0.64 | 25,000 |
| D-Ir(L2)$_3$ | 12.9 | 3.4 | 0.40/0.58 | 33,000 |
| D-Ir(L3)$_3$ | 13.4 | 3.3 | 0.33/0.65 | — |
| D-Ir(L4)$_3$ | 9.2 | 3.8 | 0.17/0.38 | — |
| D-Ir(L5)$_3$ | 15.0 | 3.3 | 0.44/0.53 | 36,000 |
| D-Ir(L6)$_3$ | 0.5 | 3.6 | 0.72/0.27 | — |
| D-Ir(L7)$_3$ | 16.0 | 3.2 | 0.33/0.66 | — |
| D-Ir(L8)$_3$ | 16.3 | 3.3 | 0.34/0.65 | 40,000 |
| D-Ir(L9)$_3$ | 15.9 | 3.3 | 0.32/0.67 | 45,000 |
| D-Ir(L10)$_3$ | 15.5 | 3.2 | 0.40/0.58 | 48,000 |
| D-Ir(L11)$_3$ | 15.8 | 3.3 | 0.41/0.57 | — |
| D-Ir(L12)$_3$ | 15.8 | 3.3 | 0.41/0.58 | — |
| D-Ir(L13)$_3$ | 0.3 | 3.9 | — | — |
| D-Ir(L14)$_3$ | 7.9 | 3.8 | 0.27/0.69 | 6000 |
| D-Ir(L15)$_3$ | 8.4 | 4.4 | 0.24/0.55 | — |
| D-Ir(L16)$_3$ | 17.0 | 3.3 | 0.32/0.66 | 46,000 |
| D-Ir(L17)$_3$ | 18.2 | 3.3 | 0.34/0.65 | 54,000 |
| D-Ir(L18)$_3$ | 17.8 | 3.2 | 0.35/0.64 | 50,000 |
| D-Ir(L19)$_3$ | 18.1 | 3.4 | 0.40/0.58 | — |
| D-Ir(L20)$_3$ | 16.4 | 3.5 | 0.43/0.56 | — |
| D-Ir(L21)$_3$ | 17.2 | 3.2 | 0.41/0.58 | — |
| D-Ir(L22)$_3$ | 11.4 | 3.2 | 0.33/0.66 | — |
| D-Ir(L1)$_2$(L'1) | 15.6 | 3.4 | 0.35/0.64 | 38,000 |
| D-Ir(L16)$_2$(L'1) | 15.1 | 3.5 | 0.36/0.63 | — |
| D-Ir(L17)$_2$(L'2) | 16.4 | 3.7 | 0.38/0.61 | — |
| D-Ir(L22)$_2$(L'3) | 13.7 | 3.6 | 0.29/0.69 | — |
| D-Ir(L1)$_2$(L'4) | 14.6 | 3.2 | 0.32/0.67 | — |
| DIr(L1)(L'4)$_2$ | 14.5 | 3.3 | 0.33/0.66 | 52,000 |
| D-Ir(L12)(L'5)$_2$ | 16.0 | 3.2 | 0.43/0.56 | — |
| DIr(L16)$_2$(L'6) | 16.6 | 3.3 | 0.33/0.66 | 55,000 |
| D-Ir(L17)(L'7)$_2$ | 17.2 | 3.2 | 0.44/0.55 | 68,000 |
| D-Ir(L19)(L'8)$_2$ | 16.5 | 3.1 | 0.67/0.32 | 88,000 |
| D-Ir(L22)(L'9)$_2$ | 16.7 | 3.1 | 0.68/0.32 | 92,000 |

2) Solution-Processed Devices:

A: From Soluble Functional Materials

The iridium complexes according to the invention can also be processed from solution, where they result in OLEDs which are significantly simpler as far as the process is concerned, compared with the vacuum-processed OLEDs, with nevertheless good properties. The production of components of this type is based on the production of polymeric light-emitting diodes (PLEDs), which has already been described many times in the literature (for example in WO 2004/037887). The structure is composed of substrate/ITO/ PEDOT (80 nm)/interlayer (80 nm)/emission layer (80 nm)/ cathode. To this end, use is made of substrates from Technoprint (soda-lime glass), to which the ITO structure (indium tin oxide, a transparent, conductive anode) is applied. The substrates are cleaned with DI water and a detergent (Deconex 15 PF) in a clean room and then activated by a UV/ozone plasma treatment. An 80 nm layer of PEDOT (PEDOT is a polythiophene derivative (Baytron P VAI 4083sp.) from H. C. Starck, Goslar, which is supplied as an aqueous dispersion) is then applied as buffer layer by spin coating, likewise in the clean room. The spin rate required depends on the degree of dilution and the specific spin coater geometry (typically for 80 nm: 4500 rpm). In order to remove residual water from the layer, the substrates are dried by heating on a hotplate at 180° C. for 10 minutes. The interlayer used serves for hole injection, in this case HIL-012 from Merck is used. The interlayer may alternatively also be replaced by one or more layers, which merely have to satisfy the condition of not being detached again by the subsequent processing step of EML deposition from solution. In order to produce the emission layer, the emitters according to the invention are dissolved in toluene together with the matrix materials. The typical solids content of such solutions is between 16 and 25 g/l if, as here, the typical layer thickness of 80 nm for a device is to be achieved by means of spin coating. The solution-processed devices comprise an emission layer comprising (polystyrene):M1:M2:Ir complex (25%:25%:40%:10%). The emission layer is applied by spin coating in an inert-gas atmosphere, in the present case argon, and dried by heating at 130° C. for 30 min. Finally, a cathode is applied by vapour deposition of barium (5 nm) and then aluminium (100 nm) (high-purity metals from Aldrich, particularly barium 99.99% (Order No. 474711); vapour-deposition equipment from Lesker, inter alia, typical vapour-deposition pressure $5\times10^{-6}$ mbar). Optionally, firstly a hole-blocking layer and then an electron-transport layer and only then the cathode (for example Al or LiF/Al) can be applied by vacuum vapour deposition. In order to protect the device against air and atmospheric moisture, the device is finally encapsulated and then characterised. The OLED examples given have not yet been optimised, Table 3 summarises the data obtained.

TABLE 3

Results with solution-processed materials

| Ex. | Ir complex | EQE (%) 1000 cd/m² | Voltages (V) 1000 cd/m² | CIE x/y 1000 cd/m² |
|---|---|---|---|---|
| DL-Ir(L22)₃ | Ir(L22)₃ | 10.3% | 5.7 | 0.34/0.63 |
| DL-Ir(L17)(L'7)₂ | Ir(L17)(L'7)₂ | 15.0% | 5.6 | 0.40/0.58 |
| DL-Ir(L22)(L'9)₂ | Ir(L22)(L'9)₂ | 16.4% | 5.6 | 0.68/0.32 |

TABLE 4

Structural formulae of the materials used

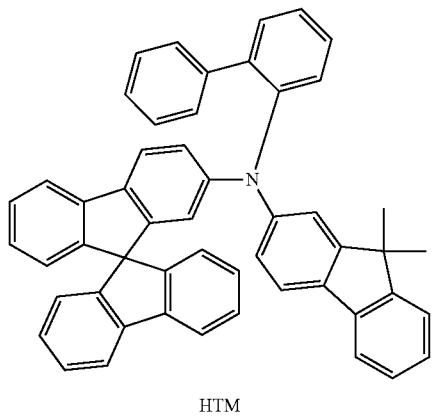

HTM

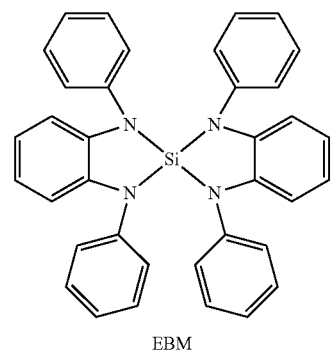 [SMILES: c1ccc(N2c3ccccc3N(c3ccccc3)[Si]23N(c2ccccc2)c2ccccc2N3c2ccccc2)cc1]

EBM

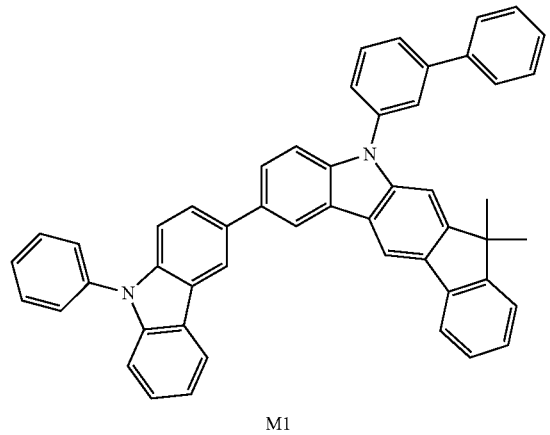 [SMILES: CC1(C)c2ccccc2-c2cc3c4cc(-c5ccc6c(c5)c5ccccc5n6-c5ccccc5)ccc4n(-c4cccc(-c5ccccc5)c4)c3cc21 ; "M1"]

M1

TABLE 4-continued

Structural formulae of the materials used

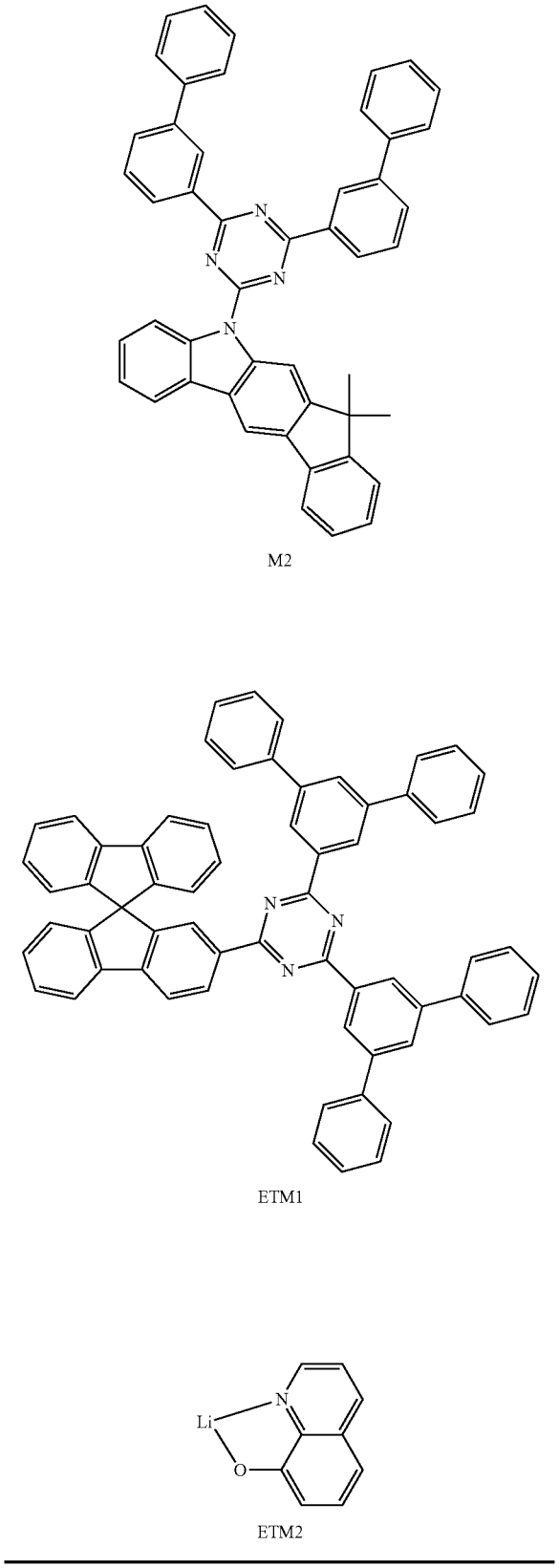

M2

ETM1

ETM2

The invention claimed is:
1. A compound of formula (1):

$$M(L)_n(L')_m \qquad (1)$$

containing a moiety $M(L)_n$ of formula (2):

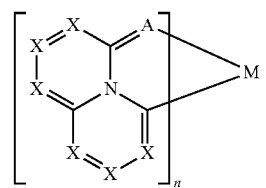

(2)

wherein
M is a transition metal;
A is on each occurrence, identically or differently, O, S, or NR;
X is on each occurrence, identically or differently, CR or N;
or two adjacent groups X are group of formula (3) or (4):

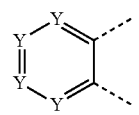

(3)

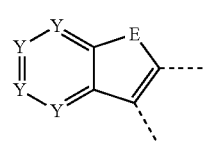

(4)

wherein
Y is on each occurrence, identically or differently, CR or N; and
E is on each occurrence, identically or differently, CR$_2$, NR, O, or S;
R is on each occurrence, identically or differently, H, D, F, Cl, Br, I, N(R$^1$)$_2$, P(R$^1$)$_2$, CN, NO$_2$, Si(R$^1$)$_3$, B(OR$^1$)$_2$, C(=O)R$^1$, P(=O)(R$^1$)$_2$, S(=O)R$^1$, S(O)$_2$R$^1$, OSO$_2$R$^1$, OH, SH, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals R$^1$, wherein one or more non-adjacent CH$_2$ groups are optionally replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O)(R$^1$), SO, SO$_2$, NR$^1$, O, S, or CONR$^1$, and wherein one or more H atoms are optionally replaced by D, F, Cl, Br, I, CN, or NO$_2$, an aromatic or heteroaromatic ring system having 5 to 60 aromatic ring atoms, which is optionally substituted by one or more radicals R$^1$, an aralkyl or heteroaralkyl group having 5 to 60 aromatic ring atoms, which is optionally substituted by one or more radicals R$^1$, an aryloxy or heteroaryloxy group having 5 to 60 aromatic ring atoms, which is optionally substituted by one or more radicals R$^1$, or a diarylamino group, diheteroarylamino group, or arylheteroarylamino group having 10 to 40 aromatic ring atoms, which is optionally substituted by one or more radicals R¹; and wherein two or more adjacent radicals R optionally define a mono- or polycyclic, aliphatic, aromatic, and/or benzo-fused ring system with one another;

R¹ is on each occurrence, identically or differently, H, D, F, Cl, Br, I, N(R²)₂, CN, NO₂, Si(R²)₃, B(OR²)₂, C(=O)R², P(=O)(R²)₂, S(=O)R², S(=O)₂R₂, OSO₂R₂, a straight-chain alkyl, alkoxy, or thioalkoxy group having 1 to 40 C atoms, a straight-chain alkenyl or alkynyl group having 2 to 40 C atoms, or a branched or cyclic alkyl, alkenyl, alkynyl, alkoxy, or thioalkoxy group having 3 to 40 C atoms, each of which is optionally substituted by one or more radicals R², wherein one or more non-adjacent CH₂ groups are optionally replaced by R²C=CR², C≡C, Si(R²)₂, Ge(R²)₂, Sn(R²)₂, C=O, C=S, C=Se, C=NR², P(=O)(R²), SO, SO₂, NR², O, S, or CONR², and wherein one or more H atoms are optionally replaced by D, F, Cl, Br, I, CN, or NO₂, an aromatic or heteroaromatic ring system having 5 to 60 aromatic ring atoms, which is optionally substituted by one or more radicals R², an aryloxy or heteroaryloxy group having 5 to 60 aromatic ring atoms, which is optionally substituted by one or more radicals R², or a diarylamino group, diheteroarylamino group, or arylheteroarylamino group having 10 to 40 aromatic ring atoms, which is substituted by one or more radicals R²; and wherein two or more adjacent radicals R¹ optionally define a mono- or polycyclic, aliphatic, or aromatic ring system with one another;

R² is on each occurrence, identically or differently, H, D, F or an aliphatic, aromatic, and/or heteroaromatic organic radical having 1 to 20 C atoms, wherein one or more H atoms are optionally replaced by D or F; and wherein two or more substituents R² optionally define a mono- or polycyclic, aliphatic or aromatic ring system with one another;

L' is, identically or differently on each occurrence, any desired co-ligand;

n is 1, 2, or 3; and m is 0, 1, 2, 3, or 4; and wherein a plurality of ligands L are optionally linked to one another or L is optionally linked to L' via any desired bridge V so as to define a tridentate, tetradentate, pentadentate or hexadentate ligand system.

2. The compound of claim 1, wherein R² is a hydrocarbon radical.

3. The compound of claim 1, wherein M is selected from the group consisting of iridium, platinum, chromium, molybdenum, tungsten, rhenium, ruthenium, osmium, rhodium, nickel, palladium, copper, silver, and gold.

4. The compound of claim 1, wherein the moiety of formula (2) is selected from the group consisting of the structures of formulae (5) to (17):

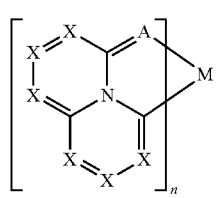
(5)

-continued

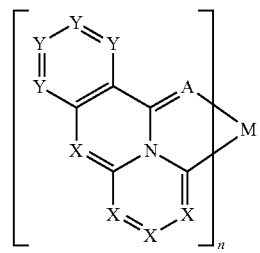
(6)

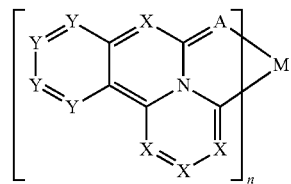
(7)

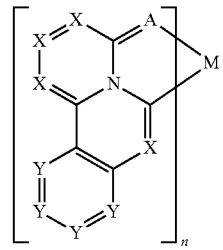
(8)

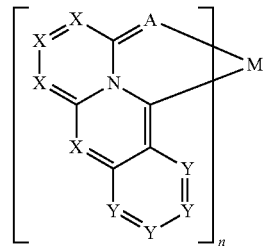
(9)

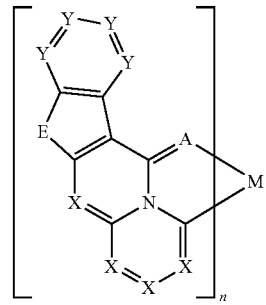
(10)

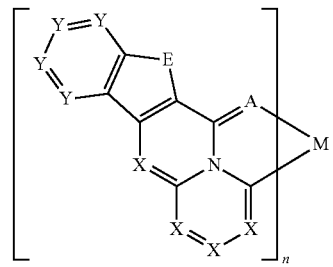
(11)

-continued

(12)
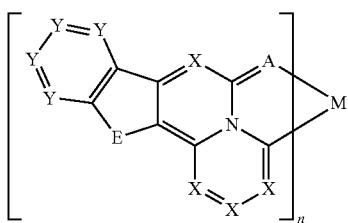

(13)
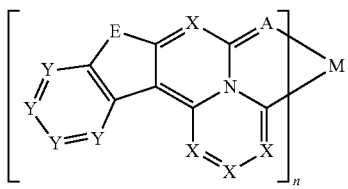

(14)
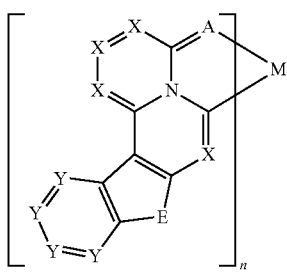

(15)
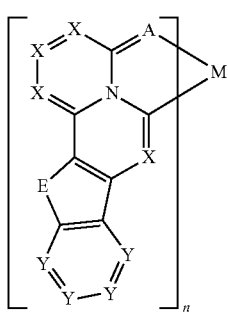

(16)
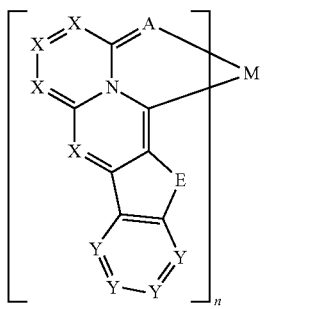

(17)
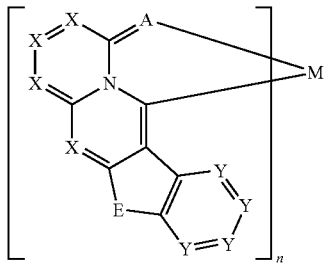

wherein

X is, identically or differently on each occurrence, for CR or N.

5. The compound of claim 1, wherein a maximum of two groups X are nitrogen and the other groups X in the ring are CR and a maximum of two groups Y are nitrogen and the other groups Y in the ring are CR.

6. The compound of claim 5, wherein a maximum of one group X per ring is nitrogen and a maximum of one group Y per ring is nitrogen.

7. The compound of claim 1, wherein the moiety of formula (2) is selected from the group consisting of the structures of formulae (5a) to (5d), (7a) to (7c), and (5a) to (8c):

(5a)
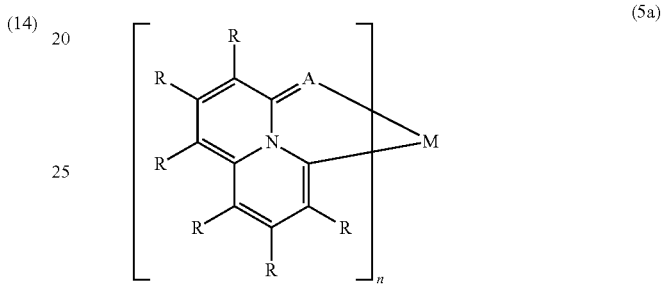

(5b)
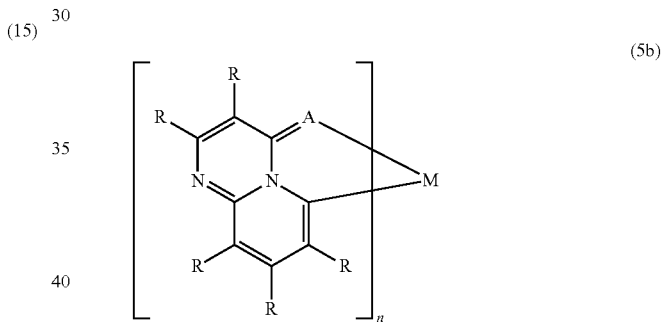

(5c)
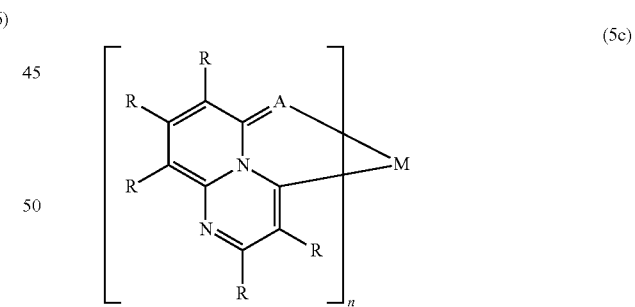

(5d)
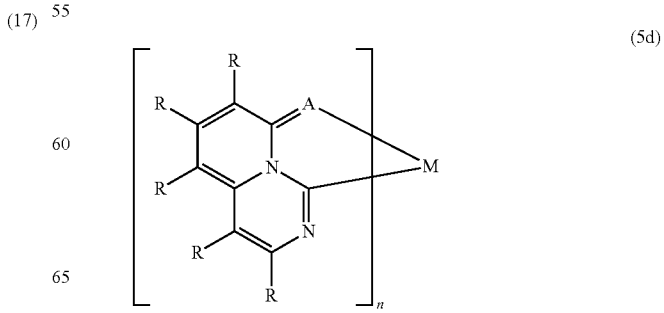

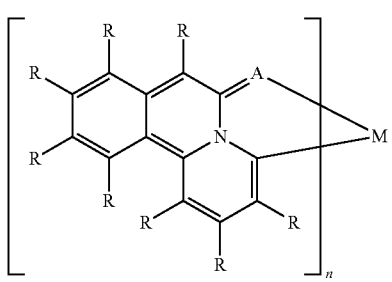
(7a)

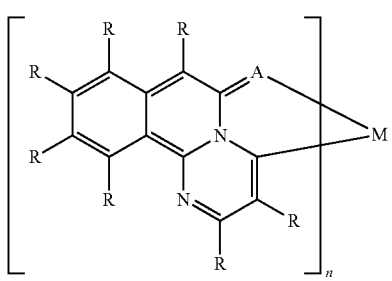
(7b)

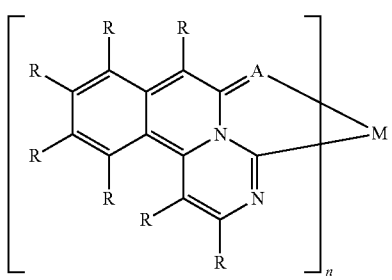
(7c)

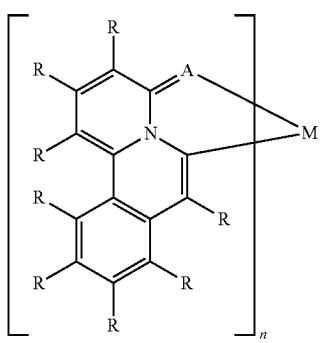
(8a)

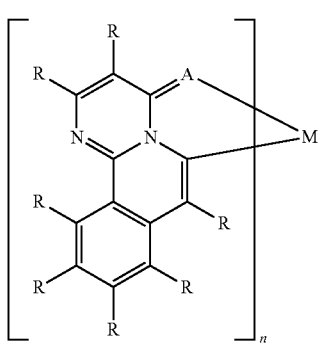
(8b)

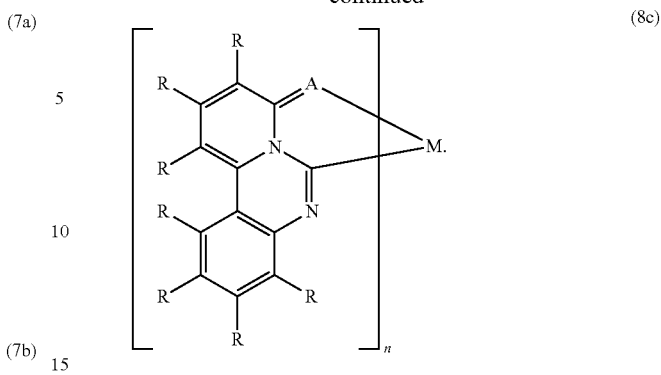
(8c)

8. The compound of claim 1, wherein A is O or S.

9. The compound of claim 1, wherein, if one or more X is N, at least one R which is not H or D is bonded adjacent to this N atom.

10. The compound of claim 9, wherein R is an alkyl group, an alkoxy group, a substituted amino group, an aralkyl group or an aromatic or heteroaromatic ring system.

11. The compound of claim 1, wherein L has two adjacent carbon atoms, each of which are substituted by radicals R, wherein the respective radicals R, together with the C atoms, define a ring selected from the group consisting of formulae (18), (19), (20), and (20a) to (20c):

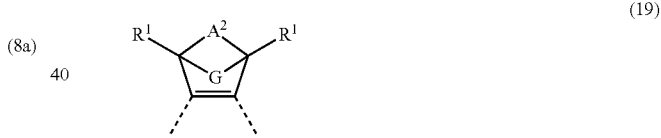
(18)

(19)

(20)

(20a)

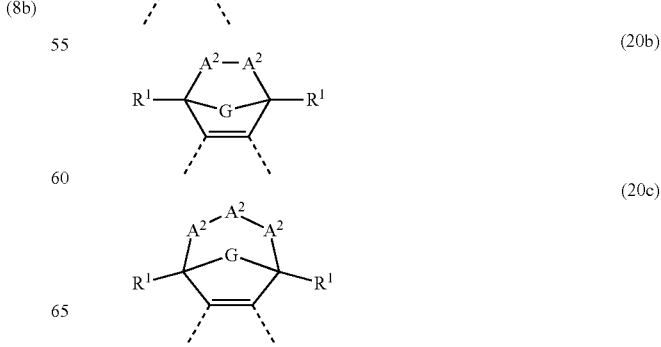
(20b)

(20c)

-continued

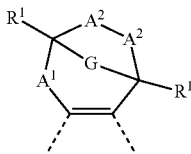
(20d)

wherein
the dashed bonds indicate the linking of the two carbon atoms in the ligand;

$A^1$ and $A^3$
are, identically or differently on each occurrence, $C(R^3)_2$, O, S, $NR^3$, or C(=O);

$A^2$ is, identically or differently on each occurrence, $C(R^1)_2$, O, S, $NR^3$, or C(=O);
or the two groups $A^2$ in formula (20) together define a group of formula (21) or (22):

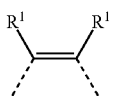
(21)

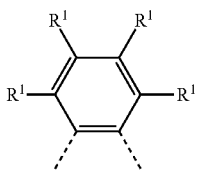
(22)

G is an alkylene group having 1, 2, or 3 C atoms, which is optionally substituted by one or more radicals $R^2$, —$CR^2$=$CR^2$—, or an ortho-linked arylene or heteroarylene group having 5 to 14 aromatic ring atoms, which is optionally substituted by one or more radicals $R^2$;

$R^3$ is, identically or differently on each occurrence, F, a straight-chain alkyl or alkoxy group having 1 to 20 C atoms or a branched or cyclic alkyl or alkoxy group having 3 to 20 C atoms, each of which is optionally substituted by one or more radicals $R^2$, wherein one or more non-adjacent $CH_2$ groups are optionally replaced by $R^2C$=$CR^2$, C≡C, $Si(R^2)_2$, C=O, $NR^2$, O, S, or $CONR^2$, and wherein one or more H atoms are optionally replaced by D or F, an aromatic or heteroaromatic ring system having 5 to 24 aromatic ring atoms, which is optionally substituted by one or more radicals $R^2$, an aryloxy or heteroaryloxy group having 5 to 24 aromatic ring atoms, which is optionally substituted by one or more radicals $R^2$, or an aralkyl or heteroaralkyl group having 5 to 24 aromatic ring atoms, which is optionally substituted by one or more radicals $R^2$; and wherein two radicals $R^3$ optionally define an aliphatic or aromatic ring system with one another; and wherein $R^3$ optionally defines an aliphatic ring system with an adjacent radical R or $R^1$;

with the proviso that no two heteroatoms in $A^1$-$A^2$-$A^3$ are bonded directly to one another.

12. The compound of claim 1, wherein the compound is selected from group consisting of the structures of formulae (24) to (28):

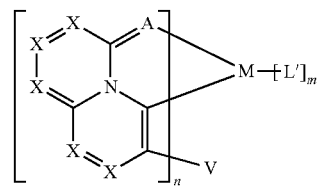
formula (24)

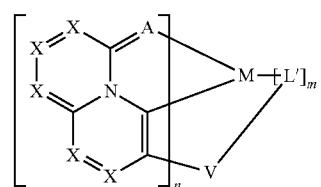
formula (25)

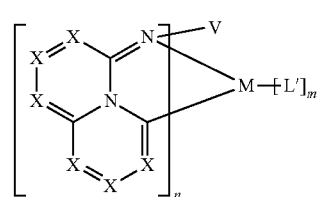
formula (26)

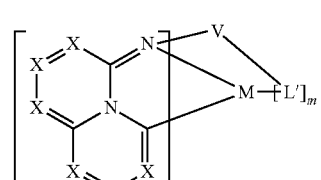
formula (27)

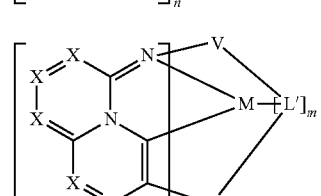
formula (28)

wherein
V is a bridging unit containing 1 to 80 atoms from the third, fourth, fifth, and/or sixth main group or a 3- to 6-membered homo- or heterocycle, which covalently bonds the part-ligands L to one another or covalently bonds L to L' to one another.

13. The compound of claim 1, wherein L' is selected, identically or differently on each occurrence, from the group consisting of carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, $F^-$, $Cl^-$, $Br^-$, $I^-$, alkylacetylides, arylacetylides, cyanide, cyanate, isocyanate, thiocyanate, isothiocyanate, aliphatic alcoholates, aromatic alcoholates, aliphatic thioalcoholates, aromatic thioalcoholates, amides, carboxylates, aryl groups, $O^{2-}$, $S^{2-}$, carbides, nitrenes, diamines, imines, diimines, diphosphines, 1,3-diketonates derived from 1,3-diketones, 3-ketonates derived from 3-ketoesters, carboxylates derived from aminocarboxylic acids, salicyliminates derived from salicylimines, dialcoholates, dithiolates, borates of nitrogen-containing heterocycles, and ligands formed by a combination of groups of formulae (43) to (65), wherein one group is bonded via a neutral nitrogen atom or a carbene carbon atom and the other group is bonded via a negatively charged carbon atom or a negatively charged nitrogen atom and the ligand is formed through these groups bonding to one another in each case at the position denoted by #:
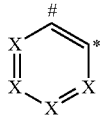 (43)
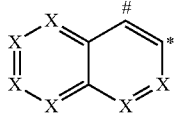 (44)
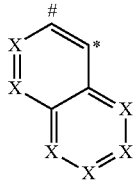 (45)
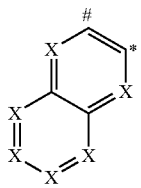 (46)
 (47)
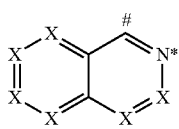 (48)
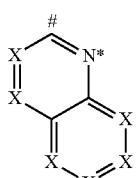 (49)
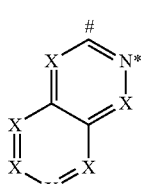 (50)
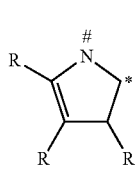 (51)
-continued
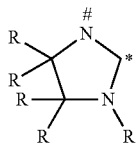 (52)
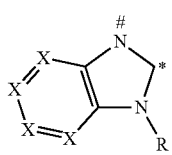 (53)
 (54)
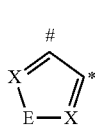 (55)
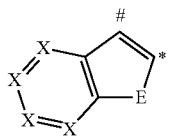 (56)
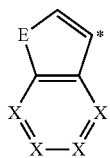 (57)
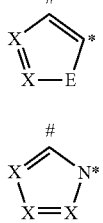 (58)
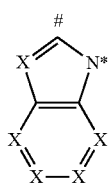 (59)
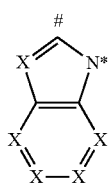 (60)
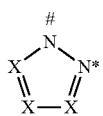 (61)
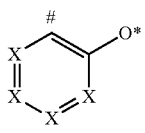 (62)

-continued

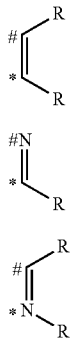

(63)

(64)

(65)

wherein the position at which the group coordinates to the metal is denoted by *.

14. A process for preparing the compound of claim 1, comprising reacting the corresponding free ligand with a metal alkoxide of formula (70), with a metal ketoketonate of formula (71), with a metal halide of formula (72), with a dimeric metal complex of formula (73), or with a metal compound which carries both alcoholate and/or halide and/or hydroxyl radicals and also ketoketonate radicals:

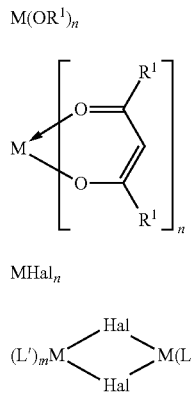

(70)

(71)

(72)

(73)

wherein Hal is F, Cl, Br, or I.

15. An oligomer, polymer, or dendrimer comprising one or more of compounds of claim 1, wherein at least one of the radicals R is a bond to the oligomer, polymer, or dendrimer.

16. A formulation comprising at least one compound of claim 1 and at least one further compound.

17. The formulation of claim 16, wherein the at least one further compound is a solvent.

18. A formulation comprising an oligomer, polymer, or dendrimer of claim 15 and at least one further compound.

19. The formulation of claim 18, wherein the at least one further compound is a solvent.

20. An oxygen sensor comprising at least one compound of claim 1.

21. An oxygen sensor comprising an oligomer, polymer, or dendrimer of claim 15.

22. An electronic device comprising at least one compound of claim 1.

23. The electronic device of claim 22, wherein the device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

24. An electronic device comprising at least one oligomer, polymer, or dendrimer of claim 15.

25. The electronic device of claim 24, wherein the device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

26. The electronic device of claim 23, wherein the electronic device is an organic electroluminescent device and the at least one compound is employed as emitting compound in one or more emitting layers.

27. The electronic device of claim 26, wherein the at least one compound is in combination with a matrix material.

* * * * *